US007348014B2

(12) United States Patent
Balloul et al.

(10) Patent No.: US 7,348,014 B2
(45) Date of Patent: Mar. 25, 2008

(54) POXVIRUS WITH TARGETED INFECTION SPECIFICITY

(75) Inventors: Jean Marc Balloul, Lingolsheim (FR); Stephane Paul, Strasbourg (FR); Michel Geist, Brumath (FR); Nathalle Silvestre, Ergersheim (FR); Philippe Erbs, Strasbourg (FR)

(73) Assignee: Transgene, S.A., Strasbourg (FR)

( * ) Notice: Subject to any disclaimer, the term of this patent is extended or adjusted under 35 U.S.C. 154(b) by 149 days.

(21) Appl. No.: 10/934,728

(22) Filed: Sep. 7, 2004

(65) Prior Publication Data

US 2005/0208074 A1 Sep. 22, 2005

Related U.S. Application Data

(63) Continuation-in-part of application No. 09/832,899, filed on Apr. 12, 2001.

(60) Provisional application No. 60/246,080, filed on Nov. 7, 2000.

(30) Foreign Application Priority Data

Apr. 14, 2000 (EP) ................................. 00440109
Jan. 22, 2001 (EP) ................................. 01440009

(51) Int. Cl.
*C12N 15/85* (2006.01)
(52) U.S. Cl. ..................... 424/232.1; 435/5; 435/235.1
(58) Field of Classification Search ..................... None
See application file for complete search history.

(56) References Cited

U.S. PATENT DOCUMENTS 5,518,888 A * 5/1996 Waldman .................... 435/7.23
6,884,786 B1 * 4/2005 Kieny et al. .................... 514/44

FOREIGN PATENT DOCUMENTS

| WO | WO 92/06180 A1 | 4/1992 |
| WO | WO 94/10323 A1 | 5/1994 |
| WO | WO 94/27643 A1 | 12/1994 |
| WO | WO 99/03885 * | 1/1999 |
| WO | WO 00/09730 A2 | 2/2000 |

OTHER PUBLICATIONS

Vazquez et al. Journal of Virology, 1999, vol. 73, p. 9098-9109.*
Antoine et al. Virology, 1998, vol. 244, p. 365-396.*
Barker et al. Science, 2001, vol. 294, p. 1-7.*
Attwood, Science, 2000, vol. 290, p. 1-6.*
Balloul et al. Cell and Molec. Biology, vol. 40, p. 49-59.*
Galmiche et al., "Expression of a functional single chain antibody on the surface . . . tumour cell targeting", Journal of General Virology, 1997, pp. 3019-3027, vol. 78, Great Britain.
Russel et al., "Retroviral vectors displaying functional antibodu fragments", Oxford University Press, 1993, pp. 1081-1085, vol. 21, No. 5, United Kingdom.

Bernard Moss, "Genetically engineered poxviruses for recombinant gene expression, vaccination, and safety", Colloquium Paper, 1996, pp. 11341-11348, vol. 93, USA.
Paul, S. "Redirected cellular cytotoxicity by infection of effector cells with a recombinant vaccinia virus encoding a tumor-specific monoclonal antibody" 2000 Cancer Gene Ther. (2000) 7, pp. 615-623.
Hsiao, J.C. "Cell Surface Proteoglycans Are Necessary for A27L Protein-Mediated cell Fusion: Identification of the N-tmerinal Region of A27L Protein as the Glycoaminoglycan-Binding Domain" Journ. Of Virol. (Oct. 1998) 72, pp. 8374-8379.
Urbanski et al., "*Internalization of E. coli ST mediated by guanylyl cyclase c in T84 human colon carcinoma cells*," Biochimica et Biophysica Acta, 1245, pp. 25-36, Elsevier Science B.V. 1995.
Rodriguez et al., "*Mapping and Nucleotide Sequence of the Vaccinia Virus Gene That Encodes a 14-Kilodalton Fusion Protein*," Journal of Virology, 61(11) pp. 3550-3554, American Society for Microbiology, 1987.
Kain et al., "*Molecular Cloning and Expression of a Novel Human trans-Golgi Network Glycoprotein, TGN51, That Contains Multiple Tyrosine-containing Motifs*" The Journal of Biological Chemistry, 273(2), pp. 981-988, The American Society for Biochemistry and Molecular Biology, Inc., 1998.
Lin et al., "*Structural Analysis of the Extracellular Domain of Vaccinia Virus Envelope Protein, A27L, by NMR and CD Spectroscopy*," The Journal of Biological Chemistry, 277(23), pp. 20949-20959, The American Society for Biochemisty and Molecular Biology, Inc., 2002.
Carrithers et al. "*Guanylyl cyclase C is selective marker for metastatic colorectal tumors in human extraintestinal tissues*," Proc. Natl. Acad. Sci., 93, pp. 14827-14832, Medical Sciences, 1996.
Vázquez et al., "*Identification of Functional Domains in the 14-kilodalton Envelope Protein (A27L) of Vaccinia Virus*," Journal of Virology, 73(11), pp. 9098-9109, American Society for Microbiology, 1999.
Chung et al., "*A27L Protein Mediates Vaccinia Virus Interaction with Cell Surface Heparan Sulfate*," Journal of Virology, 72(2), pp. 1577-1585, American Society for Microbiology, 1998.

(Continued)

*Primary Examiner*—Bruce R. Campell
*Assistant Examiner*—Agnieszka Boesen
(74) *Attorney, Agent, or Firm*—Buchanan, Ingersoll & Rooney, PC

(57) ABSTRACT

The present invention concerns a poxviral particle having a targeted infection specificity conferred by an heterologous ligand moiety present at the surface of said poxviral particle and capable of specifically recognizing and binding to an anti-ligand molecule localized at the surface of target cells. The present invention further relates to a vector comprising a nucleotide sequence encoding a chimeric polypeptide including such an heterologous ligand moiety and all or part of a natural poxviral surface polypeptide. The present invention additionally concerns compositions comprising said poxviral particle or said vector as well as their use for therapeutic and prophylactic purposes. The invention is of very special interest in gene therapy applications, in particular in preventing or treating cancer in mammals.

19 Claims, 6 Drawing Sheets

OTHER PUBLICATIONS

Vázquez et al., "*The Vaccinia Virus 14-Kilodalton (A27L) Fusion Protein Forms a Triple Coiled-Coil Structure and Interacts with the 21-Kilodalton (A17L) Virus Membrane Protein through a C-Terminal α-Helix*," Journal of Virology, 72(12), pp. 10126-10137, American Society for Microbiology, 1998.

Vanderplasschen et al., "*Intracellular and extracellular vaccinia virions enter cells by different mechanisms*," Journal of General Virology, 79, pp. 877-887, 1998.

Galmiche et al., "*Expression of a functional single chain antibody on the surface of extracellular enveloped vaccinia virus as a step towards selective tumour cell targeting*," Journal of General Virology, 78, pp. 3019-3027, 1997.

Hsiao et al., "*Vaccinia virus Envelope D8L Protein Binds to Cell Surface Chondroitin Sulfate and Mediates the Adsorption of Intracellular Mature Virions to Cells*," Journal of Virology, 73(10), pp. 8750-8761, American Society for Microbiology, 1999.

* cited by examiner

Figure 4

```
                          SEQUENCE LISTING

<160> NUMBER OF SEQ ID NOS: 52

<210> SEQ ID NO 1
<211> LENGTH: 24
<212> TYPE: DNA
<213> ORGANISM: Artificial Sequence
<220> FEATURE:
<223> OTHER INFORMATION: PCR primer to amplify the MVA 138L gene and
      flanking region

<400> SEQUENCE: 1
cagactggac ggcgtccata tgag                                           24

<210> SEQ ID NO 2
<211> LENGTH: 61
<212> TYPE: DNA
<213> ORGANISM: Artificial Sequence
<220> FEATURE:
<223> OTHER INFORMATION: antisense PCR primer to amplify the 3' end of
      MVA 138L gene and 3' flanking region

<400> SEQUENCE: 2
cattttttaa gtatagaata aaagatcccg ggagtaccat cgtgattctt accagatatt    60
a                                                                   61

<210> SEQ ID NO 3
<211> LENGTH: 61
<212> TYPE: DNA
<213> ORGANISM: Artificial Sequence
<220> FEATURE:
<223> OTHER INFORMATION: PCR primer to amplify E. coli gpt gene and H5R
      promoter

<400> SEQUENCE: 3
taatatctgg taagaatcac gatggtactc ccgggatctt ttattctata cttaaaaat    60 g                                                                   61

<210> SEQ ID NO 4
<211> LENGTH: 35
<212> TYPE: DNA
<213> ORGANISM: Artificial Sequence
<220> FEATURE:
<223> OTHER INFORMATION: antisense PCR primer to amplify E. coli gpt
      gene and H5R promoter

<400> SEQUENCE: 4
ggggttaatt aaggaagtta aaagaacaa cgccc                               35

<210> SEQ ID NO 5
<211> LENGTH: 38
<212> TYPE: DNA
<213> ORGANISM: Artificial Sequence
<220> FEATURE:
<223> OTHER INFORMATION: PCR primer to amplify the upstream region of
      MVA 138L gene
```

<400> SEQUENCE: 5 ggggaattc gagcttatag cgtttagttc aggtacgg                          38

<210> SEQ ID NO 6
<211> LENGTH: 44
<212> TYPE: DNA
<213> ORGANISM: Artificial Sequence
<220> FEATURE:
<223> OTHER INFORMATION: antisense PCR primer to amplify the upstream
      region of the MVA 138L gene

<400> SEQUENCE: 6
ggggaagctt ttaaagtaca gattttagaa actgacactc tgcg                  44

<210> SEQ ID NO 7
<211> LENGTH: 68
<212> TYPE: DNA
<213> ORGANISM: Artificial Sequence
<220> FEATURE:
<223> OTHER INFORMATION: antisense primer to amplify the upstream region
      of the MVA 138L gene

<400> SEQUENCE: 7
ggggaagctt caagagcggc acggctcccg ccgctgcgac gttcaggagg accaaggcaa  60
ccacgaac                                                          68

<210> SEQ ID NO 8
<211> LENGTH: 31
<212> TYPE: DNA
<213> ORGANISM: Artificial Sequence
<220> FEATURE:
<223> OTHER INFORMATION: PCR primer to amplify the MVA 138L gene and its
      downstream region

<400> SEQUENCE: 8
ggggaagctt atggacggaa ctcttttccc c                                31

<210> SEQ ID NO 9
<211> LENGTH: 37
<212> TYPE: DNA
<213> ORGANISM: Artificial Sequence
<220> FEATURE:
<223> OTHER INFORMATION: antisense PCR primer to amplify the MVA 138L
      gene and its downstream region

<400> SEQUENCE: 9 ggggaattc gcttatcgtt atcgggttta gcttctg                           37

<210> SEQ ID NO 10
<211> LENGTH: 68
<212> TYPE: DNA
<213> ORGANISM: Artificial Sequence
<220> FEATURE:
<223> OTHER INFORMATION: PCR primer to amplify SM3 scFv sequence

<400> SEQUENCE: 10
cgcagagtgt cagtttctaa aatctgtact ttaaatggtg cagctgcagg agtctggagg  60
aggcttgg                                                          68

<210> SEQ ID NO 11
<211> LENGTH: 58
<212> TYPE: DNA
<213> ORGANISM: Artificial Sequence
<220> FEATURE:

<223> OTHER INFORMATION: antisense PCR primer to amplify the SM3 scFv
      sequence

<400> SEQUENCE: 11
gatcgtcatc tccggggaaa agagttccgt ccatcagttt ggttcctcca ccgaacac          58

<210> SEQ ID NO 12
<211> LENGTH: 57
<212> TYPE: DNA
<213> ORGANISM: Artificial Sequence
<220> FEATURE:
<223> OTHER INFORMATION: PCR primer to amplify the SM3 scFv sequence

<400> SEQUENCE: 12
cctgaacgtc gcagcggcgg gagccgtgcc gctcttggtg cagctgcagg agtctgg          57

<210> SEQ ID NO 13
<211> LENGTH: 111
<212> TYPE: DNA
<213> ORGANISM: Artificial Sequence
<220> FEATURE:
<223> OTHER INFORMATION: sequence of the synthetic p11K7.5 promoter

<400> SEQUENCE: 13
ataaaaatat agtagaattt catttgtttt tttctatgct ataaatagga tccgataaag         60
tgaaaaataa ttctaattta ttgcacggta aggaagtaga atcataaga a                 111

<210> SEQ ID NO 14
<211> LENGTH: 53
<212> TYPE: DNA
<213> ORGANISM: Artificial Sequence
<220> FEATURE:
<223> OTHER INFORMATION: PCR primer to amplify the p11k7.5 promoter

<400> SEQUENCE: 14
gggggatccc ccgggctgca gaagcttttc tttatgattc tacttcctta ccg              53

<210> SEQ ID NO 15
<211> LENGTH: 50
<212> TYPE: DNA
<213> ORGANISM: Artificial Sequence
<220> FEATURE:
<223> OTHER INFORMATION: antisense PCR primer to amplify the p11k7.5
      promoter

<400> SEQUENCE: 15 gggggagat ctaagcttgt cgacataaaa atatagtaga atttcatttg                    50

<210> SEQ ID NO 16
<211> LENGTH: 77
<212> TYPE: DNA
<213> ORGANISM: Artificial Sequence
<220> FEATURE:
<223> OTHER INFORMATION: synthetic sequence

<400> SEQUENCE: 16
gatggtgaca gggggaatgg caagcaagtg ggatctcgag ttgggtgact ttggtgacag         60
atactactgt gtttaag                                                       77

<210> SEQ ID NO 17
<211> LENGTH: 85
<212> TYPE: DNA
<213> ORGANISM: Artificial Sequence
<220> FEATURE:
<223> OTHER INFORMATION: synthetic sequence -continued

<400> SEQUENCE: 17
gatccttaaa cacagtagta tctgtcacca aagtcaccca actcgagatc ccacttgctt    60
gccattcccc ctgtcaccat ctgca                                         85

<210> SEQ ID NO 18
<211> LENGTH: 32
<212> TYPE: DNA
<213> ORGANISM: Artificial Sequence
<220> FEATURE:
<223> OTHER INFORMATION: PCR primer to amplify the 5' F13L flanking
      region of MVA

<400> SEQUENCE: 18
gagaggatcc gggtatctag ccacagtaaa tc                                 32

<210> SEQ ID NO 19
<211> LENGTH: 32
<212> TYPE: DNA
<213> ORGANISM: Artificial Sequence
<220> FEATURE:
<223> OTHER INFORMATION: antisense PCR primer to amplify the 5' F13L
      flanking region of MVA

<400> SEQUENCE: 19
tttcgaattc ggaatctgta ttctcaatac cg                                 32

<210> SEQ ID NO 20
<211> LENGTH: 33
<212> TYPE: DNA
<213> ORGANISM: Artificial Sequence
<220> FEATURE:
<223> OTHER INFORMATION: PCR primer to amplify the 3' F13L flanking
      region of MVA

<400> SEQUENCE: 20
atctgaattc gtggagatga tgatagttta agc                                33

<210> SEQ ID NO 21
<211> LENGTH: 34
<212> TYPE: DNA
<213> ORGANISM: Artificial Sequence
<220> FEATURE:
<223> OTHER INFORMATION: antisense PCR primer to amplify the 3' f13L
      flanking region of MVA

<400> SEQUENCE: 21
aacaggatcc cttatacatc ctgttctatc aacg                               34

<210> SEQ ID NO 22
<211> LENGTH: 12
<212> TYPE: PRT
<213> ORGANISM: Artificial Sequence
<220> FEATURE:
<223> OTHER INFORMATION: ligand for Gc-C receptor
<220> FEATURE:
<221> NAME/KEY: VARIANT
<222> LOCATION: 5, 6, 7, 10
<223> OTHER INFORMATION: Xaa = Any Amino Acid

<400> SEQUENCE: 22

Cys Glu Leu Cys Xaa Xaa Xaa Ala Cys Xaa Gly Cys
 1               5                  10

<210> SEQ ID NO 23
<211> LENGTH: 12

```
<212> TYPE: PRT
<213> ORGANISM: Artificial Sequence
<220> FEATURE:
<223> OTHER INFORMATION: Gc-C ligand CEIC type
<220> FEATURE:
<221> NAME/KEY: VARIANT
<222> LOCATION: 5, 6, 7, 10
<223> OTHER INFORMATION: Xaa = Any Amino Acid

<400> SEQUENCE: 23

Cys Glu Ile Cys Xaa Xaa Xaa Ala Cys Xaa Gly Cys
 1               5                  10

<210> SEQ ID NO 24
<211> LENGTH: 18
<212> TYPE: PRT
<213> ORGANISM: Artificial Sequence
<220> FEATURE:
<223> OTHER INFORMATION: Sta ligand

<400> SEQUENCE: 24

Asn Thr Phe Tyr Cys Cys Glu Leu Cys Cys Asn Pro Ala Cys Ala Gly
 1               5                  10                  15

Cys Tyr

<210> SEQ ID NO 25
<211> LENGTH: 15
<212> TYPE: PRT
<213> ORGANISM: Artificial Sequence
<220> FEATURE:
<223> OTHER INFORMATION: endogenous GC-C receptor ligand

<400> SEQUENCE: 25

Pro Gly Thr Cys Glu Ile Cys Ala Tyr Ala Ala Cys Thr Gly Cys
 1               5                  10                  15

<210> SEQ ID NO 26
<211> LENGTH: 81
<212> TYPE: PRT
<213> ORGANISM: Artificial Sequence
<220> FEATURE:
<223> OTHER INFORMATION: deleted mutant of the vaccinia p14 protein

<400> SEQUENCE: 26

Ala Lys Arg Glu Ala Ile Val Lys Ala Asp Glu Asp Asp Asn Glu Glu
 1               5                  10                  15

Thr Leu Lys Gln Arg Leu Thr Asn Leu Glu Lys Lys Ile Thr Asn Val
                20                  25                  30

Thr Thr Lys Phe Glu Gln Ile Glu Lys Cys Cys Lys Arg Asn Asp Glu
            35                  40                  45

Val Leu Phe Arg Leu Glu Asn His Ala Glu Thr Leu Arg Ala Ala Met
    50                  55                  60

Ile Ser Leu Ala Lys Lys Ile Asp Val Gln Thr Gly Arg Arg Pro Tyr
65                  70                  75                  80

Glu

<210> SEQ ID NO 27
<211> LENGTH: 25
<212> TYPE: DNA
<213> ORGANISM: Artificial Sequence
<220> FEATURE:
<223> OTHER INFORMATION: primer

<400> SEQUENCE: 27
```
acgcagagtg tcagtttcta aaatc                                        25

<210> SEQ ID NO 28
<211> LENGTH: 35
<212> TYPE: DNA
<213> ORGANISM: Artificial Sequence
<220> FEATURE:
<223> OTHER INFORMATION: primer

<400> SEQUENCE: 28
ttaaagtaca gattttagaa actgacactc tgcgt                              35

<210> SEQ ID NO 29
<211> LENGTH: 57
<212> TYPE: DNA
<213> ORGANISM: Artificial Sequence
<220> FEATURE:
<223> OTHER INFORMATION: primer

<400> SEQUENCE: 29
tgtactttaa atgaacacat ttactgctg tgaactttgt tgtaatcctg cctgtgc      57

<210> SEQ ID NO 30
<211> LENGTH: 57
<212> TYPE: DNA
<213> ORGANISM: Artificial Sequence
<220> FEATURE:
<223> OTHER INFORMATION: primer

<400> SEQUENCE: 30
ataacaccca gcacaggcag gattacaaca aagttcacag cagtaaaatg tgttcat     57

<210> SEQ ID NO 31
<211> LENGTH: 50
<212> TYPE: DNA
<213> ORGANISM: Artificial Sequence
<220> FEATURE:
<223> OTHER INFORMATION: primer

<400> SEQUENCE: 31
tgggtgttat gacggaactc ttttccccgg agatgacgat cttgcaattc              50

<210> SEQ ID NO 32
<211> LENGTH: 40
<212> TYPE: DNA
<213> ORGANISM: Artificial Sequence
<220> FEATURE:
<223> OTHER INFORMATION: primer

<400> SEQUENCE: 32
gaattgcaag atcgtcatct ccggggaaaa gagttccgtc                         40

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
aatataaata acgcagagtg                                               20

<210> SEQ ID NO 34
<211> LENGTH: 20
<212> TYPE: DNA
<213> ORGANISM: Artificial Sequence

```
<220> FEATURE:
<223> OTHER INFORMATION: primer

<400> SEQUENCE: 34
tcagttgctg gaattgcaag                                                    20

<210> SEQ ID NO 35
<211> LENGTH: 60
<212> TYPE: DNA
<213> ORGANISM: Artificial Sequence
<220> FEATURE:
<223> OTHER INFORMATION: primer

<400> SEQUENCE: 35
tgtactttaa atgcggttcg tggttgcctt ggtcctcctg aacgtcgcag cggcgggagc        60

<210> SEQ ID NO 36
<211> LENGTH: 63
<212> TYPE: DNA
<213> ORGANISM: Artificial Sequence
<220> FEATURE:
<223> OTHER INFORMATION: primer

<400> SEQUENCE: 36
caagagcggc acggctcccg ccgctgcgac gttcaggagg accaaggcaa ccacgaaccg        60
cat                                                                     63

<210> SEQ ID NO 37
<211> LENGTH: 60
<212> TYPE: DNA
<213> ORGANISM: Artificial Sequence
<220> FEATURE:
<223> OTHER INFORMATION: primer

<400> SEQUENCE: 37
cgtgccgctc ttgatgaaca cattttactg ctgtgaactt gttgtaatc ctgcctgtgc         60

<210> SEQ ID NO 38
<211> LENGTH: 32
<212> TYPE: DNA
<213> ORGANISM: Artificial Sequence
<220> FEATURE:
<223> OTHER INFORMATION: primer

<400> SEQUENCE: 38 ggggggcat gcttaattaa aagtatattc aa                                       32

<210> SEQ ID NO 39
<211> LENGTH: 32
<212> TYPE: DNA
<213> ORGANISM: Artificial Sequence
<220> FEATURE:
<223> OTHER INFORMATION: primer

<400> SEQUENCE: 39
ggggggggat ccttagcgac cggagattgg cg                                      32

<210> SEQ ID NO 40
<211> LENGTH: 27
<212> TYPE: DNA
<213> ORGANISM: Artificial Sequence
<220> FEATURE:
<223> OTHER INFORMATION: primer

<400> SEQUENCE: 40
```

```
ttatagatct tttattctat acttaaa                                       27

<210> SEQ ID NO 41
<211> LENGTH: 24
<212> TYPE: DNA
<213> ORGANISM: Artificial Sequence
<220> FEATURE:
<223> OTHER INFORMATION: primer

<400> SEQUENCE: 41
attaggatcc aaacttaacg gata                                          24

<210> SEQ ID NO 42
<211> LENGTH: 26
<212> TYPE: DNA
<213> ORGANISM: Artificial Sequence
<220> FEATURE:
<223> OTHER INFORMATION: primer

<400> SEQUENCE: 42
ggggagatct atggtgagca agggcg                                        26

<210> SEQ ID NO 43
<211> LENGTH: 30
<212> TYPE: DNA
<213> ORGANISM: Artificial Sequence
<220> FEATURE:
<223> OTHER INFORMATION: primer

<400> SEQUENCE: 43
gatctggatc cttacttgta cagctcgtcc                                    30

<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
gtatagactt tacattttct                                               20

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
caaactttgt tgttacatta                                               20

<210> SEQ ID NO 46
<211> LENGTH: 50
<212> TYPE: DNA
<213> ORGANISM: Artificial Sequence
<220> FEATURE:
<223> OTHER INFORMATION: primer

<400> SEQUENCE: 46
tgggtgttat gctaaacgcg aagcaattgt taaagccgat gaagacgaca              50

<210> SEQ ID NO 47
<211> LENGTH: 40
<212> TYPE: DNA
<213> ORGANISM: Artificial Sequence
```

-continued

```
<220> FEATURE:
<223> OTHER INFORMATION: primer

<400> SEQUENCE: 47
tgtcgtcttc atcggcttta acaattgctt cgcgtttagc                              40

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
gtttcctcat tgtcgtcttc                                                    20

<210> SEQ ID NO 49
<211> LENGTH: 43
<212> TYPE: DNA
<213> ORGANISM: Artificial Sequence
<220> FEATURE:
<223> OTHER INFORMATION: primer

<400> SEQUENCE: 49 gggggggagat ctatatacta tatagtaata ccaatactca aga                         43

<210> SEQ ID NO 50
<211> LENGTH: 36
<212> TYPE: DNA
<213> ORGANISM: Artificial Sequence
<220> FEATURE:
<223> OTHER INFORMATION: primer

<400> SEQUENCE: 50
ggggggggat ccactgttct ttatgattct acttcc                                  36

<210> SEQ ID NO 51
<211> LENGTH: 30
<212> TYPE: DNA
<213> ORGANISM: Artificial Sequence
<220> FEATURE:
<223> OTHER INFORMATION: primer

<400> SEQUENCE: 51
tttaaggatc catggacgga actcttttcc                                         30

<210> SEQ ID NO 52
<211> LENGTH: 29
<212> TYPE: DNA
<213> ORGANISM: Artificial Sequence
<220> FEATURE:
<223> OTHER INFORMATION: primer

<400> SEQUENCE: 52
gggggaattc ttactcatat ggacgccgt                                          29
```

POXVIRUS WITH TARGETED INFECTION SPECIFICITY

RELATED APPLICATIONS

This application is a continuation-in-part of U.S. Ser. No. 09/832,899, filed Apr. 12, 2001, which claims benefit under 35 UCS 119(e) of U.S. Ser. No. 60/246,080, filed Nov. 7, 2000.

The present invention concerns a poxviral particle having a targeted infection specificity conferred by an heterologous ligand moiety present at the surface of said poxviral particle and capable of specifically recognizing and binding to an anti-ligand molecule localized at the surface of target cells. The present invention further relates to a vector comprising a nucleotide sequence encoding a chimeric polypeptide including such an heterologous ligand moiety and all or part of a natural poxviral surface polypeptide. The present invention additionally concerns compositions comprising said poxviral particle or said vector as well as their use for therapeutic and prophylactic purposes. The invention is of very special interest in gene therapy applications, in particular in preventing or treating cancer in mammals.

Gene therapy can be defined as the transfer of genetic material into a cell or an organism. The possibility of treating human disorders by gene therapy has changed in few years from the stage of theoretical considerations to that of clinical applications. The first protocol applied to man was initiated in the USA in September 1990 on a patient suffering from adenine deaminase (ADA) deficiency. This first encouraging experiment has been followed by numerous new applications and promising clinical trials based on gene therapy are currently ongoing (see for example clinical trials listed at the web pages of the U.S. National Institutes of Health and at the Journal of Gene Medicine's "Gene Therapy Clinical Trials Worldwide" web site).

Successful gene therapy depends principally on the efficient delivery of a therapeutic gene of interest to make its expression possible into cells of a living organism. Therapeutic genes can be transferred into cells using a wide variety of vectors resulting in either transient expression (transfection) or permanent transformation of the host genome. During the past decade, a large number of viral, as well as non-viral, vectors has been developed for gene transfer (see for example Robbins et al., 1998, Tibtech 16, 35-40 and Rolland, 1998, Therapeutic Drug Carrier Systems 15, 143-198 for reviews).

The most widely used viral vectors are derived from retroviruses and adenoviruses (for review, see Miller, 1997, Human Gene Therapy 8, 803-815). However, other viral vectors such as Sindbis virus-derived vectors or poxvirus-derived vectors, are emerging as promising candidates for in vivo gene transfer.

Poxviruses are a group of complex enveloped viruses that distinguish them principally by their unusual morphology, their large DNA genome and their cytoplasmic site of replication. The genome of several members of poxviridae, including the Copenhagen vaccinia virus (VV) strain (Goebel et al., 1990, Virol. 179, 247-266 and 517-563; Johnson et al., 1993, Virol. 196, 381-401) and the modified vaccinia virus Ankara (MVA) strain (Antoine et al., 1998, Virol. 244, 365-396), have been mapped and sequenced. VV has a double-stranded DNA genome of about 192 kb coding for about 200 proteins of which approximately 100 are involved in virus assembly. MVA is a highly attenuated vaccinia virus strain generated by more than 500 serial passages of the Ankara strain of vaccinia virus (CVA) on chicken embryo fibroblasts (Mayr et al., 1975, Infection 3, 6-16). The MVA virus was deposited before Collection Nationale de Cultures de Microorganismes (CNCM) under depositary N° I-721. Determination of the complete sequence of the MVA genome and comparison with the Copenhagen VV genome allows the precise identification of the alterations which occurred in the viral genome and the definition of seven deletions (I to VII) and numerous mutations leading to fragmented ORFs (Open Reading Frame) (Antoine et al., 1998, Virology 244, 365-396).

The natural pathway for intracellular uptake of enveloped viruses involves a series of steps including the binding of a viral polypeptide exposed at the virus surface to a cellular receptor and a fusion mechanism between the viral and cellular membranes resulting in viral genome release into the cytoplasm of the infected cell.

However, in poxvirus special case, the exact delivery pathway analysis is complicated by the existence of two morphologically distinct forms of infectious virus, termed intracellular mature virus (IMV) and extracellular enveloped virus (EEV). The IMV form is, among other particularities, characterized by a monolipid envelope surrounding the viral core (FIG. 1) and is principally localized in the cytoplasm of the infected cells, although it might be extracellularly released after lysis of the infected cells. Many of the natural polypeptides exposed at the surface of the IMV lipid envelope have been identified, such as for example the p14 kDa and p21 kDa proteins, respectively encoded by the A27L gene (Rodriguez at al., 1985, J. Virol. 56, 482-488; Rodriguez et Estaban, 1987, J. Virol. 61, 3550-3554) and the A17L gene, as well as proteins encoded by L1R, A14L, D8L, A9L (Yeh et al., 2000, J. Virol. 74, 9701-9711), E10R (Senkevich et al., 2000, Virol. 5, 244-252) and H3L genes. Compared to the IMV, the EEV form has an additional outer lipid membrane envelope (double lipid layer) acquired from the trans-Golgi network cisternae. It corresponds to the viral form released outside the infected cells. The EEV surface membrane envelope shows about 10 proteins which are absent from the IMV surface, such as for example the encoded B5R, A34R and hemagglutinin (HA) gene products (FIG. 1). The co-existence of said IMV and EEV forms has been described for most of the vaccinia strains (e.g. Copenhagen and MVA strains) as well as for other poxviruses such as the fowl poxvirus (Boulanger et al., 2000, J. Gen. Virol. 81, 675-687).

The different morphologies of IMV and EEV suggest the occurrence of different mechanisms for the penetration of these poxviral forms into the host cells. It has been recently proposed that the EEV delivery pathway is mediated by endocytosis and subsequent pH-dependent membrane fusion pathway, whereas the IMV form fuses directly with the cellular membrane in a pH-independent manner (Vanderplasschen et al., 1998, J. Gen. Virol. 79, 877-887). Two cellular receptors that mediate IMV binding and intracellular uptake have been recently identified: the heparan sulfate which is a glycosaminoglycan (GAG) side chain of cell surface proteoglycans (Chung et al., 1998, J. Virol. 72, 1577-1585) and another GAG component, the chondroitin sulfate (Hsiao et al., 1999, J. Virol. 73, 8750-8761). Both receptor interacts with a different IMV surface polypeptide, respectively the p14 (binding with heparan sulfate) and D8L gene product (binding with chondroitin sulfate), suggesting different type of virus-GAG interactions.

The vaccinia virus 14-kDa protein (p14) plays an important role in the infectious property of the virus. The p14 protein is anchored in the IMV lipid envelope by association with the 21-kDa protein (p21). The p14 protein is involved in the IMV delivery pathway, probably by participating to the attachment to the cell-surface heparan sulfate (Chung et al., 1998, J. Virol. 72, 1577-1585). In addition, the fusion process has been attributed to said p14 protein. Furthermore, as a general statement, it has been shown that the IMV surface polypeptides are closely related to IMV infectious property and that their mutation or deletion dramatically impaired IMV dissemination (Dallo et al., 1987, Virology 159, 423-32). The p14 protein is also necessary for EEV formation and virus spread outside the infected cells. Recently, the functional domains required for binding to cell surface heparan sulfate receptor, for virus/cell membrane fusion and virus release have been mapped within the 43 first N-terminal amino acids of the p14 (Vazquez and Esteban, 1999, J. Virol. 73, 9098-9109). Besides, Vazquez et al. (1998, J. Virol. 72, 10126-10137) have shown that the C-terminal domain of the p14 is involved in the binding with the p21 protein.

Many recombinant poxviral vectors expressing various therapeutic genes have been reported in the literature. In particular, VV expressing cytokine genes (Peplinski et al., 1995, Ann. Surg. Oncol. 2, 151-159; Whitman et al., 1994, Surgery 116, 183-188), B7.1 immunostimulatory gene (Hodge et al., 1994, Cancer Res. 54, 5552-5555), ICAM-1 (Uzendoski et al., 1997, Hum. Gene Ther. 8, 851-860) or suicide genes such as the thymidine kinase gene of herpes simplex virus-1 (TK HSV-1) (Puhlmann et al., 1999, Hum. Gene Ther. 10, 649-657) and the cytosine deaminase gene (Gnant et al., 1999, Cancer Res. 59, 3396-3403) have been proposed for cancer therapy. In addition, their anti-tumoral activity has been demonstrated in animal models. Vectors based on MVA strain have also been proposed (Sutter and Moss, 1992, Proc. Natl. Acad. Sci. USA 89, 10847-10851; Carroll and Moss, 1995, BioTechniques 19, 352-355; Antoine et al., 1996, Gene 177, 43-46; Schleiflinger et al., 1996, Arch. Virol. 141, 663-669).

However, vaccinia virus displays a very broad host range and can infect most vertebrates cells. Again, it should be noted that the IMV and EEV forms differ with respect to this disseminating property because the EEV presenting onto its surface a larger variety of polypeptides than onto the IMV surface, it is more prone to disseminate widely than IMV. Although, whatever form is considered, this absence of infection selectivity could be regarded as a disadvantage for special applications where it is desirable to limit adverse effects that could result from the expression of transferred genes (i.e. cytotoxic genes) in the non-target cells. Accordingly, it would be interesting to modify the virus in order to restrict its host range or direct the infection to one or more specific target cell populations.

The modification of viral tropism has already been achieved with certain viruses. For example in WO93/09221, influenza virus tropism is modified by inhibition of the viral hemagglutinin polypeptide which normally mediates the binding of the virus to the cellular receptor by means of a monoclonal antibody and by coupling the virus with an antibody capable of interacting with the transferrin receptor expressed onto targeted cells.

Roux et al. (1989, Proc. Natl. Acad Sci. USA 86, 9079-9083) reports the infection of human cells with a mouse ecotropic recombinant retrovirus using two biotinylated antibodies directed to the retroviral envelope gp70 and to a cellular antigen of the human major histocompatibility complex (MHC), respectively.

WO94/10323 describes targeted adenoviruses vectors exhibiting at their surface a fiber protein modified by fusion with a single chain antibody, in order to direct adenoviral infection to the cells expressing the antibody-recognized antigen.

However, controlled targeting of poxviral particles has been hampered by the intrinsic complexity of the poxviruses and the existence of the two different infectious forms. In this regard, Galmiche et al. (1997, J. Gen. Virol. 78, 3019-3027) reports the construction of EEV particles for tumor cells targeting. A single chain antibody directed against the tumour-associated antigen ErbB-2 was fused to the viral hemagglutinin (HA) in order to be expressed at the EEV surface. ErbB-2 is an epidermal growth factor receptor that is over-expressed onto human adenocarcinoma cells. Although the fusion protein is exposed at the surface of the EEV particle and is able to bind cultured human adenocarcinoma cells in vitro, the authors did not observe preferential infection towards ErbB-2 expressing cells of the EEV having the antibody-HA fusion. It is presumed that the modified EEV particle still contains yet unidentified protein(s) allowing infection of a broad range of cells.

Therefore, the technical problem underlying the present invention is the provision of improved methods and means for the targeting of poxviral particles to specific cells. This technical problem is solved by the provision of the embodiments as defined hereby.

The present invention concerns a poxviral particle having a targeted infection specificity towards target cells wherein said particle infects preferably said target cells and wherein said specificity is conferred by at least one heterologous ligand moiety which is localized at the surface of said poxviral particle and which is capable of binding an antiligand molecule localized at the surface of said target cells, with the proviso that when said poxviral particle is an EEV vaccinia virus particle said ligand is not an antibody directed to ErbB-2.

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" whereever used herein includes the meaning of "and", "or" and "all or any other combination of the elements connected by said term".

The term "about" or "approximately" as used herein means within 20%, preferably within 10%, and more preferably within 5% of a given value or range.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

The terms "polynucleotide", "nucleic acid" and "nucleic acid molecule" are used interchangeably, and refer to a polymeric form of nucleotides of any length, either deoxyribonucleotides or ribonucleotides, or analogs thereof. The term polynucleotide, as used herein, encompasses double- and single-stranded, linear or circular, natural or synthetic polynucleotide molecules. Non-limiting examples of polynucleotides include gene or gene fragment, cDNA, messenger RNA (mRNA), antisense RNA, transfer RNA, ribosomal RNA, ribozyme or DNA encoding such RNAs, exon, intron, recombinant polynucleotide, plasmid, vector, viral genome, isolated DNA of any sequence, isolated RNA of any sequence, oligonucleotide, probe, and primer or mixtures thereof. Thus, a polynucleotide may be in the form of a poxviral genomic DNA, recombinant or not, defective or not, wild-type or not. Moreover, a polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term <<amino acid>> and residues are synonyms. This term refers to natural, unnatural and/or synthetic amino acids, including D or L optical isomers, modified amino acids and amino acid analogs.

The terms "polypeptide", "peptide" and "protein" are used interchangeably herein to refer to polymers of amino acid residues of any length (two or more) covalently joigned by peptide bonds. The polymer can be linear, cyclic or branched, it may comprise modified and/or non modified amino acids, and it may be interrupted by non-amino acids. These terms also encompass an amino acid polymer that has been modified (e.g. disulfide bond formation, glycosylation, lipidation, acetylation, phosphorylation) or any other manipulation, such as conjugation with a labeling component. As a general indication if the peptide chain is long (e.g. more than 50 amino acid residues), it is preferably referred as a polypeptide or a protein in the context of the invention.

"Homologous" polynucleotides are polynucleotides that share a significant proportion of identical nucleotide residues. "Homologous" polypeptides are polypeptides that share a significant proportion of identical amino acid residues. More specifically, the term "homologous" refers to a degree of identity between two sequences of at least 70%, more preferably of at least 80%, most preferably of at least 90% and even more preferably of at least 95%. The methods available in the art to determine the pourcentage of identity between two given sequences are known to the person skilled in the art.

The term "modification" as used herein refers to a deletion, substitution or addition of one or more amino acid residue(s) of a polypeptide or any combination of these possibilities. When several modifications are contemplated in the context of the present invention, they can concern consecutive amino acid residues and/or non consecutive residues. Modification(s) can be made in a number of ways known to those skilled in the art using recombinant techniques, including enzymatically cutting followed by modification and ligation of defined fragment, or by site-directed mutagenesis, especially by the Sculptor™ in vitro mutagenesis system (Amersham, Les Ullis, France) or by PCR techniques. Native amino acid residues for modification can be selected by any methods.

The term "poxviral particle" as used herein encompasses either empty poxviral particle (also called pseudo-poxviral particle) as well as poxviral particle comprising a nucleic acid (e.g a poxviral genome or an appropriate vector) displaying the specific infection properties described herein. In the context of the present invention, the poxviral particle may be obtained from any member of the poxviridae family (e.g. vaccinia virus, avipoxvirus, cowpox, entomopox, monkey pox, swine pox or penguin pox) In a general manner, numerous publications relate to the sequence and biology of the poxviruses and poxviral strains cited above. Suitable "avipoxvirus" include without limitation, canarypoxvirus (e.g. ALVAC strain described in U.S. Pat. No. 5,766,598), fowlpoxvirus (e.g. TROVAC strain described in U.S. Pat. No. 5,766,598 and fowlpox strain described in U.S. Pat. No. 5,180,675 and EP 314 569), pigeonpoxvirus, quailpoxvirus, peacockpoxvirus, sparrowpoxvirus and turkeypoxvirus. Preferably, however, the poxviral particle of the invention originates (is obtained or isolated) from a vaccinia virus and especially a vaccinia virus of Copenhagen, Wyeth or Ankara modified (MVA) strain. For information, the majority of the poxviruses suitable in the context of the present invention are available in recognized collections such as ATCC (fowlpox ATCC VR-251, monkey pox ATCC VR-267, swine pox ATCC VR-363, canarypox ATCC VR-111, cowpox ATCC VR-302) or ICTV (Canberra, Australia) (Copenhagen virus code 58.1.1.0.001; GenBank accession number M35027).

The poxviral particle of the invention may originate from a wild-type virus or from any derivatives thereof. In this respect, attenuated poxvirus are preferred in the context of the present invention. In a general manner, an attenuated poxvirus originates from a parent virus (e.g. a pathogenic virus) and upon infection of cells exhibits a lower mortality and/or morbidity and/or toxicity as compared to the parent virus. Examples of attenuated poxviruses are known in the art and include ALVAC or TROVAC or MVA.

As mentioned previously, gene nomenclature is different according to the poxvirus strains. However, to facilitate the reading of the present application, the gene nomenclature used throughout the specification is that of Copenhagen vaccinia strain. However, as used herein, it is used also for the equivalent genes and gene products (proteins) of other poxviridae. For information, correspondance between Copenhagen and MVA genes can be found in Table I of Antoine et al. (1998, Virol. 244, 365-396). For example, Copenhagen A27L gene is refered as 138L in MVA, both genes encoding a p14-kDa protein. MVA and Copenhagen p14 proteins share more than 98% identity both at the amino acid and nucleotide levels, similar functions, and similar localization at the IMV surface. Thus, unless the context clearly dictates otherwise, when it is referred herein to a p14 protein or to a poxviral p14 protein, this means the p14 protein of a vaccinia virus (e.g. p14 of MVA or Copenhagen virus) or a p14 functional equivalent of any other poxviridae (e.g. fowlpox). When it is referred herein to the A27L gene, this means the p14-encoding gene of a vaccinia virus (e.g. the 138L gene of MVA) or a gene encoding a p14 functional equivalent of any other poxviridae. The term "functional equivalent" as used herein refers to a poxviral protein which is involved at least in the poxvirus attachment and entry in the permissive host cell as the vaccinia p14 protein but have a different molecular weight (larger or smaller than 14 kDa).

The poxviral particle of the invention may be either an IMV or an EEV form. In a preferred embodiment, it is an IMV particle. By way of illustration, an IMV particle comprises the viral core including the viral genome surrounded by a monolayer lipid envelope with viral polypeptides present at its surface including the products encoded by the A27L (p14 protein), L1R, A14L, A17L (p21 protein) D8L, A9L, E10R and H3L genes. As compared to an IMV particle, an "EEV" particle is surrounded by an additional bilayer lipid envelope exposing at its surface cellular as well as viral polypeptides including the products encoded by the B5R, A34R and HA genes.

The term "a targeted infection specificity (of a poxviral particle) towards target cells" as used herein refers to a controlled infection specificity, where a poxviral particle of the present invention is engineered to display a new or enhanced tropism towards said target cells, compared to a related non modified (i.e. wild type) poxvirus particle. As a result, the poxviral particle of the present invention shows a propensity to infect said target cells unlike its related non modified poxviral particle, which means that the poxviral particle of the present invention infects more efficiently or more rapidly its target cells (displaying at their surface the anti-ligand recognized by the ligand moiety displayed at the surface of the poxviral particle of the invention) than non target cells (that do not display at their surface such an anti-ligand), whereas a related non modified poxviral particle will infect said target cells with a lower or a similar efficiency compared to non-target cells. This preferred infectious property can be easily determined by comparing the infection property of the poxviral particle of the present invention with infection property of its related non modified poxviral particle towards target cells and non target cells, either in vitro (e.g. in cultured cells) or in vivo (e.g. in animal models) and under the same experimental conditions. In vitro experimental conditions for analyzing infection properties are provided in Examples of the present specification, however other methods are well known by those skilled in the art and are thus usable in the context of the invention. For example, when a mixture of poxviral particles according to the invention and of related non modified poxviral particles are used to infect cultured target cells with relatively short infection time (lower than 30 min and especially 1 to 10 min), a majority (at least 60%, preferably, at least 70% and more preferably, at least 80%) of the poxviral particles according to the invention comprised in the original mixture are able to infect said target cells, whereas a minority (at most 40%, preferably, at most 30% and more preferably, at most 20%) of the related non modified poxviral particles comprised in the original mixture are able to infect said target cells. This results in an enrichment of the quantity of poxviral particles according to the invention present in the mixture at each infection round. Such an enrichment can be evaluated by determining the viral titers of the respective poxviral particles by standard techniques.

In combination, the poxviral particle of the invention can show a reduced capability of binding to a native cellular receptor such as heparan sulfate or chondroitin sulfate-containing receptors than a related non modified poxviral particle (e.g. to provide a "detargeted poxvirus vector or particle). Although any protein located at the surface of the poxviral particle and mediating or assisting directly or indirectly in the attachment or virus entry into a permissive host cell can be modified, it is preferred that the poxviral p14 protein be modified as described below.

The term "native cellular receptor" as used herein refers to at least a cellular component present at the surface of a cell that a wild-type poxvirus (e.g. an infectious poxvirus particle equiped with a wild-type p14 protein) infects, said cellular component being bound by a component present at the surface of said poxviral particle, the binding of said cellular component and said viral component promotes or initiates the virus entry into this permissive cell. Representative examples of native cellular receptor include witout limitation heparan sulfate and chondroitin receptors.

As used herein, the term "heparan sulfate receptor" or "heparan sulfate-containing receptor" refers to the heparin or heparan sulfate-containing receptor which normally interacts with the wild-type poxviral p14 protein at the early stage of virus infection, to mediate poxvirus attachment to a host cell. (see for example Chung et al. 1998, J. Virol. 72, 1577-1585). The structure of Heparin and heparan sulfate is for example illustrated in FIG. 18-15 of Biochemistry (4$^{th}$ edition, Lubert Stryer; ed Freeman and Compagny, New York) and can be defined as a copolymer of glucosamine and glucuronic or iduronic acid with various sulfatations and/or acetylation modifications. Heparan sulfate is like heparin except that it has fewer N-and O-sulfate groups and more N-acetyl. The structure and the saccharide side chains of the various heparan sulfates-containing receptors encompassed by the present invention can vary according to their tissue distribution or their biological activities. Such heparan sulfate-containing receptors can be identified by conventional techniques in the art, combining techniques from virology, carbohydrate biochemistry, molecular biology and mass spectrometry.

The term "ligand moiety" as used in the present invention defines any moiety capable of recognizing and binding to at least one anti-ligand molecule that is expressed or exposed at the surface of a target cell. It provides the target cell binding and infection specificity to the poxviral particle of the invention. It is evident by reading the specification that said anti-ligand molecule is different from the native cellular receptor mediating poxvirus uptake (e.g. cellular heparan sulfate or chondroitin sulfate receptor). According to the invention, the ligand moiety is localized on the surface of the claimed poxviral particle. Depending on the used coupling method (see below), said ligand moiety may be a moiety added to and exposed on the viral particle surface (for example by chemical coupling) or a moiety fused in the particle envelope structure (for example by genetic coupling).

"Heterologous" means "non-native", i.e. that said ligand moiety is not found at the surface of a wild type poxviral particle. By extension, "homologous" refers to the polypeptides or natural moieties found at the surface of a wild type poxviral particle. The anti-ligand molecule localized at the surface of a target cell is preferably one that the wild type poxviral particle does not bind or one that the wild type poxviral particle binds but with a lower specificity than a poxviral particle of the present invention. The binding specificity between a ligand and a given anti-ligand molecule can be determined according to techniques of the art, including ELISA, immunofluorescence and surface plasmon resonance-based technology (Biacore AB).

In general, the ligand moieties that may be used in the context of the present invention are widely described in the literature; it is a moiety able to confer to the poxviral particle of the invention, the ability to bind to a given anti-ligand molecule or a class of anti-ligand molecules localized at the surface of at least one target cell. Suitable anti-ligand molecules include without limitation polypeptides selected from the group consisting of cell-specific markers, tissue-specific markers, cellular receptors, viral antigens, antigenic epitopes and tumor-associated markers. Anti-ligand molecules may moreover consist in sugar, lipid, glycolipid, antibody, etc. . . . According to the invention, a ligand moiety may be for example a lipid, a glycolipid, an hormone, a sugar, a polymer (e.g. PEG, polylysine, PEI, . . . ), a polypeptide, an oligonucleotide, a vitamin, an antigen, a lectin, a polypeptide moiety presenting targeting property such as for example JTS1 (WO 94/40958), an antibody or combination thereof. A fragment of the precited ligand moiety can also be employed provided that it retains the targeting property of the natural molecule.

Preferably, the ligand moiety used in the present invention is a polypeptide having a minimal length of 7 amino acids. It is either a native polypeptide or a polypeptide derived from a native polypeptide. "Derived" means containing (i)

one or more modifications with respect to the native sequence (e.g. addition, deletion and/or substitution of one or more residues), (ii) amino acid analogs, including not naturally occurring amino acids or (iii) substituted linkages as well as (vi) other modifications known in the art. This term encompasses variant and chimeric polypeptides obtained by fusing sequences of various origins. In addition, the ligand moiety may have a linear or cyclized structure (e.g. by flanking at both extremities a polypeptide ligand by cysteine residues). Additionally, the ligand moiety in use in the invention may include modifications of its original structure by way of substitution or addition of chemical moieties (e.g. glycosylation, alkylation, acetylation, amidation, phosphorylation, addition of sulfhydryl groups and the like). The invention further contemplates modifications that render the ligand moiety detectable. For this purpose, modifications with a detectable moiety can be envisaged (i.e. a scintigraphic, radioactive, fluorescent, or dye labels and the like). Suitable radioactive labels include but are not limited to $Tc^{99m}$, $I^{123}$ and $In^{111}$. Such detectable labels may be attached to the ligand moiety by any conventional techniques and may be used for diagnostic purposes (e.g. imaging of tumoral cells).

In one preferred embodiment, the anti-ligand molecule is an antigen (e.g. a cell-specific antigen, a disease-specific antigen, an antigen specifically expressed on the surface of engineered target cells, . . . ) and the ligand moiety is an antibody. The term "antibody" is thus used to refer to any antibody-like molecule that has an antigen binding region, and this term includes antibody fragments such as Fab', Fab, F(ab')2, single domain antibodies (dAbs), Fv, scFv (single chain Fv), linear antibodies, diabodies, and the like. The techniques for preparing and using various antibody-based constructs and fragments are well known in the art (see for example Immunology, third edition 1993, Roitt, Brostoff and Male, ed Gambli, Mosby). The ligand moiety may be a monoclonal antibody. Monoclonal antibodies which will bind to many of these antigens are already known but in any case, with today's techniques in relation to monoclonal antibody technology, antibodies may be prepared to most antigens. The ligand moiety may be a part of an antibody (for example a Fab fragment) or a synthetic antibody fragment (for example, ScFv).

Suitable monoclonal antibodies to selected antigens may be prepared by known techniques, for example those disclosed in "Monoclonal Antibodies: A manual of techniques", H. Zola (CRC Press, 1988) and in "Monoclonal Hybridoma Antibodies: Techniques and Applications", J. G. R. Hurrell (CRC Press, 1982). Suitably prepared non-human antibodies may be "humanized" in known ways, for example by inserting the CDR regions of mouse antibodies into the framework of human antibodies. Additionally, as the variable heavy (VH) and variable light (VL) domains of the antibody are involved in antigen recognition, variable domains of rodent origin may be fused to constant domains of human origin such that the resultant antibody retains the antigenic specificity of the rodent parental antibody (Morrison et al (1984) Proc. Natl. Acad. Sci. USA 81, 6851-6855).

Antigenic specificity of antibodies is conferred by variable domains including Fab-like molecules (Better et al (1988) Science 240, 1041); Fv molecules (Skerra et al (1988) Science 240, 1038); ScFv molecules where the VH and VL partner domains may be linked via a flexible oligopeptide (Bird et al (1988) Science 242, 423; Huston et al (1988) Proc. Natl. Acad. Sci. USA 85, 5879) and dAbs comprising isolated V domains (Ward et al (1989) Nature 341, 544). A general review of the techniques involved in the synthesis of antibody fragments which retain their specific binding sites is to be found in Winter & Milstein (1991) Nature 349, 293-299.

According to an advantageous embodiment, ligand moiety is selected among antibody fragments, rather than whole antibodies. Effector functions of whole antibodies, such as complement binding, are removed. ScFv and dAb antibody fragments may be expressed as fusions with other polypeptides. Minimal recognition units may be derived from the sequence of one or more of the complementary-determining regions (CDR) of the Fv fragment. Whole antibodies, and F(ab')2 fragments are "bivalent". By "bivalent" we mean that the said antibodies and F(ab') 2 fragments have two antigen combining sites. In contrast, Fab, Fv, ScFv, dAb fragments and minimal recognition units are monovalent, having only one antigen combining sites.

In a further embodiment the ligand moiety is at least part of a specific moiety implicated in the binding of a target cell-surface polypeptide. Of course, said target cell-surface polypeptides (e.g. hormone receptors) may themselves be target cell-specific antigens and may be recognized by ligand moieties which have the property of any one of a monoclonal antibody, a ScFv, a dAb or a minimal recognition unit.

In a preferred embodiment, the ligand moiety allows to target a virally infected cell and is capable of recognizing and binding to a viral component (e.g. envelope glycoprotein) or capable of interfering with the virus biology (e.g. entry, replication . . . ). For example, the targeting of a HIV (Human Immunodeficiency Virus) infected cell can be performed with a ligand moiety specific for an epitope of the HIV envelope, such as a ligand moiety derived from the 2F5 antibody (Buchacher et al., 1992, Vaccines 92, 191-195) recognizing a highly conserved epitope of the transmembrane glycoprotein gp41 or with a ligand moiety interferring with HIV attachment to its cellular receptor CD4 (e.g. the extracellular domain of the CD4 molecule).

In another preferred embodiment, the ligand moiety allows to target a tumoral cell and is capable of recognizing and binding to a molecule related to the tumoral status, such as a tumor-specific antigen, a cellular protein differentially or over-expressed in tumoral cells or a gene product of a cancer-associated virus.

Examples of tumor-specific antigens include but are not limited to MUC-1 related to breast cancer (Hareuveni et al., 1990, Eur. J. Biochem 189, 475-486), the products encoded by the mutated BRCA1 and BRCA2 genes related to breast and ovarian cancers (Miki et al., 1994, Science 226, 66-71; Futreal et al., 1994, Science 226, 120-122; Wooster et al., 1995, Nature 378, 789-792), APC related to colon cancer (Polakis, 1995, Curr. Opin. Genet. Dev. 5, 66-71), prostate specific antigen (PSA) related to prostate cancer, (Stamey et al., 1987, New England J. Med. 317, 909), carcinoma embryonic antigen (CEA) related to colon cancers (Schrewe et al., 1990, Mol. Cell. Biol. 10, 2738-2748), tyrosinase related to melanomas (Vile et al., 1993, Cancer Res. 53, 3860-3864), receptor for melanocyte-stimulating hormone (MSH) which is expressed in high number in melanoma cells, ErbB-2 related to breast and pancreas cancers (Harris et al., 1994, Gene Therapy 1, 170-175), and alpha-foetoprotein related to liver cancers (Kanai et al., 1997, Cancer Res. 57, 461-465).

A preferred ligand moiety in use in the present invention is a fragment of an antibody capable of recognizing and binding to the MUC-1 antigen and thus targeting the MUC-1 positive tumor cells. A more preferred ligand moiety is the scFv fragment of the SM3 monoclonal antibody which recognizes the tandem repeat region of the MUC-1 antigen (Burshell et al., 1987, Cancer Res. 47, 5476-5482; Girling et al., 1989, Int J. Cancer 43, 1072-1076; Dokurno et al., 1998, J. Mol. Biol. 284, 713-728).

Another preferred ligand moiety in use in the present invention is a ligand moiety capable of recognizing and binding to the Guanylyl cyclase C (GC-C) receptor. The GC-C receptor is expressed on the surface of intestinal mucosal cells (apical pole) and on primary and metastatic adenocarcinomas of colorectal cancer (e.g. metastatic adenocarcinomas present in liver, lung, lymph nodes and/or ovary). The GC-C receptor was also found to function as the principal receptor for heat-stable enterotoxin (Sta), major causative factors in E. coli-induced diarrhea (Carrithers et al, 1996, Proc. Natl. Acad. Sci. USA 93, 14827-14832; Urbanski et al, 1995, Biochim Biophys Acta 1245, 29-36). A preferred ligand moiety to target the GC-C receptor is a peptide of of at least 12 amino acid residues comprising the sequence CELCXXXACXGC (SEQ ID NO: 22) or CEICXXXACXGC (SEQ ID NO: 23). A particularly preferred ligand moiety is the Sta peptide which comprises the amino acid sequence disclosed in SEQ ID NO: 24 (N T F Y C CELC C N P AC A GC Y). It was found to binds to GC-C receptor with a high affinity (Kd=$10^{-10}$M). Other suitable ligand moieties include without limitation endogenous ligands (Garbers et al., 1992, Cell 71, 1-4) such as guanylin, uroguanylin, with a special preference for a ligand peptide comprising the sequence PGTCEICAYAACTGC (SEQ ID NO: 25).

Examples of cellular proteins differentially or overexpressed in tumor cells include but are not limited to the receptor for interleukin 2 (IL-2) overexpressed in some lymphoid tumors, GRP (Gastrin Release Peptide) overexpressed in lung carcinoma cells, pancreas, prostate and stomach tumors (Michael et al., 1995, Gene Therapy 2, 660-668), TNF (Tumor Necrosis Factor) receptor, epidermal growth factor receptors, Fas receptor, CD40 receptor, CD30 receptor, CD27 receptor, OX-40, alphav integrins (Brooks et al., 1994, Science 264, 569) and receptors for certain angiogenic growth factors (Hanahan, 1997, Science 277, 48). Based on these indications, it is within the scope of those skilled in the art to define an appropriate ligand moiety capable of recognizing and binding to such proteins. To illustrate, IL-2 is a suitable ligand moiety to bind to IL-2 receptor.

Suitable gene products of cancer-associated viruses include but are not limited to human papilloma virus (HPV) E6 and E7 early polypeptides as well as L1 and L2 late polypeptides (EP 0 462 187, U.S. Pat. No. 5,744,133 and WO98/04705) that are expressed in cervical cancer and EBNA-1 antigen of Epstein-Barr virus (EBV) associated with Burkitt's lymphomas (Evans et al., 1997, Gene Therapy 4, 264-267).

In still another preferred embodiment, the ligand moiety allows to target tissue-specific anti-ligands. Such anti-ligands can be present at the surface of or expressed by a narrow class of cell types or a broader group encompassing several cell types including for example any organ or system. Examples of such organs and systems, include respiratory system (trachea, upper airways, lower airways, alveoly), nervous system and sensitory organs (e.g. skin, ear, nasal, tongue, eye), digestive system (e.g. oral epithelium, salivary glands, stomach, small intestines, duodenum, colon, gall bladder, pancreas, rectum), muscular system (e.g. cardiac muscle, skeletal muscle, smooth muscle, connective tissue, tendons, etc), immune system (e.g. bone marrow, stem cells, spleen, thymus, lymphatic system, etc), circulatory system (e.g. muscles connective tissue, endothelia of the arteries, veins, capillaries, etc), reproductive sytem (e.g. testis, prostate, cervix, ovaries), urinary system (e.g. bladder, kidney, urethra), and endocrine or exocrine glands (e.g. breast, adrenal glands, pituitary glands), etc.

For example, ligand moieties suitable for targeting liver cells include but are not limited to those derived from ApoB (apolipoprotein) able to bind to the LDL receptor, alpha-2-macroglobulin able to bind to the LPR receptor, alpha-1 acid glycoprotein able to bind to the asialoglycoprotein receptor and transferrin able to bind to the transferrin receptor. A ligand moiety for targeting activated endothelial cells may be derived from the sialyl-Lewis-X antigen (able to bind to ELAM-1), from VLA-4 (able to bind to the VCAM-1 receptor) or from LFA-1 (able to bind to the ICAM-1 receptor). A ligand moiety derived from CD34 is useful to target the hematopoïetic progenitor cells through binding to the CD34 receptor. A ligand moiety derived from ICAM-1 is more intended to target lymphocytes through binding to the LFA-1 receptor. The targeting of neuronal, glial, or endothelial cells can be performed through the use of ligand moieties directed for example to tissue-factor receptor (e.g. FLT-1, CD31, CD36, CD34, CD105, CD13, ICAM-1; McCormick et al., 1998, J. Biol. Chem. 273, 26323-26329), thrombomodulin receptor (Lupus et al., 1998, Suppl. 2 S120), VEGFR-3 (Lymboussaki et al., 1998, Am. J. Pathol. 153, 395-403), VCAM-1 (Schwarzacher et al., 1996, Artherosclerosis 122, 59-67) or other receptors. The targeting of blood clots can be made via fibrinogen or aIIbb3 peptide. Inflamed tissues can be targeted through selectins, VCAM-1, ICAM-1, etc. Finally, the targeting of T-helper cells may use a ligand moiety derived from HIV gp-120 or a class II MHC antigen capable of binding to the CD4 receptor.

Moreover, suitable ligand moieties also include linear stretches of amino acids, such as polylysine, polyarginine and the like recognized by integrins. Also, a ligand moiety can comprise a commonly employed tag peptide (e.g. short amino acids sequences known to be recognized by available antisera, such as sequences from glutathione-S-transferase (GST) from Shistosoma manosi, thioredoxin beta galactosidase, or maltose binding protein (MPB) from E. coli, human alkaline phosphatase, the FLAG octapeptide, hemagluttinin (HA).

It will be appreciated by those skilled in the art that ligand moieties which are polypeptides may be conveniently made using recombinant DNA techniques. The ligand moiety may be fused to a protein on the surface of the virus particle as disclosed below or they may be synthesized independently for example by de novo synthesis or by expression of the appropriate DNA fragment in eukaryotic as well as prokaryotic cells then coupled to the virus particle as disclosed below. The nucleic acid sequences encoding many of the ligand moieties are known, for example those for peptide hormones, growth factors, cytokines and the like and may readily be found by reference to publically accessible nucleotide sequence databases such as EMBL and GenBank. Once the nucleotide sequence is known it is obvious to the person skilled in the art how to make DNA encoding the chosen ligand moiety using, for example, chemical DNA synthetic techniques or by using the polymerase chain reaction to amplify the required DNA from genomic DNA or from tissue-specific cDNA. Many cDNAs encoding peptide hormones, growth factors, all or part of antibodies, cytokines and the like, all of which may be useful as ligand moieties, are generally commercially available.

By "target cells", we refer the cells that the poxviral particle of the invention can preferably infect, e.g. through the inteaction of the ligand moiety present at the viral surface with its corresponding anti-ligand present or expressed at the surface of the target cell. Depending on the nature of the ligand moiety and/or of the anti-ligand, "target cells" may designate a unique type of cell or group of different types of cells having as a common feature on their surface anti-ligand(s) recognized by ligand moiety(s) present onto poxviral particles of the invention. For the purpose of the invention, a target cell consists of any mammalian cell (preferably human cells) which can be infected with a poxviral particle according to the present invention. The cell may be a primary cell, a transformed cell or a tumoral cell of any origin. Suitable target cells include but are not limited to hematopoïetic cells (totipotent stem cells, leukocytes, lymphocytes, monocytes, macrophages, dendritic cells and the like), muscle cells (satellite, myocytes, myoblasts, skeletal or smooth muscle cells, heart cells), pulmonary cells, tracheal cells, hepatic cells, epithelial cells, endothelial cells or fibroblasts.

By "ligand moiety (or alternatively, anti-ligand molecule) is localized at the surface of the poxviral particle (or alternatively, of the target cells)", we shall mean that said ligand moiety (or said anti-ligand molecule) is accessible onto the surface of the poxviral particle (or of the target cells) for binding with its specific anti-ligand molecule (or respectively, ligand moiety) when said poxviral particle is contacted with said target cell. This accessibility can be measured in vitro without undue experiment using methods widely disclosed in literature.

According to the invention, the poxviral particle of the invention is operably coupled with an heterologous ligand moiety in use in the invention. "Operably coupled" means that said particle and ligand moiety are in a relationship permitting them to function in their intended manner (i.e. the ligand moiety is accessible onto the surface of the poxviral particle for targeting infection to the target cell). The coupling may be made by different means that are well known to those skilled in the art including covalent, non covalent or genetic means. In the context of the present invention, the heterologous ligand moiety can be coupled to or inserted to any of the viral polypeptides displayed at the surface of said poxviral particle (such as those cited hereinafter in connection with IMV and EEV particles or any combination thereof).

Covalent coupling of ligand moieties to the surface of the poxviral particle may be performed directly through reactive functional groups or indirectly by a spacer group or other activating moiety. In particular, coupling may be done with (i) homobifunctional or (ii) heterobifunctional cross-linking reagents, with (iii) carbodiimides, (iv) by reductive amination or (vi) by activation of carboxylates (see for example Bioconjugate techniques 1996; ed G Hermanson; Academic Press).

Homobifunctional cross linkers including glutaraldehyde and bis-imidoester like DMS (dimethyl suberimidate) may be used to couple amine groups of the ligand moiety to lipid structures (e.g. of the IMV envelope) containing diacyl amines.

Many heterobifunctional cross linkers may be used in the present invention, in particular those having both amine reactive and sulfhydryl-reactive groups, carbonyl-reactive and sulfhydryl-reactive groups and sulfhydryl-reactive groups and photoreactive linkers. Suitable heterobifunctional crosslinkers are described in Bioconjugate techniques (1996) 229-285; ed G Hermanson; Academic Press) and WO99/40214. Examples of the first category include but are not limited to SPDP (N-succinimidyl 3-(2-pyridyldithio) propionate), SMBP (succinimidyl-4-(p-maleimidophenyl) butyrate), SMPT (succinimidyloxycarbonyl-□-methyl-(□-2-pyridyldithio)toluene), MBS (m-maleimidobenzoyl-N-hydroxysuccinimide ester), SIAB (N-succinimidyl(4 iodoacetyl)aminobenzoate), GMBS (□-maleimidobutyryloxy)succinimide ester), SIAX (succinimidyl-6-iodoacetyl amino hexonate, SIAC (succinimidyl-4-iodoacetyl amino methyl), NPIA (p-nitrophenyl iodoacetate). The second category is useful to couple carbohydrate-containing molecules (e.g. env glycoproteins, antibodies) to sulfydryl-reactive groups. Examples include MPBH (4-(4-N maleimidophenyl)butyric acid hydrazide) and PDPH (4-(N-maleimidomethyl)cyclohexane-1-carboxyl-hydrazide($M_2C_2H$ and 3-2(2-pyridyldithio)proprionyl hydrazide). As an example of the third category, one may cite ASIB (1-(p azidosalicylamido)-4-(iodoacetamido)butyrate). Another alternative includes the thiol reactive reagents described in Frisch et al. (Bioconjugate Chem. 7 (1996) 180-186).

Coupling (iii) involves, e.g., amine groups of diacyl amines present in lipid structures that can participate in the carbodiimide reaction with carboxylate groups of the ligand moiety.

Coupling (iv) may-be performed, e.g., via imine formation followed by reduction using a cyanoborohydrate.

Coupling (vi) may involve, e.g., an NHS ester derivative of ligand moiety and poxvirus amine groups to produce stable amide bond linkages.

Another example uses a maleimide-sulfhydryl bond involving a sulfhydryl group and a sulfhydryl reactive group. For example SATA (N-succinimidyl S-acelythioacetate) can be used to introduce a sulfhydryl group whereas sulfo SMCC (sulfosuccinimidyl 4-(N-maleimidomethyl)cyclo hexane 1-carboxylate) can be used to introduce a maleimide group resulting in a covalent thioether bond.

Covalent coupling may also be performed using a polymer such as polyethylene glycol (PEG) or its derivatives. Preferably, the polymer has an average molecular weight comprised between 200 to 20000 Da. For example, tresyl-MPEG can be used to couple an amino group present on Lys residues (see for example WO99/40214). Other means to conjugate two partners via PEG are described in the literature (in Bioconjugate techniques (1996) 606-618; ed G Hermanson; Academic Press and Frisch et al. Bioconjugate Chem. 7 (1996) 180-186).

Non covalent coupling includes electrostatic interactions, for example between a cationic ligand moiety and a negatively charged poxvirus. Another alternative consists in using affinity components such as Protein A, biotin/avidin, antibodies, which are able to associate non covalently or by affinity both partners. For example, coupling between a peptide ligand moiety and a poxviral particle may use biotinylated antibodies directed against a surface-exposed epitope and streptavidin-labelled antibodies directed against the peptide ligand moiety according to the technique disclosed by Roux et al. (1989, Proc. Natl. Acad Sci USA 86, 9079). Bifunctional antibodies directed against each of the coupling partners are also suitable for this purpose.

Genetic coupling is intended for polypeptide and peptide ligand moieties. Advantageously, a nucleic acid encoding said ligand moiety is inserted in a nucleic acid sequence encoding a viral polypeptide localized at the surface of a poxviral particle. Said nucleic acid sequence encoding a viral polypeptide localized at the surface of a poxviral particle can be carried by the poxviral genome or by an independent vector (for expression in a suitable cell line).

Preferably, insertion of the nucleic acid encoding the ligand moiety is made in a suitable region of the poxviral genome so as to preserve integrity of the poxviral particle.

Preferably, the genetic coupling results in a chimeric polypeptide wherein the heterologous ligand polypeptide moiety in use in the present invention is incorporated in the surface-exposed viral polypeptide, resulting in a fusion between the ligand moiety and the viral polypeptide. The fusion of the ligand moiety can be made at any location of the surface-exposed viral polypeptide, i.e. at the N-terminus, the C-terminus or between two amino acid residues. Preferably, the insertion/fusion of the ligand moiety does not disrupt the open reading frame of the surface-exposed viral polypeptide. Optionally, at least a portion of the surface-exposed poxviral polypeptide can be removed and replaced by the heterologous ligand moiety in use in the present invention.

When the poxviral particle of the invention is an EEV, surface-exposed poxviral polypeptides suitable for the genetic coupling include but are not limited to the expression products of the B5R, A34R and HA genes. According to a preferred embodiment, the nucleotide sequence encoding the ligand moiety is fused with the B5R gene sequence so that said ligand moiety is finally located at the N-terminus of the corresponding expression product. Preferably, said ligand moiety encoding nucleotide sequence is fused immediately downstream of the B5R gene initiator codon. For indication, when the poxviral particle of the invention is an EEV vaccinia virus particle, the ligand moiety is not an antibody directed to ErbB-2.

When the poxviral particle of the invention is an IMV, surface-exposed viral polypeptides suitable for this genetic coupling include but are not limited to the expression products of the A27L (p14 protein), L1R, A14L, A17L (p21 protein), D8L, A9L, E10R and H3L genes (and as mentioned previously their equivalents of other poxviridae). According to a preferred embodiment, the nucleic acid encoding the ligand moiety is inserted in the p14 protein gene sequence (e.g. resulting in a fusion in frame to generate a p14-ligand fusion.) Preferably, the ligand moiety is fused to the N-terminus of the expression product of the A27L gene (or equivalent thereof), e.g. immediately downstream of the initiator codon of the p14 protein or a modified p14 protein (e.g. as defined hereinafter).

The term "poxviral p14 protein" as used herein refers to the structural protein present within a poxviral particle, and especially at the surface of an IMV particle, which is known to mediate the early virus-host cell interactions (e.g. binding to native cellular receptors). The p14 protein of the vaccinia virus Copenhagen genome is encoded by gene A27L and includes 110 amino acids (aa) (including the initiator Met residue, the sequence of which being disclosed for instance in Rodriguez et al. (1987, J. Virol. 61, 3550-3554) or in Genebank under accession number M35027. The MVA p14 protein sequence is encoded by the 138L gene (e.g. disclosed in Genebank under accession number U94848) is 110 amino acids long including the initiator Met residue.

The p14-encoding sequence can be isolated from a poxviral genome by conventional recombinant techniques. Anyone of the members of the poxviridae family such as those cited in connection with the term "poxviral particle" (e.g. vaccinia virus, avipoxvirus, cowpox, entomopox, monkey pox, swine pox or penguin pox) can be used as the source of the poxviral p14 protein (and its gene or its coding sequence). Preferably, however, the poxviral p14 protein originates (is obtained or isolated) from a vaccinia virus and especially a vaccinia virus of Copenhagen, Wyeth or Ankara modified (MVA) strain.

For illustrative purposes, the A27L gene is present at the right end of the Copenhagen genome positioned between the A26L and A28L genes, e.g. from nucleotide (nt) 139330 to nt 138998. In the MVA genome, it is present at the right end of the MVA genome positioned between 137L and 139L genes, e.g. from nucleotide (nt) 131298 to nt 130966. On the basis of the indications given in this application and the data available in the art, it is within the scope of the skilled person to adapt the present invention to other poxvirus p14 proteins (or functional equivalents thereof).

In a general manner, a wild-type poxviral p14 protein comprises different fonctional domains (see for example Vazquez et al., 1998, J. Virol. 72, 10126-10137; Vazquez and Esteban, 1999, J. Virol. 73, 9098-9109). As illustrated in FIG. 4, the domain responsible for the interaction with lipids or membranes in the Golgi stacks involved in EEV formation was found to be located at the p14 N-terminus. It has been attributed to residue 1 to approximately residue in position 29 in Copenhagen and MVA p14 proteins. The attachment domain responsible for virus-cell attachment (implicated in the interaction with heparan sulfate receptor) and the fusion domain (responsible for virus cell fusion) overlap partially each other, the attachment domain extends from approximately residue in position 21 to approximately residue in position 33 and the fusion domain being located between approximately residues 29 and 43 in Copenhagen and MVA p14 proteins. The oligomerization domain is a triple-stranded coiled coil structure responsible for trimer formation (extending from approximately residue in position 44 to approximately residue in position 72 in Copenhagen and MVA p14 proteins). Finally, the anchoring domain has been identified at the C-terminus (extending from approximately residue in position 77 to approximately residue in position 98 in Copenhagen and MVA p14 proteins). It is involved in the interaction with the p21kDa protein, and thus the anchorage of the p14 protein to the IMV envelope.

The present invention encompasses the insertion of the heterologous ligand moiety in the full length poxviral p14 protein (i.e. which is encoded by the complete coding sequence from the initiator ATG codon to the stop codon) as well as in a modified p14 protein (e.g. generated by mutation, internal deletion, or truncation) such as a modified poxviral p14 protein as described below.

According to the present invention, the ligand moiety and the poxviral particle may be further modified to improve or stabilize the coupling. In particular, the ligand moiety may present a spacer moiety (or linker) at one or both of its extremities to facilitate its accessibility towards the target cells. A person skilled in the art will be able to design suitable spacers in accordance with the invention. The present invention is, however, not limited by the form, size or number of spacer sequences employed. One or multiple copies of the spacer sequence of choice may be inserted between the heterologous ligand moiety and the poxviral polypeptide. The only requirement for the spacer sequence is that it functionally does not adversely interfere with the folding and/or functioning of the individual entities of the fusion protein. For example, a suitable spacer is 5 to 50 amino acid long and may comprise amino acids such as glycine, serine, threonine, asparagine, alanine and proline (see for example Wiederrecht et al., 1988, Cell 54, 841;

Dekker et al., 1993, Nature 362, 852; Sturm et al., 1988, Genes and Dev. 2, 1582; Aumailly et al., 1990 FEBS Lett. 262, 82).

Of course, the poxviral particle of the present invention can comprise more than one ligand moiety, each binding to the same or to a different anti-ligand. For example, a poxviral particle can comprise a first ligand moiety permitting affinity-based purification and a second ligand moiety for selective binding to the target cell (e.g. through binding to the corresponding cell surface anti-ligand). When more than one ligand moiety is contemplated, they may or may not be combined one to another, for example in a tandem structure. For example, when it is desirable to enhance the specificity of the poxviral particle towards a specific target cell, it may be advantageous to use a combination of ligand moieties capable of recognizing and binding this target cell. The various ligand moieties can be coupled to the same surface-exposed viral polypeptide or to different ones.

In accordance with the objectives pursued by the present invention, the ligand moiety that is genetically coupled to the viral polypeptide may comprise a signal peptide facilitating its insertion in the envelope of the poxviral particle. Although the use of an hydrophobic sequence allowing for membrane anchorage can be envisaged, it is preferable to use a signal peptide allowing translocation to the trans-Golgi network. Such a peptide can be isolated or identified from any protein naturally present in the Golgi compartment (see for example Mochamer et Rose, 1987, J. Cell Biol. 105, 1205-1214; Mochamer, 1993, Curr. Opin. Cell Biol. 5, 606-612; Muesch et al., 1990, Trends Biochem sci 15, 86-88). The signal peptide can include one or several modification(s) with respect to the native sequence provided that its function is not significantly altered. A preferred signal peptide in use in the present invention is derived from the human trans-Golgi network glycoprotein TGN51 (Kain et al., 1997, J. Biol. Chem. 273, 981-988). It is preferably incorporated by genetic coupling at the N-terminus of the ligand moiety.

In a preferred embodiment of the present invention, the poxviral particle of the invention is recombinant i.e. including at least one additional nucleic acid (i.e. nucleic acid of interest) that is not native (i.e. heterologous) to the viral genome. The additional nucleic acid can be e.g. a therapeutic gene and/or a gene encoding a selection marker. In accordance with the goals pursued by the invention, the nucleic acid of interest is placed under the control of the elements allowing its expression in an eukaryotic cells, preferably the target cell targeted by the ligand moiety. Thus, according to a particularly preferred embodiment, the poxviral particle of the present invention comprises a recombinant poxviral genome. However, it is also possible to use empty poxviral particles, or pseudo-poxviral particle, of the invention forming complexes with a plasmid encoding said nucleic acid of interest (such as disclosed in U.S. Pat. No. 5,928,944 and WO 9521259).

As used herein, the term "control elements" refers to any element that allows, contributes or modulates the functional regulation of the nucleic acid of interest to be expressed, including replication, duplication, transcription, splicing, translation, stability and/or transport of the nucleic acid or one of its derivative (i.e. mRNA) into the target cell or organism. In the context of the invention, this term encompasses promoters, enhancers and other expression control elements (e.g., polyadenylation signals and elements that affect mRNA stability). It will be appreciated by those skilled in the art that the choice of the appropriate control element(s) can depend on such factors as the choice of the particular nucleic acid to be expressed, the target cell, the level of expression desired, etc.

Suitable control elements for use in the present invention include promoters which direct constitutive expression in many types of cell and those which direct expression of the nucleic acid of interest only in certain cells (e.g., tissue-specific regulatory elements) or in response to specific events or exogenous factors (e.g. by temperature, nutrient additive, hormone or other ligand). Such promoters are widely described in literature and include without limitation viral promoters like RSV, MPSV, SV40, or CMV, vaccinia promoters, inducible promoters, etc. Preferred promoters are isolated from poxviruses e.g. 7.5K, H5R, TK, p28, p11 or K1L of vaccinia virus. Alternatively, one may use a synthetic promoter such as those described in Chakrabarti et al. (1997, Biotechniques 23, 1094-1097), Hammond et al. (1997, J. Virological Methods 66, 135-138) and Kumar and Boyle (1990, Virology 179, 151-158) as well as chimeric promoters between early and late poxviral promoters.

The nucleic acid of interest may further include additional control elements, such as intron sequences, targeting sequences, transport sequences, secretion signal, nuclear localization signal, IRES, poly A transcription termination sequences, tripartite leader sequences, sequences involved in replication or integration. Said sequences have been reported in the literature and can be readily obtained by those skilled in the art.

In a preferred embodiment, the nucleic acid of interest contains at least one therapeutic gene (i.e. encoding a gene product having therapeutic interest). A "therapeutic gene" is one which has a pharmacological or protective activity when administered appropriately to a patient, especially patient suffering from a disease or illness condition or who should be protected against this disease or condition. Such a pharmacological or protective activity is one which is expected to be related to a beneficial effect on the course or a symptom of said disease or said condition. When the skilled man selects in the course of the present invention a therapeutic gene, he generally relates his choice to results previously obtained and can reasonably expect, without undue experiment other than practicing the invention as claimed, to obtain such pharmacological property. According to the invention, the nucleic acid of interest can be homologous (i.e. native) or heterologous (i.e. non-native) to the target cells into which is contemplated by the present invention. Advantageously said nucleic acid of interest encodes all or part of a polypeptide, especially a therapeutic or prophylactic polypeptide giving a therapeutic or prophylactic property. A polypeptide is understood to be any translational product of a polynucleotide regardless of size, and whether glycosylated or not, and includes peptides and proteins. Therapeutic polypeptides include as a primary example those polypeptides that can compensate for defective or deficient proteins in an animal or human organism, or those that act through toxic effects to limit or remove harmful cells from the body. They can also be immunity conferring polypeptides which act to provoke a humoral or cellular response, or both.

Examples of polypeptides encoded by a therapeutic gene include genes coding for a cytokine (alpha, beta or gamma interferon, interleukin, in particular IL-2, IL-6, IL-10, IL-12, IL-15, IL-18 or IL-21), a combination of cytokines (especially the fusion of two cytokines such as IL-2 and IL-18, as described in the European application EP 03 360086.7), a tumor necrosis factor (TNF), a colony stimulating factor (GM-CSF, C-CSF, M-CSF . . . ), a immunostimulatory polypeptide (B7.1, B7.2 and the like), a coagulation factor (FVIII, FIX . . . ), a growth factor (Transforming Growth Factor TGF, Fibroblast Growth Factor FGF and the like), an enzyme (urease, renin, thrombin, metalloproteinase, nitric oxide synthase NOS, SOD, catalase . . . ), an enzyme inhibitor (alphal-antitrypsin, antithrombin III, viral protease inhibitor, plasminogen activator inhibitor PAI-1), the CFTR (Cystic Fibrosis Transmembrane Conductance Regulator) protein, insulin, dystrophin, a MHC antigen of class I or II, a polypeptide that can modulate/regulate expression of cellular genes, a polypeptide capable of inhibiting a bacterial, parasitic or viral infection or its development (antigenic polypeptides, antigenic epitopes, transdominant variants inhibiting the action of a native protein by competition . . . ), any immunogenic polypeptide to which an immune response is desired, an apoptosis inducer or inhibitor (Bax, Bcl2, BclX . . . ), a cytostatic agent (p21, p 16, Rb . . . ), an apolipoprotein (ApoAI, ApoAIV, ApoE . . . ), an inhibitor of angiogenesis (angiostatin, endostatin . . . ), an angiogenic polypeptide (family of Vascular Endothelial Growth Factors VEGF, FGF family, CCN family including CTGF, Cyr61 and Nov), an oxygen radical scaveyer, a polypeptide having an anti-tumor effect, an antibody, a toxin, an immunotoxin and a marker (beta-galactosidase, luciferase . . . ) or any other genes of interest that are recognized in the art as being useful for the treatment or prevention of a clinical condition.

In view of treating an hereditary dysfunction, one may use a functional allele of a defective gene, for example a gene encoding factor VIII ou IX in the context of haemophilia A or B, dystrophin (or minidystrophin) in the context of myopathies, insulin in the context of diabetes, CFTR in the context of cystic fibrosis.

When the poxviral particle of the present invention comprises a ligand aimed to target a tumor cell, the nucleic acid of interest preferably encodes an anti-tumor agent. A variety of anti-tumor agents may be utilized in accordance with the present invention. Representative examples of anti-tumor agents include immune activators and tumor proliferation inhibitors. Briefly, immune activators function by improving immune recognition of tumor-specific or tumor-associated antigens (e.g. through humoral and/or cellular-mediated immunity). As a result, the immune system will more effectively inhibit or kill tumor cells. Representative examples include immunogenic tumor-associated or tumor-specific antigens, immune modulators which act to improve the interaction between immune cells and tumor cell (e.g. CD3, ICAM-1, ICAM-2, LFA-1, LFA-3, beta.-2-microglobulin, chaperones, alpha interferon, B7.1, B7.2 and major histocompatibility complex (MHC)) and cytokines which act to improve proliferation, activation, or differentiation of immune effector cells (e.g. gamma interferon, tumor necrosis factor, IL-2, IL-6, IL-7, IL-10, IL-11, IL-12, IL-18, IL-21, GM-CSF, CSF-1, and G-CSF).

Tumor proliferation inhibitors act by directly inhibiting cell growth, or by directly killing the tumor cell. Representative examples of tumor proliferation inhibitors include toxins, antisense, tumor suppressor and suicide genes. Representative examples of toxins include without limitation ricin (Lamb et al., 1985, Eur. J. Biochem. 148, 265-270), diphtheria toxin (Tweten et al., 1985, J. Biol. Chem. 260, 10392-10394), cholera toxin (Mekalanos et al., 1983, Nature 306, 551-557; Sanchez and Holmgren, 1989, Proc. Natl. Acad. Sci. USA 86, 481-485), gelonin (Stirpe et al., 1980, J. Biol. Chem. 255, 6947-6953), pokeweed (Irvin, 1983, Pharmac. Ther. 21, 371-387), antiviral protein (Barbieri et al., 1982, Biochem. J. 203, 55-59; Irvin et al., 1980, Arch. Biochem. Biophys. 200, 418-425; Irvin, 1975, Arch. Biochem Biophys. 169, 522-528), tritin, Shigella toxin (Calderwood et al., 1987, Proc. Natl. Acad. Sci. USA 84, 4364-4368; Jackson et al., 1987, Microb. Path. 2, 147-153) and Pseudomonas exotoxin A (Carroll and Collier, 1987, J. Biol. Chem. 262, 8707-8711). Antisense sequences suitable for use in the present invention include those designed to inhibit tumor cell growth, e.g. by preventing the cellular synthesis of critical proteins needed for cell growth. Examples of such antisense sequences include antisense to positively-acting growth regulatory genes, such as oncogenes and protooncogenes (c-myc, c-fos, c-jun, c-myb, c-ras, Kc, JE, HER2), as well as antisense sequences which block any of the enzymes in the nucleotide biosynthetic pathway. Finally, examples of tumor suppressors include e.g. Rb, p53, DCC, NF-1, Wilm's tumor, NM23, BRUSH-1, p16, p21, p56, p73 as well as their repective mutants.

A suicide gene encodes an expression product able to transform an inactive substance (prodrug) into a cytotoxic substance, thereby giving rise to cell death. The gene encoding the TK HSV-1 constitutes the prototype of the suicide gene family (Caruso et al., 1993, Proc. Natl. Acad. Sci. USA 90, 7024-7028; Culver et al., 1992, Science 256, 1550-1552). While the TK polypeptide is non toxic as such, it catalyzes the transformation of nucleoside analogs (prodrug) such as acyclovir or ganciclovir. The transformed nucleosides are incorporated into the DNA chains which are in the process of elongation, cause interruption of said elongation and therefore inhibition of cell division. A large number of suicide gene/prodrug combinations are currently available. Those which may more specifically be mentioned are rat cytochrome p450 and cyclophosphophamide (Wei et al., 1994, Human Gene Ther. 5, 969-978), *Escherichia coli* (*E. coli*) purine nucleoside phosphorylase and 6-methylpurine deoxyribonucleoside (Sorscher et al., 1994, Gene Therapy 1, 223-238), *E. coli* guanine phosphoribosyl transferase and 6-thioxanthine (Mzoz et al., 1993, Human Gene Ther. 4, 589-595). However, in a more preferred embodiment, the poxviral particle of the invention comprises a suicide gene encoding a polypeptide having a cytosine deaminase (CDase) or a uracil phosphoribosyl transferase (UPRTase) activity or both CDase and UPRTase activities, which can be used with the prodrug 5-fluorocytosine (5-FC). The use of a combination of suicide genes, e.g. encoding polypeptides having CDase and UPRTase activities, can also be envisaged in the context of the invention.

CDase and UPRTase activities have been demonstrated in prokaryotes and lower eukaryotes, but are not present in mammals. CDase is normally involved in the pyrimidine metabolic pathway by which exogenous cytosine is transformed into uracil by means of a hydrolytic deamination, whereas UPRTase transforms uracile in UMP. However, CDase also deaminates an analog of cytosine, 5-FC, thereby forming 5-fluorouracil (5-FU), which is highly cytotoxic when it is converted into 5-fluoro-UMP (5-FUMP) by UPRTase action.

Suitable CDase encoding genes include but are not limited to the *Saccharomyces cerevisiae* FCY1 gene (Erbs et al., 1997, Curr. Genet. 31, 1-6; WO93/01281) and the *E. coli* codA gene (EP 402 108). Suitable UPRTase encoding genes include but are not limited to those from *E. coli* (upp gene; Anderson et al., 1992, Eur. J. Biochem. 204, 51-56), *Lactococcus lactis* (Martinussen and Hammer, 1994, J. Bacteriol. 176, 6457-6463), *Mycobacterium bovis* (Kim et al. 1997, Biochem Mol. Biol. Int 41, 1117-1124), *Bacillus subtilis* (Martinussen et al. 1995, J. Bacteriol. 177, 271-274) and *Saccharomyces cerevisiae* (FUR-1 gene; Kern et al., 1990, Gene 88, 149-157). Preferably, the CDase encoding gene is derived from the FCY1 gene and the UPRTase encoding gene is derived from the FUR-1 gene.

The present invention also encompasses the use of mutant suicide genes, modified by addition, deletion and/or substitution of one or several nucleotides providing that the cytotoxic activity of the gene product be preserved. A certain number of CDase and UPRTase mutants have been reported in the literature including a fusion protein which encodes a two domain enzyme possessing both CDase and UPRTase activities (WO96/16183) as well as a mutant of the UPRTase encoded by the FUR-1 gene having the first 35 residues deleted (mutant FCU-1 disclosed in WO99/54481).

As mentioned above, therapeutic genes is also to be understood to include antisense sequences and ribozyme encoding genes capable of binding and destroying the RNA of selected positively-acting growth regulatory genes, such as oncogenes and protooncogenes (c-myc, c-fos, c-jun, c-myb, c-ras, Kc and JE).

The nucleic acid of interest incorporated into the poxviral particle of the present invention may comprise one or more therapeutic gene(s). In this regard, the combination of a suicide gene and a cytokine gene (e.g. at least one of those cited above), an immune modulator-encoding gene (e.g. at least one of those cited above) or a chimiokine gene (e.g. MIP , RANTES, MCP 1, . . . ) may be advantageous in the context of the invention. The different gene expression may be controlled by a unique promoter (polycistronic cassette) or by independent promoters. Moreover, they may be inserted in a unique site or in various sites along the nucleic acid either in the same or opposite directions.

In the context of the invention, the nucleic acid of interest (e.g. encoding the therapeutic gene) is preferably inserted in the poxviral genome into a nonessential locus, in order that the recombinant poxvirus remains viable and infectious. Suitable nonessential regions include but are not limited to non-coding intergenic regions or any gene for which inactivation or deletion does not significantly impair viral growth, replication or infection. One may also envisage insertion in an essential viral locus provided that the defective fumction be supplied in trans during production of viral particles, for example by using an helper cell line carrying the complementing sequences corresponding to those deleted in the poxviral genome.

For example, when using the Copenhagen vaccinia virus, one will preferably select an insertion site localized within the thymidine kinase gene (tk) (Hruby et al., 1983, Proc. Natl. Acad. Sci USA 80, 3411-3415; Weir et al., 1983, J. Virol. 46, 530-537). However, other insertion sites are also appropriate, such as within the hemagglutinin gene (Guo et al., 1989, J. Virol. 63, 4189-4198), within the K1L locus, within the u gene (Zhou et al., 1990, J. Gen. Virol. 71, 2185-2190) or at the left end of the vaccinia virus genome where a variety of spontaneous or engineered deletions have been reported in the literature (Altenburger et al., 1989, Archives Virol. 105, 15-27; Moss et al. 1981, J. Virol. 40, 387-395; Panicali et al., 1981, J. Virol. 37, 1000-1010; Perkus et al, 1989, J. Virol. 63, 3829-3836; Perkus et al, 1990, Virol. 179, 276-286; Perkus et al, 1991, Virol. 180, 406-410).

When using MVA, one will preferably select an insertion site localized within anyone of the identified deletions I to VII , and preferably in deletion II or III (Meyer et al., 1991, J. Gen. Virol. 72, 1031-1038; Sutter et al., 1994, Vaccine 12, 1032-1040) as well as within the D4R locus.

When using fowlpox virus, although insertion within the thymidine kinase gene may be considered, the sequence of interest is preferably introduced into a non-coding intergenic region., e.g. the intergenic region situated between ORFs 7 and 9 of the 1.3 kb HindIII fragment of the fowlpox genome (see for example EP 314 569 and U.S. Pat. No. 5,180,675).

The insertion site within the poxviral genome of the nucleic acid encoding the ligand moiety genetically coupled to the surface-exposed viral polypeptide is preferably in replacement of the viral gene encoding the corresponding wild-type surface-exposed viral peptide. For example, the nucleic acid encoding the fusion ligand-p14 protein as described above is preferably inserted in the poxviral genome in replacement of the wild-type p14-encoding A27L gene (or a poxviral gene encoding a p14 functional equivalent).

The basic technique for inserting a given nucleic acid into a poxviral genome is described in numerous documents accessible to the man skilled in the art (Piccini et al., 1987, Methods of Enzymology 153, 545-563; U.S. Pat. Nos. 4,769,330; 4,772,848; 4,603,112; 5,100,587 and 5,179,993). This technique relates to homologous recombination events between the viral genome and overlapping sequences on both sides of the desired insertion site. One may use a "shuttle" plasmid containing the nucleic acid to be inserted (and the marker or indicator gene) flanked by appropriate poxviral sequences. Homologous recombination with the viral genome will result in integration of the nucleic acid into the poxviral genome. This recombination will occur in a eukaryotic host cell. Appropriate host cells for recombination are cells which are 1) infectable by poxvirus and 2) transfectable by the shuttle plasmid.

In an advantageous embodiment, the poxviral particle of the invention may be defective for one or more viral function. In the context of the present invention, it could be advantageous that the viral genome of the poxviral particle of the present invention be defective in at least one gene involved in the production of EEV particles. In one embodiment, it is defective in the F13L gene (encoding the p37 protein). It has been shown by Borrego et al. (1999, J. Gen. Virol. 80, 425-432) that the deletion of F13L gene results in a severe defect in the wrapping process of EEV, although normal levels of IMV are produced. Accordingly, by altering the poxviral F13L gene it is possible to increase IMV production. Said F13L gene may be altered by complete or partial deletion, mutation or insertion of any sequence within the coding sequence or the promoter. These techniques of gene alteration are well known in the art and are illustrated in Borrego et al. ,1999 (supra).

In another embodiment or optionally in combination with the alteration of the function of the F13L gene product, the poxviral particle of the present invention can lack a wild type p14 protein and comprise a poxviral p14 protein that has been modified e.g. the modified p14 protein of the invention as defmed below. Either the sequence encoding said modified p14 protein is inserted in the poxviral genome (e.g. in replacement of the wild-type A27L gene or at any suitable location) or is provided in trans (e.g. provided by a helper virus or through expression in a suitable cell line). Of course, the modified p14 protein can be homologous (from the same poxvirus) or heterologous (from another poxvirus strain) to the other components of the poxviral particle (e.g. the other capsid polypeptides and/or the viral genome).

The present invention also provides a modified poxviral p14 protein (or functional equivalent) comprising a modification of at least one amino acid residue within a region of said poxviral p14 protein which is normally (i.e. in a wild-type p14 protein) involved either in the interaction with one or more native cellular receptors, such as heparan sulfate or chondroitin sulfate receptor or in the formation of enveloped viral particles or in both functions. For example, one or more amino acids of the wild type p14 protein can be modified to render the modified p14 protein less able to bind said native cellular receptor(s), and especially cellular heparan sulfate, as compared to the corresponding wild type p14 protein. In combination, such a modification may also reduce the capability of the modified p14 protein to contribute to EEV formation.

Any amino acid residue(s) of the poxviral p14 protein involved in the attachment to the native cellular receptor(s) and/or in formation of enveloped viral particles is suitable for modification. Native amino acid residue to be modified can be selected by any method in the art. For example, the p14-encoding sequences from different poxviral strains (which are known in the art) can be compared to deduce conserved residues that are likely to mediate binding to native cellular receptors and/or those which are likely to contribute to EEV formation. Alternatively, or in combination, the p14 sequence can be mapped on three dimensional representation of the protein to deduce those residues which are most likely responsible for such function(s). These analysis can be aided by resorting to any common algorithm or program for deducing protein structural function interaction. Alternatively, random mutation can be introduced into a cloned poxviral p14 expression cassette (e.g. by site-directed mutagenesis, PCR amplification by varying the concentration of divalent cations in the PCR reaction, the error rate of the transcripts can be largely predetermined as described in Weiss et al., 1997, J. Virol. 71, 4385-4394 or Zhou et al., 1991, Nucleic Acid Res. 19, 6052). The nucleic acid encoding the modified p14 protein can be subcloned back in the template vector, thus generating a library of poxviral p14 proteins, some of which will harbor mutations which reduce or abolish binding to native cellular receptors such as cellular heparan sulfate-containing receptors, which reduce or abolish the formation of envelopped viral particles or which reduce or abolish both the binding to native cellular receptors and the formation of envelopped viral particles.

The amino acid residue(s) to be modified can be within a functional domain of the p14 protein as defined above or within a region connecting two domains. Such amino acid need not itself be the site of binding between the p14 protein and the native cellular receptor. For example, the native amino acid might be involved in a conformational change associated with receptor binding. However, advantageously, the amino acid(s) to be modified are located within the so-called "attachment domain" or can also be at its close proximity (within about 1 to 10 residues). The present invention encompasses the deletion of such one or more residues as well as a combination of substitution(s) and deletion(s) so as to ablate or at least substantially reduce binding of the modified p14 protein to the native cellular receptor(s). Preferably, the modified p14 protein of the invention lacks a significant portion or even all of its attachment domain. Alternatively, the amino acid(s) to be modified are located within the N-terminal domain involved in formation of envelopped viral particles or can also be at its close proximity (within about 1 to 10 residues). The present invention encompasses the deletion of such one or more residues as well as a combination of substitution(s) and deletion(s) so as to ablate or at least substantially reduce the involvement of the modified p14 protein in EEV formation. Preferably, the modified p14 protein of the invention lacks a significant portion or even all of the domain involved in EEV formation. "Significant" as used herein refers to a sizable number of amino acid residues constituting the domain in question, such as more than the half of the residues.

According to a preferred embodiment, the modified p14 protein of the invention lacks at least a significant portion of both the attachment domain and the domain involved in EEV formation. Suitable modifications include without limitation the deletion of the 32 first amino acid residues following the initiator Met residue (in position +1) (i.e. deletion ranging from positions 2 to 33 of the wild-type p14 protein), advantageously the 31 residues following the initiator Met residue (i.e. deletion ranging from positions 2 to 32 of the wild-type p14 protein), preferably the 30 residues following the initiator Met residue (i.e. deletion ranging from positions 2 to 31 of the wild-type p14 protein), more preferably the 29 residues following the initiator Met residue (i.e. deletion ranging from positions 2 to 30 of the wild-type p14 protein), and even more preferably the 29 residues following the initiator Met residue (i.e. deletion ranging from positions 2 to 30 of the wild-type p14 protein) or the 28 residues following the initiator Met residue (i.e. deletion ranging from positions 2 to 29 of the wild-type p14 protein) or even the 27 residues following the initiator Met residue (i.e. deletion ranging from positions 2 to 28 of the wild-type p14 protein). Most, preferably, the modified p14 protein of the invention comprises an amino acid sequence as shown in SEQ ID NO: 26 and may further include an initiator methionine if required.

The decrease or abolition of binding to the native cellular receptor, and in particular to the cellular heparan sulfate, can be evaluated by measuring infectivity or cell attachment provided by the modified p14 of the invention or virus particles harboring such a modified p14, using the technique in the art or as described in the Experimental Section of the present application. Monitoring can be performed by autoradiography (e.g. employing radioactive viruses or recombinantly produced radiolabeled p14 proteins), immunochemistry, by measuring plaque formation, cytotoxicity or by evaluating gene delivery (e.g. using a reporter gene). For instance, suitable techniques include infection experiments of suitable cells carried out in the presence and in the absence of a competitor (i.e. heparin in the context of heparan sulfate-containing receptors). For example, a poxviral particle deficient or altered for binding to the cellular heparan sulfate will be less or not competited by the competitor as compared to a wild-type poxvirus for infection of cells exhibiting heparan sulfate at their surface. Indeed, after incubation of poxvirus particles exhibiting a wild type p14 protein in the presence of heparin, the heparan sulfate-mediated pathway is inhibited due to the saturation of the native p14 with the competitor, whereas the infectivity of particles displaying a modified p14 impaired in heparan sulfate attachment is not substantially modified by the competitor. Alternatively, the ability of the modified p14 of the invention to bind heparan sulfate can also be assayed by the Biacore technique, using an appropriate substrate (e.g. heparin) immobilized on a support. It is also possible to evaluate infectivity after pretreatment of suitable cells by heparinase.

The ability of the modified p14 of the present invention to bind to native cellular receptor(s) (e.g. cellular heparan sulfate-containing receptors) is substantially decreased or abolished, when the residual infection of cells containing such receptors with a poxvirus particle bearing such a modified p14, is at least about 1.5 less than that observed with a poxvirus particle bearing the corresponding wild-type poxviral p14. Preferably, it is at least about 1.8, more preferably at least about 2, even more preferably at least about 2.5 less than that observed with the corresponding wild-type poxvirus particle.

The decrease or abolition of formation of enveloped viral particles can be evaluated by standard techniques, such as electronic microscopy.

In another embodiment, the modified p14 protein of the present invention retains its ability to trimerize (i.e. to form trimers when produced in eukaryotic cells). In this context, it is preferred that the oligomerization domain of the modified poxviral p14 protein of the invention be not modified appreciably or if modified, that the modification(s) introduced herein do not significantly alter the trimerization functions. As mentioned above, the oligomerization domain of the wild type vaccinia virus p14 consists essentially of the amino acid residues ranging from approximately position 44 to approximately position 72 (corresponding to the amino acid residues ranging from approximately position 15 to approximately position 43 of the polypeptide sequence shown in SEQ ID NO: 26).

Furthermore, it is also preferred that the modified poxviral p14 protein of the present invention retains its capacity to associate with a poxviral p21 kDa protein in order to be anchored at the surface of a poxviral particle, and particularly of an IMV particle. In this context, it is preferred that the anchoring domain of the modified p14 protein of the invention be not modified appreciably or if modified, the modification(s) introduced in this domain do not significantly alter its ability to interact with a poxviral p21kDa protein. As mentioned above, the anchoring domain of the wild type vaccinia virus p14 protein is located in the C-terminal portion of the p14 protein and consists essentially of the amino acid residues ranging from approximately position 77 to approximately position 98 (corresponding to the amino acid residues ranging from approximately position 48 to approximately position 69 of the polypeptide sequence shown in SEQ ID NO: 26).

Hence, the present invention also provides a composition of matter comprising the modified poxviral p14 protein of the present invention and a poxviral p21 kDa protein. Preferably, the poxviral p14 protein and the poxviral p21 kDa protein associate in the same manner as wild-type p14 and p21 proteins.

In addition, it is also preferred that the modified poxviral p14 protein of the invention retains its capacity to promote fusion with a cellular membrane, and thus promote viral entry into a permissive cell. Preferably, in the context of the present invention, the fusion domain is not modified appreciably or if modified, the modification(s) introduced in this domain do not significantly alter the fusion function with the cell membrane of a permissive cell. As mentioned above, the fusion domain of the wild type vaccinia virus p14 consists essentially of the amino acid residues ranging from approximately position 29 to approximately position 43 (corresponding to the amino acid residues ranging from approximately the first alanine residue to approximately position 14 of the polypeptide sequence shown in SEQ ID NO: 26).

The modified poxviral p14 protein of the invention can be produced by any suitable method. For example, it can be synthetized using standard direct peptide synthesis techniques (e.g. as summarized in Bodanszky, 1984, *Principle of Peptide Synthesis*; Springer-Verlag, Heidelberg), such as via solid-phase synthesis (e.g. Merrifield, 1963, J. Am. Chem. Soc. 85, 2149-2154 and Barany et al., 1987, Int. J. Peptide Protein Res. 30, 705-739). Alternatively, oligonucleotide site-specific mutagenesis procedures are also appropriate to introduce the desired mutation(s) following cloning the sequence encoding a wild-type poxviral p14 protein or peptide fragment into a vector (Bauer et al., 1985, Gene 37, 73 and Sculptor TM in vitro mutagenesis system, Amersham, Les Ullis France). Alternatively, site-specific mutation(s) can be introduced by PCR techniques. One engineered, the sequence encoding the modified poxviral p14 protein or peptide fragment thereof can be subcloned into an appropriate vector (e.g. expression vector or poxviral genome) using well known molecular techniques.

Of course, the modified poxviral p14 protein of the invention can be further modified in addition to the above-described modifications. For example, since the precited modification(s) may alter the native tropism (e.g. the interaction with the native cellular receptors), it may be advantageous to include into the modified poxviral p14 protein of the invention a heterologous ligand moiety as defined above, in order to allow preferential targeting to a desired target cell or cell population. As described above, the preferred site of insertion of the heterologous ligand moiety into the modified p14 protein of the invention is at the N-terminus of said modified p14 protein. A suitable spacer and/or a suitable signal peptide can also be included in the ligand-modified p14 construct as disclosed above in connection with the poxviral particle of the invention. The initiator methionine may be carried by the heterologous ligand moiety or the signal peptide if required.

The present invention also relates to a trimer comprising a modified poxviral p14 protein according to the invention. Preferably, the trimer of the invention comprises three modified poxviral p14 proteins.

Any suitable assay can be employed to evaluate the ability of the modified poxviral p14 protein of the invention to trimerize. For example, the modified poxviral p14 protein can be produced by standard recombinant techniques and this property can be tested on the recombinant product. Any appropriate cloning or expression vector and corresponding suitable host cells can be used in the context of the present invention, including but not limited to bacteria (e.g. *Escherichia coli*), yeast, mammalian or insect host cell systems and established cell lines.

Trimerization of the p14 protein can be evaluated using standard techniques such as those described in Lin et al. (2002, J. Biol. Chem. 277, 20949-20959) and Rodriguez et al. (1987, J. Virol. 61, 395-404). Determination can be performed on recombinant p14 protein, radiolabelled p14 protein (e.g. following incorporation of radioactive amino acids into the protein during synthesis). Suitable techniques include without limitation NMR spectroscopy, CD spectrometry and conventional electrophoresis techniques. For example, one can detect the difference in molecular weight of a trimer as opposed as a monomer. A boiled and denatured trimer will run at a lower molecular weight than a non-denatured stable trimer. Trimerization can also be assayed by using a monoclonal antibody recognizing only the trimeric form (e.g. via immunoprecipitation, Western blotting, etc.). Another evaluation of trimerization is the ability of the modified p14 protein to form a complex with the p21 protein, since only trimers can interact. This propensity can be assayed by co-immunoprecipitation, gel mobility-shift assays, SDS-PAGE, etc.

In another embodiment, the present invention further concerns a nucleic acid (e.g. an expression cassette or vector) encoding a fusion protein having the properties described herein and comprising an heterologous ligand moiety as described above and all or part of a viral polypeptide localized at the surface of a poxviral particle. Preferably, the part of the surface-exposed viral polypeptide is selected so as to allow exposition of the ligand moiety outside (accessibility to solvent for example).

The present invention also relates to a nucleic acid (e.g. an expression cassette or vector) encoding the modified poxviral p14 protein of the invention or a fragment thereof.

Any type of vector can be used in the context of the present invention, whether of plasmid or viral, integrating or nonintegrating origin. Such vectors are commercially available or described in the literature. Similarly, those skilled in the art are capable of adjusting the regulatory elements required for the expression of the nucleic acid of the invention. Preferred is the use of poxviral promoters such as those cited above in connection with the expression of the gene of interest or the poxviral promoter normally used to direct the expression of the viral gene encoding the corresponding wild-type surface-exposed viral peptide (e.g. the p14-encoding A27L gene). Preferably, said vector is a poxviral vector (e.g. genome) capable of being encapsidated under suitable conditions in a poxviral capsid to provide a poxviral particle bearing at its surface the fusion protein or the modified p14 protein expressed by the nucleic acid according to the present invention.

The present invention also provides a poxviral particle lacking a wild-type p14 protein and comprising the modified poxviral p14 protein, and especially the trimer of the invention. The poxviral particle comprising the modified p14 protein may have one or more of the embodiments described above in connection with the poxviral particle of the invention.

The modified poxviral p14 protein can be provided (e.g. expressed) from the poxviral genome itself (e.g. in replacement of the wild-type A27L gene or at any suitable location) or provided in trans by a complementation cell line. Preferably, the resulting poxviral particle has a reduced capacity to interact with the native cellular receptors, and especially the cellular heparan sulfate, as compared to a particle comprising a wild-type p14, due to the above-mentioned modification(s). The resulting poxvirus particle equiped with the modified p14 protein of the invention constitutes an appropriate substrate for coupling or inserting a heterologous ligand moiety, for targeting infection to a desired target cell or cell population. Alternatively or in addition, the ligand moiety can be also used to purify the virus, to inactivate the virus (e.g. by adsorbing it to a substrate for the ligand), or to grow the virus on cell lines having the anti-ligand recognized by said ligand. The present invention encompasses the case where the heterologous ligand moiety is inserted into or coupled to the modified poxviral p14 protein. Alternatively, it can also be inserted or coupled to any other surface-exposed viral polypeptides such as those mentionned above.

According to a preferred embodiment, the poxviral particle of the invention is a MVA particle comprising a MVA vector (e.g. genome) lacking the 138L gene encoding the wild-type p14 protein and containing in replacement a nucleic acid encoding the modified p14 protein of the invention. Said MVA vector can further comprise a nucleic acid of interest encoding a recombinant therapeutic gene (e.g. the FCU-1 gene) placed under the control of a vaccinia promoter (e.g. the p11K7.5 promoter) and inserted into deletion III of said MVA vector.

The present invention also provides an eukaryotic host cell comprising the poxviral particle, the modified poxviral p14 protein, the trimer or the nucleic acid of the present invention.

For the purpose of the invention, the term “host cells” should be understood broadly without any limitation concerning particular organization in tissue, organ, etc or isolated cells of a mammalian (preferably a human). Such cells may be unique type of cells or a group of different types of cells and encompass cultured cell lines, primary cells and proliferative cells from mammalian origin, with a special preference for human origin. Suitable host cells include but are not limited to hematopoïetic cells (totipotent, stem cells, leukocytes, lymphocytes, monocytes, macrophages, APC, dendritic cells , non-human cells and the like), pulmonary cells , tracheal cells, hepatic cells, epithelial cells, endothelial cells, muscle cells (e.g. skeletal muscle, cardiac muscle or smooth muscle), fibroblasts.

Moreover, according to a specific embodiment, the eukaryotic host cell of the invention can be further encapsulated. Cell encapsulation technology has been previously described (Tresco et al., 1992, ASAIO J. 38, 17-23; Aebischer et al., 1996, Human Gene Ther. 7, 851-860).

The present invention also provides a complementation cell line comprising a nucleic acid coding for a late poxviral polypeptide, and especially a polypeptide exposed at the surface of a native poxviral particle such as those cited above present at the surface of IMV and EEV poxviral particles. In the context of the present invention, the late poxviral polypeptide is a wild-type polypeptide or if modified, the modification(s) introduced herein do not significantly alter its function(s). Advantageously, said polypeptide is exposed at the surface of a native IMV particle. In a preferred embodiment, said IMV-exposed polypeptide is a poxviral p14 protein (or a functional equivalent thereof). Preferably, the p14 protein provided by the complementation cell line of the invention is a wild-type p14 protein or if modified, the modification(s) introduced herein do not significantly alter the p14 functions involved in the constitution of an IMV poxviral particle and infectivity, especially its ability to bind a native cellular receptor such a heparan sulfate-containing receptor, to trimerize and to associtae with a poxviral p21 protein.

A complementation cell line according to the present invention can be generated by conventional technology, e.g. by introducing an expression vector expressing the wild-type p14 protein in a parental cell line permissive for poxvirus infection. Any appropriate cell can be used in the context of the present invention, including but not limited to bacteria (e.g. *Escherichia coli*), yeast, mammalian or insect cell systems, with a special preference for established cell lines of avian origin. Methods of introducing a nucleic acid in a given cell line are well within the knowledge of the skilled artisan. Such techniques include microinjection of minute amounts of DNA into the nucleus of a cell (Capechi et al., 1980, Cell 22, 479-488), transfection for example with $CaPO_4$ (Chen and Okayama, 1987, Mol. Cell Biol. 7, 2745-2752), electroporation (Chu et al., 1987, Nucleic Acid Res. 15, 1311-1326), lipofection/liposome fusion (Felgner et al., 1987, Proc. Natl. Acad. Sci. USA 84, 7413-7417), particle bombardement (Yang et al., 1990, Proc. Natl. Acad. Sci. USA 87, 9568-9572), use of gene guns, infection, direct DNA injection (Acsadi et al., 1991, Nature 352, 815-818), and microprojectile bombardment (Williams et al., 1991, Proc. Natl. Acad. Sci. USA 88, 2726-2730). These techniques are also described in basic books such as Sambrook et al. (2001, Molecular Cloning: A Laboratory Manual, Cold Spring Harbor Laboratory Press, New York). A representative example of a cell line suitable for p14 complementation is the DF1 cell line, which is a spontaneously immortalized chicken cell line derived from 10 days old East Lansing Line (ELL-0) eggs (D. Foster, U.S. Pat. No. 5,672,485).

In the context of the invention, the nucleic acid encoding the late poxviral polypeptide to be complemented can be cloned into an appropriate vector and operably linked to suitable regulatory regions for controlling expression in the complementation cell line of the invention using well known molecular techniques (see for example Sambrook et al, 2001, "*Molecular Cloning. A Laboratory Manual*", Laboratory Press, Cold Spring Harbor N.Y.). The person of ordinary skill in the art would be aware of vectors suitable for maintenance, propagation or expression of the nucleic acid in the complementation cell line of the invention. Suitable expression vectors include without limitation pREP4, pCEP4 (Invitrogene), pCI (Promega), pCDM8 (Seed, 1987, Nature 329, 840) and pMT2PC (Kaufman et al., 1987, EMBO J. 6, 187-195). Moreover, the expression vector may also comprise a marker gene in order to select or to identify the transfected cells (e.g. by complementation of a cell auxotrophy or by antibiotic resistance), stabilising elements (e.g. cer sequence; Summers and Sherrat, 1984, Cell 36, 1097-1103), integrative elements (e.g. LTR viral sequences and transposons) as well as elements providing a self-replicating function and enabling the vector to be stably maintained in cells independently of the copy number of the vector in the cell. Markers include tetracycline or ampicillin-resistance genes for prokaryotic host cells and dihydrofolate reductase or neomycin resistance for eukaryotic host cells. However, any marker that provides selection for a phenotypic trait will be effective.

The complementation cell line of the invention can be cultured in dishes, plates, and flasks in the appropriate medium in accordance with standard cell culture protocols. As recognized by the skilled artisan, culture conditions will vary depending on the specific cell type, whether the cell is in suspension, adherent or in a co-culture with one or more cells.

The present invention also provides a poxvirus genome which is defective for the wild-type p14 protein. The p14-encoding wild-type gene can be inactivated for instance by insertional mutagenesis. Alternatively, the p14 gene encoding the wild-type p14 protein can be deleted of the poxviral genome either partially or in its entirety (e.g. resulting in a knock out p14 mutant as described in the Example 9). In the context of the invention, it can be replaced by at least one marker gene in order to select or to identify the particles comprising a deleted poxviral genome. Such marker genes include the *E. coli* gpt gene and the HSV-TK gene. Of course, the marker genes are placed under the control of suitable regulatory elements (e.g. the CMV promoter, or vaccinia promoters such as the early promoter 7.5K and early/late hybrid promoters). The present invention also encompasses a poxviral particle comprising the poxvirus genome defective for the wild-type p14 protein according to the invention.

The present invention further provides a process of producing a poxviral particle according to the invention, comprising the steps of:

a) obtaining a seed of said poxviral particle,
b) preparing a culture of permissive cells,
c) infecting said cell culture with said seed of poxviral particle,
d) culturing said infected cells for an appropriate period of time,
e) recovering the poxviral particles produced from the cell culture and/or the culture supernatant, and
f) optionally, purifying the recovered poxviral particles.

According to a special embodiment, it is possible to combine step a) and c). In this case, the process of the invention comprises the steps of:

a) preparing a culture of permissive cells,
b) infecting said cell culture with a wild type poxviral particle and transfecting said cell with a plasmid comprising a sequence of interest flanked by overlapping sequences capable of homologous recombination with the DNA genome of said poxvirus,
c) culturing said cells for an appropriate period of time,
d) recovering the poxviral particles produced from the cell culture and/or the culture supernatant, and
e) optionally, purifying the recovered poxviral particles.

The term "permissive cells" as used herein refers to any cell that can be productively infected and optionally transfected by the elements (poxvirus and plasmid) required to allow the propagation and the production of the poxviral particles of the invention. Examples of such cells are CV-1 cells (monkey kidney cells), HuTK-143 cells (human cells), and BSC40 (monkey). However, in a preferred embodiment, the "permissive cells" are avian cells (e.g. avian cell lines available in cell collections such as ATTC), and most preferably primary chicken embryo fibroblasts (CEF) prepared from chicken embryos obtained from fertilized eggs.

The "seed of poxviral particle" is obtained according to the usual techniques at the end of the homologous recombination events between a suitable poxviral genome and a suitable plasmid (e.g. incorporating the acid nucleic to be inserted).

The cells can be first infected with a poxvirus and then transfected with the shuttle vector. Viral infection is accomplished by standard techniques for infection of eukaryotic cells with poxvirus (see for instance Paoletti et al., supra). The cells can be transfected with the shuttle vector by any of the conventional techniques of transfection. These include the techniques of calcium phosphate precipitation, DEAE dextran, electroporation and protoplast fusion, optionally in combination with glycerol in order to facilitate the shuttle vector uptake. The preferred technique is the calcium phosphate precipitation technique. After infection and subsequent transfection, the cells are incubated under standard conditions and virus is allowed to replicate during which time in vivo recombination occurs between the homologous poxvirus sequences present in the shuttle vector and the poxvirus genome.

Recombinant viral progeny are then selected by any of several techniques. The presence of integrated nucleic acid can be detected by hybridization with a labeled DNA probe specific for the integrated DNA (e.g. nucleic acid encoding the modified poxviral p14 protein or the recombinant gene). Alternatively, virus harboring the integrated nucleic acid can be selected on the basis of inactivation of the viral gene into which the integrated nucleic acid was inserted. For example, if the insertion of the nucleic acid is designed into the thymidine kinase (TK) gene of a poxvirus, the resulting virus will be unable to express thymidine kinase (TK−) and can be selected on the basis of this phenotype. Preferred techniques for selection are based upon co-integration of a gene encoding a marker or indicator gene along with the integrated nucleic acid, as illustrated in the examples. Representative examples of indicator genes include the *E. coli* lacZ gene which encodes the enzyme beta-galactosidase, *E. coli* gpt gene and *Aequorea victoria* green fluorescent protein EGFP. Selection of recombinant viruses expressing b-galactosidase or green fluorescent protein EGFP can be done visually eventually by employing a chromogenic substrate. For example, b-galactosidase expressing recombinant viruses are detected as blue plaques in the presence of the substrate 5-bromo-4-chloro-3-indolyl-B-D-galactoside or other halogenated-indolyl-B-D-galactosides (BluoGal.TM). Selection of recombinant viruses expressing gpt gene can be done by using a selective culture medium containing a mixture of mycophenolic acid, xanthin and hypoxanthin in the culture step of the process of the invention.

While the viral particles can be recovered from the culture supernatant, they can also be recovered from the cells. One of the commonly used methods consists in lysing the cells by any means (chemical, freezing/thawing, osmotic shock, mechanic shock, sonication and the like). The poxviral particle of the invention can be isolated by consecutive rounds of plaque purification and then purified using the techniques of the art (chromatographic methods, ultracentrifugation on cesium chloride or sucrose gradient). Alternatively, the affinity between the ligand moiety displayed at the viral surface and its anti-ligand may be used for purifiying the poxviral particle of the present invention. For example, the purification may be performed by a) immobilizing the concerned anti-ligand onto a solid support, b) contacting the viral preparation with the immobilized anti-ligand for a sufficient period of time to allow specific binding between the anti-ligand and the ligand moiety, c) discarding the unbound material and d) eluting the bound material and e) recovering the eluted material. Such a purification can be advantageous to reduce an eventual contamination of the poxviral particles of the invention with wild type or helper poxviruses.

The process of the invention can be used to produce both IMV and EEV poxviral particles. According to a preferred embodiment of the invention, the process includes an supplemental step allowing breakage of the additional envelope of EEV and selective production of IMV. Preferably, said further step consists in a sonication step or solubilization step in a mild detergent (e.g. Brij-58).

According to a particular embodiment, isolation and especially propagation of a poxviral particle of the present invention can be performed on a cell line exhibiting at its surface the anti-ligand molecule recognized by the ligand moiety of the present invention. This allows to minimize possible contamination with the wild type genome. For example, a poxvirus particle having a ligand moiety specific for MUC-1 polypeptide is preferably propagated on MUC-1 expressing target cells. On the other hand, a poxvirus particle having a ligand moiety specific for GC-C receptor is preferably propagated on GC-C receptor expressing target cells. The construction of such cell lines expressing onto their surface an anti-ligand molecule is within the scope of a man skilled in the art.

According to another particular embodiment of the process according to the invention, where the poxviral genome of the particle is defective for one or more viral functions (e.g. defective in at least one gene or the portion thereof involved in the production of EEV particles) it may be advantageous to use helper cells providing in trans the defective function. In particular, poxviruses defective for function encoded by the F13L gene are preferably cultured on a cell line expressing the F13L expression product. Such a cell line can be generated by transfection of a appropriate vector expressing the F13L polypeptide as described in Borrego et al. (1999, J. Gen. Virol. 80, 425-432). Similarly, poxvirus particles defective for the wild-type p14 protein can be isolated, propagated and/or amplified using a cell line expressing the wild-type p14 protein, such as the complementation cell line of the invention.

The present invention also provides a process for producing a poxviral particle deficient for the function provided by a late poxviral polypeptide, especially a poxviral particle of the invention comprising a genome encoding a modified p14 protein. Such a process includes culture steps in different cells. Specifically, when poxviral particle of the invention lacks a wild-type p14 gene and contains in replacement a nucleic acid (e.g. poxviral vector or genome) encoding a modified p14 protein according to the invention, it could be advantageous to carry out at least the first steps of the production process in cells providing in trans a wild-type p14 protein. Indeed, propagation and amplification of these viruses in conventional permissive cells (e.g. CEFs) is often impaired due to their reduced capacity to bind to native cellular receptors. More specifically, the process encompassed by the present invention to produce such poxviral particles comprises the steps of:

a) preparing a culture of a first cell wherein said first cell is capable of providing a wild-type p14 protein;

b) infecting said first cell with a poxviral particle comprising a poxvirus genome which is defective for the wild-type p14 protein and transfecting in said first cell a shuttle plasmid comprising the nucleic acid encoding the modified p14 protein of the invention and homologous sequences flanking on both sides the desired insertion site in the poxvirus genome;

c) culturing said transfected or infected first cell for an appropriate period of time and under suitable conditions for producing poxviral particles comprising a poxviral genome comprising the nucleic acid encoding the modified p14 protein of the invention;

d) recovering the resulting poxviral particles from the cell culture and/or the culture supernatant of said first cell;

e) infecting a second cell with the recovered poxviral particles;

f) culturing said infected second cell for an appropriate period of time and under suitable conditions for producing poxviral particles;

g) recovering the resulting poxviral particles from the cell culture and/or the culture supernatant of said second cell, and h) optionally, purifying the recovered poxviral particles.

Alternatively to step b of the process, the production of the virus seed can be performed according to standard techniques (e.g. by one or more round of infection or transfection of the first cell line with a poxviral particle of the invention or its genome).

In one embodiment the first cell is a complementation cell line according to the invention, with a special preference for a complementation cell line encoding a wild-type p14 protein. In another embodiment, the poxviral particle for homologous recombination is a knock out p14 mutant comprising a poxvirus genome which is deleted for the wild-type p14 protein (e.g. as described in the Example 9). In another embodiment, the overlapping homologous sequences are present on both sides of the p14-encoding gene. In MVA, preferred homologous sequences are those flanking the 138L gene, the 137L gene on one side and the 139L gene on the other side).

Homologous recombination in the first cell will then result in the constitution of a poxviral genome encoding the modified p14 protein according to the invention in replacement of the native p14 gene. The poxviral genome encoding the modified p14 protein can be encapsided in viral capsid. The resulting particles recovered from the cell culture or the culture supernatant of the first cell will comprise (i) the poxviral genome encoding the modified p14 protein and (ii) a viral capsid equiped with wild-type p14 proteins.

In a second step, such resulting particles can be transferred and cultured in a second cell which does not express the wild-type p14 protein, so as to have production of the modified p14 protein of the invention expressed from the poxviral genome, constitution of capsids comprising said modified p14 protein and encapsidation of the poxviral genome into these capsids. Such a second cell line can be any permissive cell (e.g. from avian origin) as well as an anti-ligand expressing cell. The process of the invention allows to improve the production yield of poxviral particles displaying a reduced capacity to bind the native cellular receptor and to reduce the contamination by wild-type viruses.

The invention also relates to a composition comprising at least one poxviral particle and/or at least one nucleic acid according to the invention. In a special case, the composition comprises two or more poxviral particles, and/or two or more nucleic acids (e.g. poxviral genomes) of the invention, wherein they differ each from one another by (i) the nature of the heterologous ligand moiety and/or (ii) the nature of the additional nucleic acid (e.g. gene of interest) and/or (iii) the poxviral origin and/or (iv) the particle form (IMV/EEV). This composition can be in various forms, e.g. in solid, liquid, powder, aqueous, lyophilized form. In a preferred embodiment, this composition further comprises a pharmaceutically acceptable carrier, allowing its use in a method for the therapeutic treatment of humans or animals. In this particular case, the carrier is preferably a pharmaceutically suitable injectable carrier or diluent (for example, see Remington's Pharmaceutical Sciences, $16^{th}$ ed. 1980, Mack Publishing Co). Such carrier or diluent is pharmaceutically acceptable, i.e. is non-toxic to a recipient at the dosage and concentration employed. It is preferably isotonic, hypotonic or weakly hypertonic and has a relatively low ionic strength, such as provided by a sucrose solution. Furthermore, it may contain any relevant solvents, aqueous or partly aqueous liquid carriers comprising sterile, pyrogen-free water, dispersion media, coatings, and equivalents, or diluents (e.g. Tris-HCl, acetate, phosphate), emulsifiers, solubilizers or adjuvants. The pH of the pharmaceutical preparation is suitably adjusted and buffered in order to be useful in in vivo applications. It may be prepared either as a liquid solution or as a solid form (e.g. lyophilized) which can be suspended in a solution prior to administration. Representative examples of carriers or diluents for an injectable composition include water, isotonic saline solutions which are preferably buffered at a physiological pH (such as phosphate buffered saline or Tris buffered saline), mannitol, dextrose, glycerol and ethanol, as well as polypeptides or proteins such as human serum albumin. For example, such a composition may comprise 10 mg/ml mannitol, 1 mg/ml HSA, 20 mM Tris pH 7.2 and 150 mM NaCl.

A composition according to the invention may be manufactured in a conventional manner for local, systemic, oral, rectal or topical administration. Suitable routes of administration include but are not limited to intragastric, subcutaneous, aerosol, instillation, inhalation, intracardiac, intramuscular, intravenous, intraarterial, intraperitoneal, intratumoral, intranasal, intrapulmonary or intratracheal routes. The administration may take place in a single dose or a dose repeated one or several times after a certain time interval. The appropriate administration route and dosage vary in accordance with various parameters, for example, with the condition or disease involved, the need for prevention or therapy, the stage to which it has progressed and the therapeutic gene to be transferred. As an indication, the poxviral particles may be formulated in the form of doses of between $10^4$ and $10^{14}$ pfu (plaque forming units), advantageously between $10^5$ and $10^{13}$ pfu and preferably between $10^6$ and $10^{12}$ pfu. The titer may be determined by conventional techniques. The nucleic acid doses are preferably comprised between 0.01 and 10 mg/kg, more especially between 0.1 and 2 mg/kg.

In addition, a composition according to the present invention may include one or more stabilizing substance(s), such as lipids (e.g. cationic lipids, liposomes, lipids as described in WO98/44143), nuclease inhibitors, polymers, chelating agents in order to preserve its degradation within the animal/human body.

In another embodiment, the present invention provides the use of a poxviral particle, of a nucleic acid or a composition according to the invention, for the preparation of a drug intended for the treatment of human or animal organism by gene therapy. Within the scope of the present invention, "gene therapy" has to be understood as a method for introducing any therapeutic gene into a cell. Thus, it also includes immunotherapy that relates to the introduction of a potentially antigenic epitope into a cell to induce an immune response which can be cellular or humoral or both.

The use according to the invention is dependent upon the targeting properties of the ligand moiety displayed at the surface of the poxviral particle or expressed by the nucleic acid of the invention. Thus, a ligand moiety capable of recognizing and binding to a molecule present at the surface of a cell infected with a pathogenic agent (bacteria, virus or parasite) is appropriate for the treatment or prevention of any condition or disease caused by such an infection. A tumor targeting ligand moiety is more intended in the treatment or the prevention of a cancer. The term "cancer" encompasses any cancerous conditions including diffuse or localized tumors, metastasis, cancerous polyps and preneoplastic lesions (e.g. dysplasies) as well as diseases which result from unwanted cell proliferation. A variety of tumors may be selected for treatment in accordance with the methods described herein, either primary or metastatic tumors. Cancers which are contemplated in the context of the invention include without limitation glioblastoma, sarcoma, melanomas, mastocytoma, carcinomas (e.g. colorectal and renal cell carcinomas) as well as breast, prostate, testicular, ovarian, cervix (in particular, those induced by a papilloma virus), lung (e.g. lung carcinomas including large cell, small cell, squamous and adeno-carcinomas), kidney, bladder, liver, colon, rectum, pancreas, stomach, esophagus, larynx, brain, throat, skin, central nervous system, blood (lymphomas, leukemia, etc.), bone, etc cancers. One may cite more particularly cancers of breast, cervix (in particular, those induced by a papilloma virus), prostate, lung, bladder, liver, colorectal, pancreas, stomach, esophagus, larynx, central nervous system, blood (lymphomas, leukemia, etc.), melanomas and mastocytoma.

By way of illustration, a poxviral particle targeted to MUC-1-expressing cells (e.g. a poxviral particle of the invention exhibiting a SM3 scFv ligand moiety) is particularly preferred for the prevention or the treatment of MUC-1-associated cancers such as lung, breast, kidney and prostate cancers. A poxviral particle targeted to GC-C receptor-expressing cells (e.g. a poxviral particle of the invention exhibiting a Sta peptide ligand moiety) is particularly preferred for the prevention or the treatment of colorectal cancers and related metastasis developped in various organs. A poxviral particle targeted to HPV-infected cells is particularly suited for the prevention or the treatment of papillomavirus-associated lesions, such as cancerous and precancerous lesions of the cervix and vulve (e.g. cervical intra-epithelial neoplasia, vulvar intra-epithelial neoplasia and cervical cancer).

The composition of the invention may also be used for the prevention and treatment of other diseases, such as those affecting muscles, blood vessels (preferably arteries) and/or the cardiovascular system, including without limitation myocardial infarcts, ischemic diseases (peripheral, lower limb, cardiac ischemia and angina pectoris), artherosclerosis, hypertension, atherogenesis, intimal hyperplasia, (re) restenosis following angioplasty or stent placement, connective tissue disorders (e.g. rheumatoid arthritis), ocular diseases (e.g. diabetic retinopathy, macular degeneration, corneal graft rejection, neovascular glaucoma), cerebral vascular diseases, diabete-associated diseases, immune disorders (e.g. chronic inflammation or autoimmunity), neuro-degenerative diseases, Parkinson diseases and genetic diseases (muscular dystrophies such as Becker and Duchenne, hemophilias, Gaucher's disease, cystic fibrosis, etc. as listed above). Another application is to use the composition of the invention as in vivo expression system for disorders that involve the gene product to be secreted into the bloodstream, especially to restore protein deficiencies (e.g. hemophilia by expressing the appropriate coagulation factor, lysosomal storage diseases, anemias).

The invention further provides a method for the treatment of a human or animal organism, comprising administering to said organism a therapeutically effective amount of a poxviral particle, of a nucleic acid or of a composition according to the invention. A <<therapeutically effective amount>> is a dose sufficient to the alleviation of one or more symptoms normally associated with the disease or condition desired to be treated. When prophylactic use is concerned, this term means a dose sufficient to prevent or delay the establishment of a disease or condition.

The method of the present invention can be used for preventive purposes and for therapeutic applications relative to the diseases or conditions listed above. The present method is particularly useful to prevent establishment of tumors or to reverse existing tumors of any type, using an approach similar to that described herein. It is to be understood that the present method can be carried out by any of a variety of approaches. Advantageously, the poxviral particle, the nucleic acid or the composition of the invention can be administered directly in vivo by any conventional and physiologically acceptable administration route, for example by intratumoral injection into an accessible tumor, by injection into the vascular system using an appropriate catheter, into the lungs by means of an aerosol or instillation or by systemic administration. Systemic administration is preferred when the method is carried out to reach metastasis. For example, intravenous injection or injection into the portal vein of a poxviral particle of the invention exhibiting at its surface the Sta peptide ligand is particularly useful to treat colorectal cancers or associated metastasis developped in various organs such as liver. The ex vivo approach may also be adopted which consists in removing cells from a patient (bone marrow cells, peripheral blood lymphocytes, myoblasts and the like), introducing the poxviral particle, the nucleic acid or the composition of the invention in accordance with the techniques of the art and readministering them to the patient.

As discussed above, the method of the present invention is more intended for the treatment of cancers, to provide tumor inhibition growth or tumor regression. For example, tumor inhibition may be determined by measuring the actual tumor size over a period of time. More specifically, a variety of radiologic imaging methods (e.g., single photon and positron emission computerized tomography; see generally, "Nuclear Medicine in Clinical Oncology," Winkler, C. (ed.) Springer-Verlag, New York, 1986), may be utilized to estimate tumor size. Such methods may also utilize a variety of imaging agents, including for example, conventional imaging agents (e.g., Gallium-67 citrate), as well as specialized reagents for metabolite imaging, receptor imaging, or immunologic imaging (e.g., radiolabeled monoclonal antibody specific of tumor markers). In addition, non-radioactive methods such as ultrasound (see, "Ultrasonic Differential Diagnosis of Tumors", Kossoff and Fukuda, (eds.), Igaku-Shoin, New York, 1984), may also be utilized to estimate the size of a tumor.

In addition to the in vivo methods for determining tumor inhibition discussed above, a variety of in vitro methods may be utilized in order to predict in vivo tumor inhibition. Representative examples include lymphocyte mediated anti-tumor cytolytic activity determined for example, by a $^{51}Cr$ release assay, tumor dependent lymphocyte proliferation (Ioannides et al., 1991, J. Immunol. 146, 1700-1707), in vitro generation of tumor specific antibodies (Herlyn et al., 1984, J. Immunol. Meth. 73, 157-167, cell (e.g., CTL, helper T cell) or humoral (e.g., antibody) mediated inhibition of cell growth in vitro (Gazit et al., 1992, Cancer Immunol. Immunother 35, 135-144), and, for any of these assays, determination of cell precursor frequency (Vose, 1982, Int. J. Cancer 30, 135-142).

Alternatively, inhibition of tumor growth may be determined based upon a change in the presence of a tumor marker. Examples include prostate specific antigen ("PSA") for the detection of prostate cancer and Carcino-Embryonic Antigen ("CEA") for the detection of colorectal and certain breast cancers. For yet other types of cancers such as leukemia, inhibition of tumor growth may be determined based upon the decreased numbers of leukemic cells in a representative blood cell count.

In the case of in vivo treatment according to the invention, in order to improve the transfection rate, the patient may undergo a macrophage depletion treatment prior to administration of the pharmaceutical preparations described above. Such a technique is described in the literature (refer particularly to Van Rooijen et al., 1997, TibTech, 15, 178-184).

According to the preferred embodiment, when the method of the invention uses a recombinant poxviral particle presenting the characteristics of the invention and expressing a suicide gene, it can be advantageous to additionally administer a pharmaceutically acceptable quantity of a prodrug which is specific for the expressed suicide gene product. The two administrations can be made simultaneously or consecutively, but preferably the prodrug is administered after the poxviral particle of the invention. By way of illustration, it is possible to use a dose of prodrug from 50 to 500 mg/kg/day, a dose of 200 mg/kg/day being preferred. The prodrug is administered in accordance with standard practice. The oral route is preferred. It is possible to administer a single dose of prodrug or doses which are repeated for a time sufficiently long to enable the toxic metabolic to be produced within the host organism or the target cell. As mentioned above, the prodrug ganciclovir or acyclovir can be used in combination with TK HSV-1 gene product and 5-FC in combination with FCY1, FUR1 and/or FCU1 gene product.

To illustrate a method intended for tumor treatment, one may first administer a poxviral particle expressing a suicide gene and displaying at its surface a ligand moiety capable of recognizing and binding to a tumor antigen expressed by the tumoral cells. Once infected, the cancerous cells will express the suicide gene. Killing of the infected cells can be performed by administering the prodrug metabolized by the chosen suicide gene product. For instance, in individuals in whom prevention or reversal of MUC-1 positive breast cancer is desired, one may employ a poxviral particle expressing FCU-1 and harboring at its surface a SM3 scFv ligand capable of recognizing and binding to the MUC-1 tumor antigen. Killing of the MUC-1 positive infected cells may be achieved with further administration of the prodrug 5-FC.

In addition, one particular characteristic of the method of the invention is that the poxviral particle of the invention can be produced in vivo in the treated organism. With this respect, one may envisage to administer to the patient a replicative IMV poxviral particle (e.g. Copenhagen vaccinia virus) which does not exhibit at its surface the ligand moiety but contain a poxviral genome genetically engineered by insertion of a nucleic acid encoding such a ligand moiety in a sequence encoding a polypeptide localized at the surface of the EEV poxviral particle (e.g. the B5R gene). Accordingly, in this special embodiment, the recombinant poxviral genome is able to produce in vivo (i.e. after administration to the patient) EEV particles in accordance with the present invention while the administered IMV form still presents the wild type poxviral characteristics. Said administered IMV particles infecting the patient cells in a non-specific manner (non targeted cells), the viral genome will replicate in the host infected cells and release EEV particles capable of infecting only target cells.

Prevention or treatment of a disease or a condition can be carried out using the present method alone or, if desired, in conjunction with presently available methods (e.g. radiation, chemotherapy and surgery).

The infection specificity of the poxviral particles of the invention is actually related to the binding specificity of the ligand moiety localized onto their surface. Accordingly, said poxviral particles can be used in methods based on specific binding between a said ligand moiety and an anti-ligand molecule. Thus, the invention also relates to a method for detecting and/or separating and/or concentrating and/or purifying and/or assaying any anti-ligand molecule, or by extension any compound comprising such an anti-ligand molecule, present in a sample, in which a poxviral particles according to the invention (i.e. exhibiting at their surface an heterologous ligand moiety which is able to specifically bind to such a molecule) is used to form a binding complex with said anti-ligand molecule, or said compound, if they are present in the sample.

The invention also concerns a reagent for detecting and/or concentrating and/or separating and/or purifying and/or assaying in a sample any anti-ligand molecule, or by extension any compound including such an anti-ligand molecule, comprising a poxviral particle according to the present invention i.e. exhibiting at its surface an heterologous ligand moiety which is able to specifically bind to such a molecule or compound.

The invention relates in particular to a method for detecting and/or concentrating and/or separating and/or purifying and/or assaying any anti-ligand molecule, or by extension any compound comprising such an anti-ligand molecule in a sample, including the following steps: said sample is placed in contact with a reagent according to the invention under conditions permitting a binding reaction, then any binding complex formed is separated, possibly detected, and/or quantified.

More particularly, the present invention relates to a method for detecting and/or concentrating and/or separating and/or purifying and/or assaying any anti-ligand molecule, or by extension any compound comprising such an anti-ligand molecule, present in a sample, using a reagent according to the invention comprising the steps of:

a) immobilizing said reagent onto a solid support,
b) contacting said sample with said immobilized reagent for a sufficient time to allow specific binding of the anti-ligand molecule, or compound comprising the anti-ligand molecule, with the heterologous ligand moiety of said reagent,
c) discarding the unbound sample,
d) eluting the anti-ligand molecule, or compound comprising the anti-ligand molecule, retained in step b), and
e) analyzing said anti-ligand molecule, or compound comprising the anti-ligand molecule, eluted in step d).

The term “solid support” as used here is, without limitation, in the form of a microtitration slide, a foil, a column, a sheet, a cone, a well, a bead, or any other appropriate micro or macro-particulate substrate, and includes all materials on which viral particle of the invention can be immobilized. This may be synthetic materials which are chemically modified or otherwise, especially polysaccharides, such as cellulose materials, for example paper, cellulose derivatives such as nitrocellulose and cellulose acetate or dextran (BIAcore, Upsala, Sweden); polymers such as vinyl chloride, polyethylene, polystyrene, polyacrylate, or copolymers such as propylene and vinyl chloride polymer, vinyl chloride and vinyl acetate polymer; styrene-based copolymers; natural fibers such as cotton and synthetic fibers such as nylon.

Preferably, the “solid support” is a polystyrene polymer, a butadiene/styrene copolymer or a butadiene/styrene copolymer mixed with one or more polymers or copolymers chosen from polystyrene, styrene/acrylonitrile or styrene/methyl methacrylate copolymers, polypropylenes, polycarbonates and the like.

The reagent (i.e. comprising the viral particles of the invention) can be attached to the solid support directly or indirectly.

Using the direct manner, two approaches are possible: either by adsorption of the reagent onto the solid support, that is to say by noncovalent bonds (principally of the hydrogen, Van der Walls or ionic type), or by formation of covalent bonds between the reagent and the support. Indirectly, it is possible to pre-attach an “anti-reagent” compound (by adsorption or covalence) to the substrate, said compound being able to interact with the reagent such as to immobilize the system on the solid substrate. By way of example, there may be mentioned an antibody, on the condition that it is immunologically reactive with a portion of the poxviral particles different from that involved in the binding with anti-ligand molecules; a ligand-receptor system, for example by grafting onto the poxviral particles a molecule such as a vitamin, and by immobilizing onto the solid phase the corresponding receptor (for example the biotin-streptavidin system). Indirect manner is also understood to mean the preliminary grafting or fusion by genetic coupling of a protein, or a fragment of this protein, or of a polypeptide, to one end of the poxviral particle proteins, and the immobilization of the latter onto the solid support by passive adsorption or covalent bonding of the protein or of the polypeptide grafted or fused.

In the context of the process of the present invention, the term "anti-ligand molecule, or by extension any compound comprising such an anti-ligand molecule" is used broadly to designate an organic chemical such as a drug or a polypeptide which may be contained in a sample or any target cells as previously defined, and more particularly tumoral cells. For example, it can designate a non-naturally occurring molecule which can be produced as a result of in vitro or synthetic method. It can be a naturally occurring molecule present in a cellular or biological sample (cultured cells, cell, organs or tissue biopsie, body fluids and the like), such as antibodies, cellular receptors, viral receptors and tumoral markers. If desired the sample can be processed using a method such as HPLC, which can provide a fraction enriched in molecules having a defined range of molecular weight, hydrophilic characteristics or the like. Conditions of enrichment can be defined by the person skilled in the art depending on the chemistry of the particular molecule and the technique.

The elution step can be performed by using any techniques permitting to separate bound ligand moiety/anti-ligand molecule. These techniques are well described in literature and are based on physico-chemical properties of said binding. For example, it is possible to vary pH or ionic strength conditions. It is further possible to use eluting compound capable of competing with the specific binding of the ligand and the molecule.

Another object of the invention is a kit for detecting the anti-ligand molecule, or by extension any compound comprising such an anti-ligand molecule (e.g. tumoral cells), including the reagent described above, attached to a solid substrate that is compatible (i.e. does not prevent binding of the ligand moiety with anti-ligand molecule) with said reagent.

Finally, the poxviral particles according to the instant invention, may be identified by using the following process. First, a poxviral particle library is provided. Said poxviral particle library is designed for cloning random polypeptide ligand moieties and expressing them in the correct folding at the poxviral surface. As used herein, the term "library" means a collection of poxviral particles exhibiting at their surface a few or a large number of different ligand moieties, varying from about ten to several billions. Preferably, the ligand moiety is a single chain fragment of an antibody or a peptide. A poxviral particle library expressing diverse populations of ligands at the viral surface can be prepared as described for phage display library (WO97/10507) or vaccinia direct ligation vectors (Merchlinsky et al., 1997, Virol 238, 444-451). Alternatively, one may use nucleic acid sequences from expression libraries (genomic fragments, cDNA from selected organs and tissues) or random libraries expressing peptide motifs. Such librairies are described in the literature or commercially available (Invitrogene, USA reference K1125-01; Clontech Laboratories Inc reference NL4000AA).

Preferably, as described above, the nucleic acid sequence encoding the polypeptide ligand moiety is cloned into an appropriate poxviral gene encoding a protein naturally localized onto the surface of the poxviral particle. In a preferred embodiment, the polypeptide ligand moiety is expressed as a fusion protein with one of the IMV or EEV surface polypeptides. In a more preferred embodiment, the polypeptide ligand moiety is fused in frame at the N-terminus of either the p14 protein present onto the IMV surface or the B5R gene product present onto the EEV surface.

Then, said poxviral particle library is placed in contact with an immobilized reagent consisting in identified anti-ligand molecule, or by extension identified compound comprising such an anti-ligand molecule (e.g. tumoral cells expressing MUC1). The contact is made during a sufficient period of time to allow the specific binding of the ligand moiety present at the surface of the poxviral particle library with the identified anti-ligand molecule present in the immobilized reagent. Specific binding can be enhanced by appropriate pH and osmolarity conditions. Preferably, the poxviral particle library is placed in a buffering solution having a pH comprised between approximately 6 and approximately 9.5 and, more preferably, between approximately 7 and approximately 8.5. In addition, various methods can be useful for preventing non-specific binding, for example by performing a preadsoption step using a any agent useful for blocking non-specific binding (e.g. serum albumin, dextran sulfate and the like) prior to the contacting step.

The unbound particles are eliminated and the bound particles are eluted. Reagent immobilisation and elution conditions are performed as described above. The poxviral particles from the library which have been retained by binding on the immobilized reagent are then analyzed. More particularly, said analysis is carried out by sequence determination of the ligand moiety encoding nucleic acid inserted in the genome of the isolated poxviral particles. The binding specificity of the ligand moiety identified within this process can be easily confirmed (i) by using target cells and non target cells, and controlling infectious property of the poxviral particles presenting said ligand moiety in accordance with the methods disclosed in the Experimental section or (ii) by preparing a reagent according to the invention, immobilizing it onto a solid support and implementing a method for assaying target cells and non target cells as described above.

These and other embodiments are disclosed or are obvious from and encompassed by the description and examples of the present invention. Further literature concerning any one of the methods, uses and compounds to be employed in accordance with the present invention may be retrieved from public libraries, using for example electronic devices. For example, the public database "Medline" may be used which is available on Internet, e.g. under http://www.ncbi.nlm.nih.gov/PubMed/medline.html. Further databases and addresses, such as http://www.ncbi.nlm.nih.gov, http://www.infobiogen.fr, http://www.fmi.ch/biology/research_tools.html, http://www.tigr.org, are known to the person skilled in the art and can also be obtained using, e.g., http://www.lycos.com. An overview of patent information in biotechnology and a survey of relevant sources of patent information useful for retrospective searching and for current awareness is given in Berks, TIBTECH 12 (1994), 352-364.

The present invention also concerns a method for the purification of a poxviral particle of the invention from a viral preparation containing both the poxviral particle of the invention and a wild type poxviral particle, comprising the steps of binding said viral preparation to a solid support coated with an anti-ligand molecule capable of binding said heterologous ligand moiety and recovering said poxviral particle. Preferably, the binding step is performed by surface plasmon resonance, preferably using a BIAcore X™ biosensor system (BIAcore AB, Uppsala, Sweden) according to the instructions of the manufacturer. According to a preferred embodiment, steptavidine is covalently bound to the solid support of a SA sensor chip by amine coupling using the amine coupling kit (BIAcore AB, Uppsala, Sweden). Then, biotinylated anti-ligand molecule is immobilized in flow cell on the SA sensor chip coated with steptavidine.

Flow cell 1 served as reference. Binding of fluid phase poxviral particles of the invention was determined over a range of $1\times10^4$-$1\times10^{10}$ pfu/ml. Injection volumes are comprised between 5 to 100 µl and flow rate comprised between 2 and 10 µl/min. The surface is regenerated with NaOH (2 to 50 mM) for recovery of specific targeted particles. Preferably, the solid support is a dextran support. Preferably, the anti-ligand molecule is a MUC-1-derived peptide, and especially a 60 mer representing 3 tandem repeats of MUC-1.

The method of the invention further comprises the step of infecting a permissive cell with said recovered poxviral particle. This step is performed according to standard technology. Preferably, the infection step is performed in the presence of EDTA (0.1 to 10 mM with a preference for 1 mM).

Finally, the present invention also relates to the use of a modified poxviral p14 protein of the invention, of a trimer therof having the above-defined characteristics, to substantially reduce the attachment of a poxviral particle comprising it to at least one native cellular receptor, and especially to cellular heparan sulfate. Preferably, said modified poxviral p14 protein or trimer therof has an affinity for said natural cellular receptor of at least about 1.5 fold less as compared to the corresponding wild type poxviral p14 protein or trimer. When said modified poxviral p14 protein or poxviral particle is modifed so as to comprise a ligand moiety, the present invention also provides the use of the above-cited elements for allowing or improving infection to a desired target cell or cell population displaying or expressing the corresponding anti-ligand. This approach is of particular importance for example in cancers. Thus, targeting may improve gene therapy procedures by restricting the viral tropism to specific tissue(s) of interest (e.g. cancer cells and not healthy tissue) or by improving accessibility to metastasis.

The invention has been described in an illustrative manner, and it is to be understood that the terminology which has been used is intended to be in the nature of words of description rather than of limitation. Obviously, many modifications and variations of the present invention are possible in light of the above teachings. It is therefore to be understood that within the scope of the appended claims, the invention may be practiced different from what is specifically described herein.

All of the above cited disclosures of patents, publications and database entries are specifically incorporated herein by reference in their entirety to the same extent as if each such individual patent, publication or entry were specifically and individually indicated to be incorporated by reference.

LEGENDS OF THE FIGURES

FIG. 1 illustrates the poxviral particle organization. The IMV envelope is represented with a fine line displaying at its surface the D8L gene product and the complex of p21-kDa (p21) and p14-kDa protein (p14). The EEV envelope is represented with a bold line displaying at its surface the A34R, HA and B5R gene products.

FIG. 4 is a schematic representation of functional domains in the A27L gene-encoded P14 protein (from Vazquez and Esteban, 1999, J. Virol. 73, 9098-9109)

Figure 5:
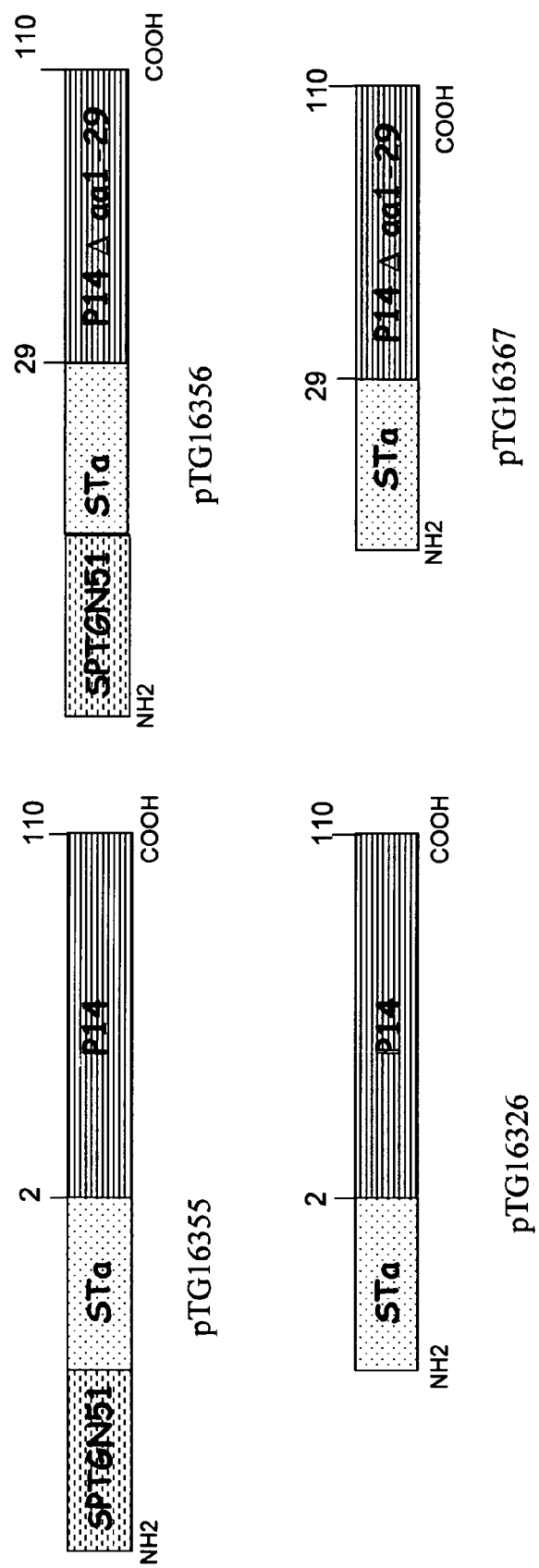

FIG. 5 is a schematic representation of the four different p14 constructions engineered to target MVA particles to GC-C receptor-positive tumor cells. SPTGN51 represents the signal peptide of the human trans-golgi network glycoprotein TGN51 including an initiator Met residue, Sta represents the Sta peptide as shown in SEQ ID NO: 24, p14 represents the full length MVA p14 protein (110 amino acid residues) and p14 delta aa 1-29 represents a modified p14 protein lacking amino acids 1 to 29 as compared to the corresponding wild-type MVA p14.

Figure 6:
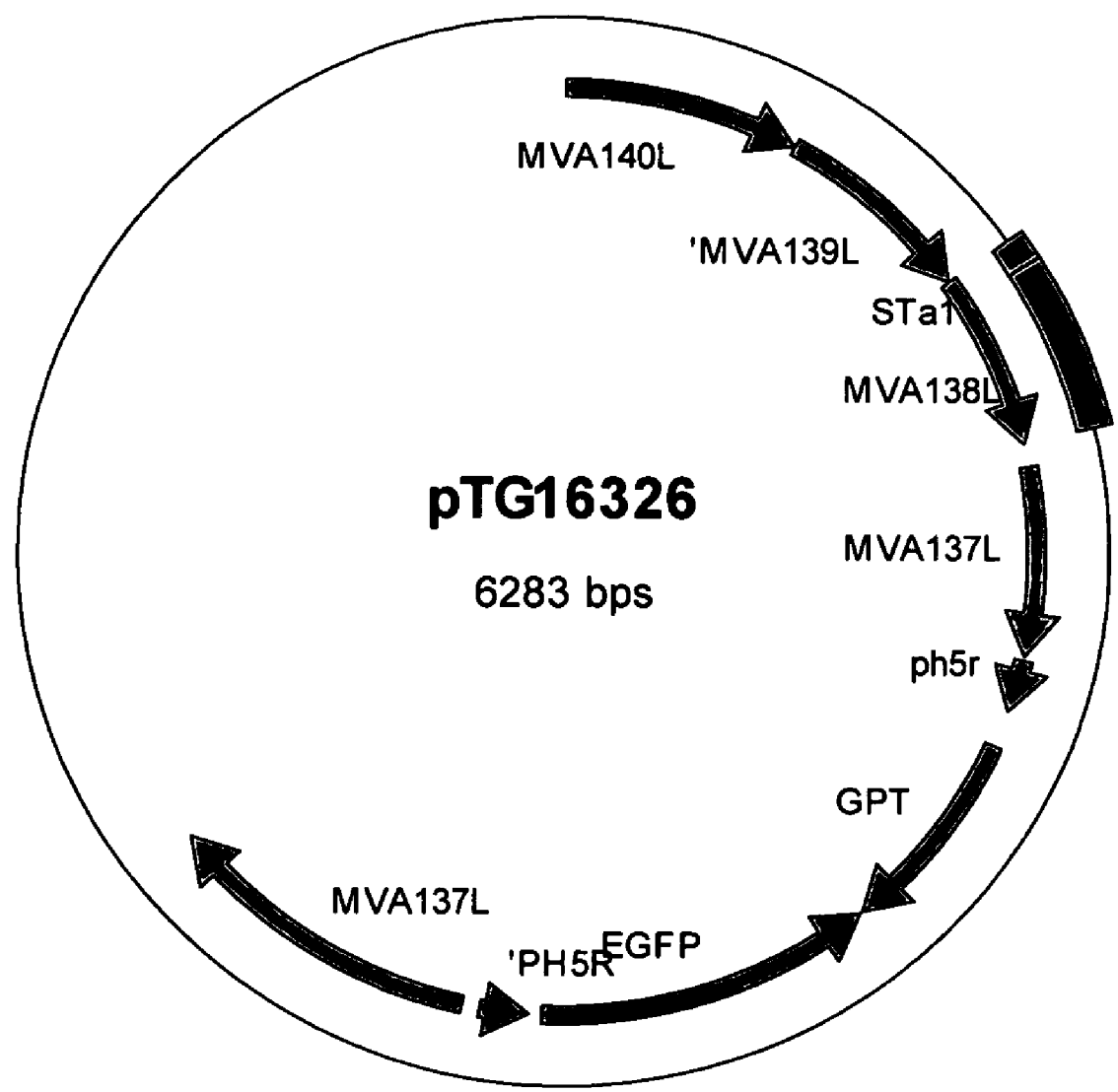

FIG. 6 represents schematically the plasmid pTG16326

The following examples serve to illustrate the present invention.

EXAMPLES

The constructions described below are carried out according to the general genetic engineered and molecular cloning techniques detailed in Maniatis et al. (1989, Laboratory Manual, Cold Spring Harbor Laboratory Press, Cold Spring Harbor N.Y.) or according to the manufacturer's recommendations when a commercial kit is used. PCR amplification techniques are known to the person skilled in the art (see for example PCR protocols—A guide to methods and applications, 1990, published by Innis, Gelfand, Sninsky and White, Academic Press).

The recombinant M13 bacteriophages are growth on the *E. coli* NM522 strain (Stratagen) in an agar-based minimal medium or in a liquid rich LBM medium. The recombinant plasmids carrying the ampicillin resistance gene are replicated in the *E. coli* C600 (Stratagene), BJ5183 (Hanahan, 1983, J. Mol. Biol. 166, 557-580) and NM522 on agar or liquid medium supplemented with 100 µg/ml of antibiotic. The BJ5183 strain is preferably used when the cloning is carried out by homologous recombination (Bubek et al., 1993, Nucleic acid Res. 21, 3601-3602).

The constructions of the recombinant vaccinia viruses are performed according to the conventional technology in the field in the documents above cited and in Mackett et al. (1982, Proc. Natl. Acad. Sci. USA 79, 7415-7419) and Mackett et al. (1984, J. Virol. 49, 857-864). The selection gene gpt (xanthine guanine phosphoribosyltransferase) of *E. coli* (Falkner and Moss, 1988, J. Virol. 62, 1849-1854) is used to faciliate the selection of the recombinant vaccinia viruses.

Example 1

Construction of a MVA Targeting MUC1 Positive Cells

Two different constructions have been engineered:

MVATG14519 is a MVA vector engineered to target MUC-1 positive tumor-cells that expresses a chimeric p14 protein in which the scFv chain of SM3 monoclonal antibody is fused in its native form to the N-terminus of the MVA 138L ORF (p14-kDa).

MVATG14552 (FIG. 2) is a MVA vector engineered to target MUC-1 positive tumor-cells and which is similar to MVATG14519 vector with the exception of the presence of a signal peptide of the human trans-golgi network glycoprotein TGN51 (sequence described by Kain et al., 1997, J. Biol. Chem 273, 981-988) fused at the N-terminus of the scFv chain of SM3 monoclonal antibody.

A. MVA138L Gene Modification.

A cloning vector for the insertion of scFv sequences has been assembled using a PCR based strategy. The 3' end of MVA138L gene and 3' flanking region are amplified using the primers OTG12340 (SEQ ID NO: 1) and OTG12343 (SEQ ID NO: 2) to produce fragment C. The selection marker expression cassette coding for the *E. coli* gpt placed under the control of the early-late promoter pH5R (Goebel et al., 1990, Virol 179, 247-266, 517-563) is isolated by PCR from a prior art plasmid DNA, such as pH5R-GPT (FR 98 13279) (designated hereinafter pTG9996), using the primers OTG12342 (SEQ ID NO: 3) and OTG12341 (SEQ ID NO: 4) to produce fragment E. The fusion between fragments C and E is performed by PCR by mixing both fragments and the primers OTG12340 and 12342 (Fragment F).

The upstream region of MVA138L is amplified with the tandem primer OTG12338 (SEQ ID NO: 5) and OTG12359 (SEQ ID NO: 6) in the case where the scFv is fused to the native p14-kDa to generate fragment A which is subsequently cloned between EcoRI and HindIII sites of M13TG6131 (Example 7 of WO99/03885) to give rise to M13TG14025. In the case where the scFv is fused at its N-terminus to the trans-golgi network glycoprotein TGN51 translocation signal, the amplification is performed with the primers OTG12338 (SEQ ID NO: 5) and OTG12346 (SEQ ID NO: 7). The resulting fragment (Fragment Asp) is cloned between EcoRI and HindIII sites of M13TG6131, to give M13TG14027. Both constructions include a unique HindIII site upstream the MVA138L coding sequence.

The MVA138L and the downstream region of MVA138L are amplified using the primers OTG12380 (SEQ ID NO: 8) and OTG12339 (SEQ ID NO: 9). The resulting fragment (fragment D) is cloned between EcoRI and HindIII sites of M13TG6131, to give M13TG14026. Fragments A/D or Asp/D are isolated by digestion with HindIII and EcoRI and inserted in the EcoRI site of the vector pTG1E (Example 2 of WO99/03885), to give respectively pTG14359 (containing the A/D fragment) and pTG14358 (containing the Asp/D fragment). Fragment F is then inserted either within pTG14359 or pTG14358 at the PacI site. Final constructs are named pTG14366 and pTG14365.

B. Isolation of SM3 scFv.

Figure 1:
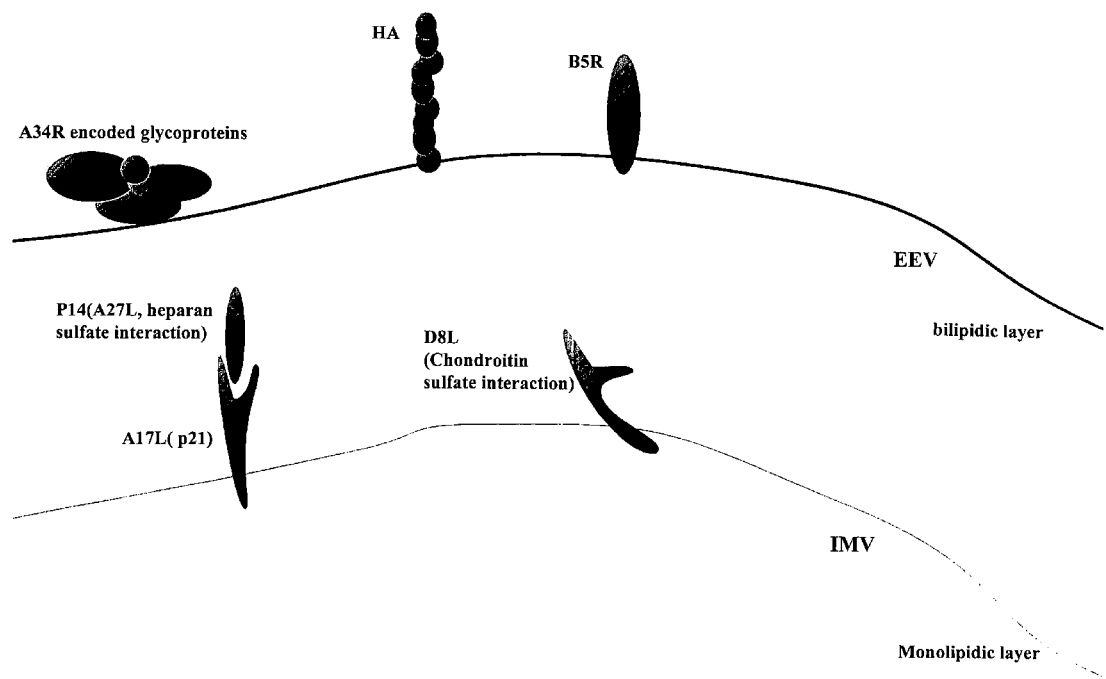
Figure 2:
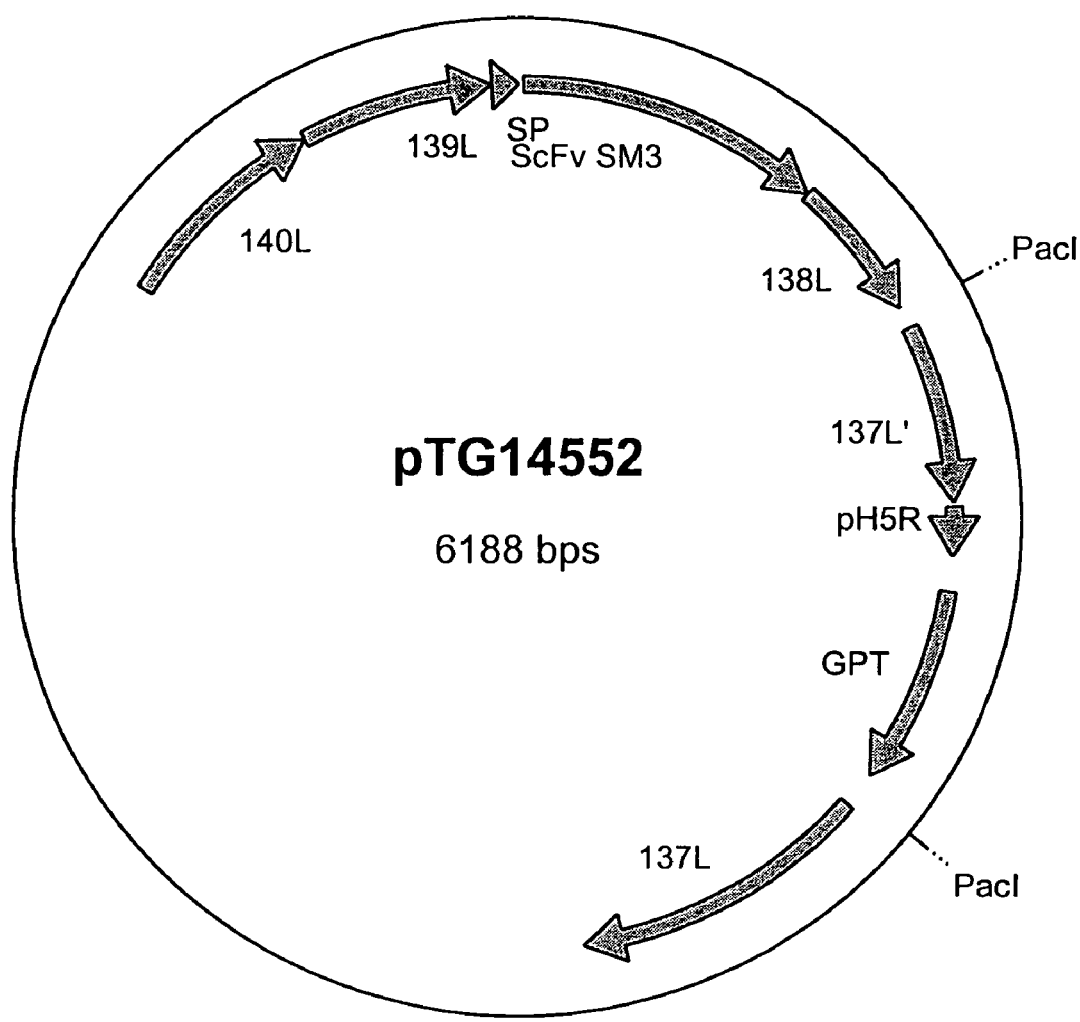
FIG. 2 represents schematically the plasmid pTG14552
Figure 3:
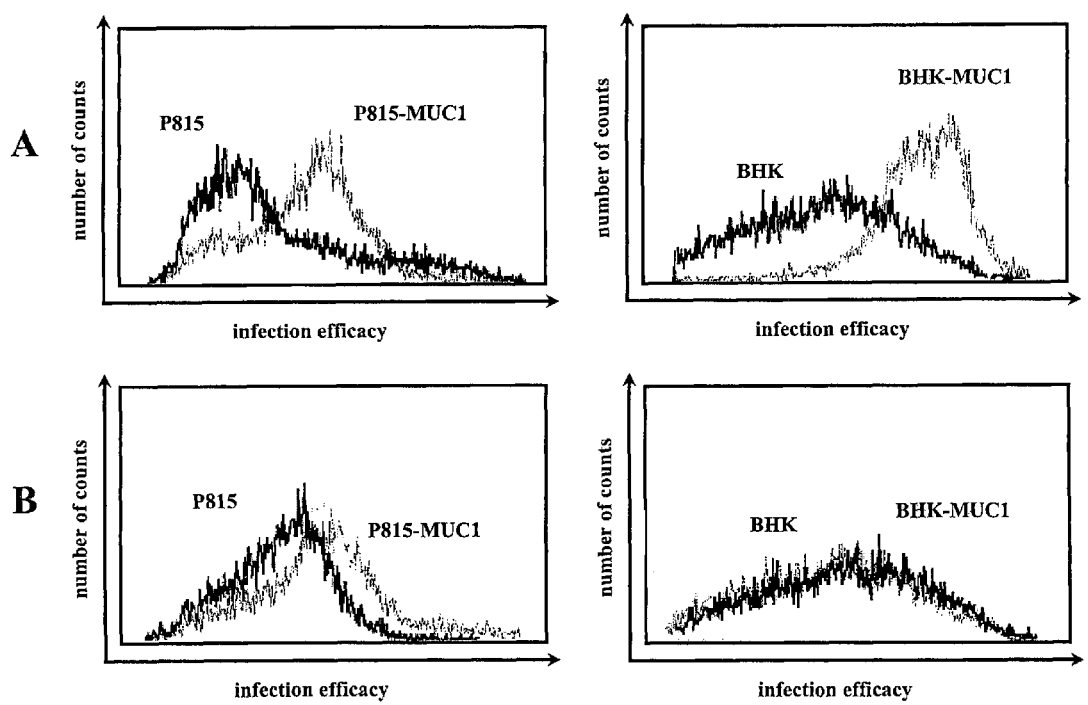
FIG. 3 represents a flow cytometry analysis following infection of P815, MUC-1 expressing P815 (P815-MUC1), BHK-21 and MUC-1 expressing BHK-21 (BHK-21-MUC1) by MVATG14552 (A) or the control MVAN33 (B).

The SM3 hybridoma has been described by Burschell et al. (1987, Cancer Res 47, 5476-5482), Girling et al. (1989, Int J Cancer 43, 1072-1076) and Dokurno et al. (1998, J. Mol. Biol. 284, 713-728). The epitope recognized onto the MUC-1 tumor associated form is P-D-T-R-P. SM3 scFv comprises the variable region of the SM3 antibody heavy chain (referred within the GeneBank under the accession numbers AF042142) linked to a 10 residues spacer followed by the variable region of the SM3 antibody light chain (referred within the GeneBank under the accession numbers AF042143). Each variable region can be isolated by PCR from a prior art plasmid, such as pMAL-SM3 using either the tandem primers OTG12360 (SEQ ID NO: 10) and OTG12361 (SEQ ID NO: 11) for the insertion of the SM3-scFv sequence within the HindIII site of pTG14366 or the tandem primers OTG12344 (SEQ ID NO: 12) and OTG12361 (SEQ ID NO: 11) for the insertion of the SM3-scFv sequence within the HindIII site of pTG14365. The resulting constructs are named pTG14519 and pTG14552 (FIG. 2).

C. Isolation of MVA Infectious Particles.

A subclone of MVA has been isolated in GMP conditions from a crude material as described in Stickl et al. (1974, Deutsch Med Wochenschr 99, 2386-2392; Mayr et al., 1978, Zentralbl Bakteriol 167, 375-390). This subcloned is named MVATGN33.1. This parental MVA is routinely propagated and tittered onto CEFs.

CEFs are prepared from chicken embryo obtained from fertilized eggs previously incubated 11 days at 37° C. in a humid atmosphere. Chicken embryo are cut up into small pieces and treated with a solution of trypsin 2.5% (w/v). CEF are then plated onto Falcon 3001 plastic Petri dishes at a cell density of $1.5 \times 10^6$ cells/dish in Eagle Based Medium (MBE)/tryptose (Gibco BRL) complemented with 10% calf serum. After 48 h, monolayer cells are infected with the MVATGN33.1 for 30 min in PBS plus cations (magnesium acetate and $CaCl_2$ mg/ml each) plus 1% calf serum in order to adsorb the virus onto the cells. Infected cells are then cultivated for one hour in MBE plus 5% calf serum at 37° C. 5% $CO_2$. 1 to 5 g of plasmid (pTG14519 or pTG14552) are then precipitated in a solution of Hepes and $CaCl_2$. The precipitated DNA is layered onto the infected cell monolayer and incubated 2 h at 37° C. and 5% $CO_2$. A glycerol shock can be performed during 1 minute in order to facilitate the plasmid entry. For this purpose, a solution of 10% of glycerol in MBE/Tryptose is layered onto the cell monolayer for 1 min. Monolayers are then washed with PBS plus cations and incubated in MBE plus 5% of calf serum at 37° C. and 5% $CO_2$. After 48 h the Petri dishes are frozen.

The isolation of recombinant plaques is performed as follows: the Petri dishes are thawed, the infected cells are harvested and sonicated within the MBE/Calf serum. Recombinant viruses are then isolated by consecutive rounds of plaque purification in CEFs under the pression of the selection marker in the presence of 250 µg/ml of xanthin, 15 µg/ml of hypoxanthin, and 25 µg of mycophenolic acid as previously described by Falkner and Moss (1988, J. Virol. 62, 1849-1854).

A stock (viral seed) can be prepared in F175 flasks containing $10^8$ CEFs that are infected with the MVA. Viruses are propagated for 48 to 72 hours. The infected cells and the culture medium are pooled and the suspension is sonicated. Crude extracts are first fractionated onto a 36% sucrose cushion. Viral pellet is then fractionated onto a discontinuous sucrose gradient, as described in Joklik (1962, Virology 18, 9-18).

Example 2

Construction of a Recombinant MVA Expressing FCU-1 and Targeting MUC1 Positive Cells FCU-1 gene was isolated by HindIII/KpnI digestion of the DNA plasmid pTG13046 (referred as pCI-neoFCU1 in WO99/54481). The transfer vector containing the homologous sequences to the flanking regions of the deletion III named pTG6019 (Example 2 of WO99/03885) was modified as follow. The expression cassette coding for *E. coli* gpt placed under the control of the early late pH5R vaccinia virus promoter is isolated from the DNA plasmid pTG9996 by a SacI digestion. This DNA fragment is then inserted within the SacI site of the DNA plasmid pTG6019, to give pTG14033. The synthetic early late promoter p11K75 (SEQ ID NO: 13) is isolated by PCR from the template M13TG4052 with the primers OTG12271 (SEQ ID NO: 14) and OTG12272 (SEQ ID NO: 15). M13TG4052 is based on M13TG130 (Kieny et al., 1983, Gene 26, 91-99). The promoter 11K7.5 contains from 5' to 3' the sequence of the late promoter 11 k (Goebel et al., 1990, supra) up to nucleotide +4 of the transcription initiation site, the sequence of the TK promoter from nucleotides −28 to −13 having a C instead of a A at position −18 and the region between nucleotides −12 to +6 of the early 7.5 k promoter.

The amplified fragment is digested by BamHI and BglII restriction enzymes before being inserted within the BamHI site of pTG14033, to give pTG14084. The FCU-1 gene is cloned downstream the p11K75 promote by homologous recombination as follows. First, synthetic sequences are inserted between the PstI and BamHI sites of pTG14084 using OTG12522 (SEQ ID NO: 16) and OTG12523 (SEQ ID NO: 17). The DNA plasmid is then linearized by XhoI and homologous recombination with the FCU-1 gene is performed in E. coli. The resulting DNA plasmid is named pTG14322.

Homologous recombination in CEFs infected with MVATG14552 and transfected with pTG14322 results in the obtention of a MUC1 targeted MVA expressing the suicide gene FCU-1.

Example 3

Production of MVA with a Knockout of F13L Gene

The 5' F13L flanking region is isolated from MVATGN33 viral DNA by standard PCR assay using the tandem primers OTG13192 (SEQ ID NO: 18) and OTG13194 (SEQ ID NO: 19) and inserted between the BamHI and EcoRI sites of pBS (Stratagene) (pTG14746). The 3' F13L flanking region is isolated from MVATGN33 viral DNA by standard PCR assay using the tandem primers OTG13190 (SEQ ID NO: 20) and OTG13191 (SEQ ID NO: 21) and inserted between the BamHI and EcoRI sites of M13TG6131 to give M13TG14101. 5' and 3' F13L flanking regions are then cloned in the EcoRI site of pTG1E. The resulting construct is named pTG14783.

Example 4

Generation of a Producer Cell Line Expressing for the MUC-1 Antigen

As mentioned above, insertion of the SM3 scFv ligand moiety in the p14-kDa protein may affect virus production (reduced virus yield). Thus, targeted MVA of Example 1 are preferably isolated and propagated on a cell line exhibiting at the cell surface the MUC-1 antigen which is recognized by the SM3 antibody present at the viral surface, in order to reduce contamination with the wild type MVATGN33.1.

The cDNA encoding the membrane anchored form of MUC-1 antigen is isolated from pPOLYII-ETAtm (Hareuveni et al., 1990, Eur. J. Biochem 189, 475-486) by a double digestion with BglII and EcoRI restriction enzymes and inserted between the BamHI and EcoRI sites of the pcDNA3 expression vector (In Vitrogen, USA) downstream the CMV promoter. The resulting plasmid is named pTG5077.

$1 \times 10^6$ BHK-21 (ATCC CCL-10) cells are transfected with 5 μg of pTG5077 and subsequently cultured in GMEM (Glasgow Modified Eagle Medium, Gibco BRL) containing 20 g/l of Gentamycin and 10% fetal calf serum. After 24 h at 37° C. in 5% CO2 atmosphere, 1 mg/ml of G418 (Gibco BRL) is added. Neomycin resistant clones are then isolated by limit dilution and tested by FACS for MUC-1 expression at the cell surface using the H23 monoclonal antibody (Tsarfaty et al., 1989, in Breast cancer immunodiagnosis and Immunotherapy, Ed Ceriani, Plenum N.Y.). Interestingly, most of the MUC-1 positive clones loose the plastic adherence property of the parental BHK-21 cell line and start to grow in suspension. This observation will facilitate propagation and pharmaceutical production of the recombinant viruses of the invention in bioreactor.

Example 5

Evaluation of the Targeting Properties

Clones of MVATG14552 of Example 1 are isolated by consecutive rounds of plaque purification in CEFs under selective condition in the presence of xanthin, hypoxanthin and mycophenolic acid as described above.

A certain number of clones are first analyzed by PCR to detect the presence in the viral genome of the chimeric gene encoding the TG51/SM3scFv/p14kDa fusion protein. Nine clones are selected and further analyzed by Western Blot to confirm the expression of the fusion protein at the surface of the poxviral particles. Detection is performed with the ECL kit (Amersham) by immunoblotting with a p14-kDa specific rabbit polyclonal serum in crude extract obtained from infected cells or supernatants. Purified p14-kDa protein is used as a control. With the exception of clone C5, all the selected clones express the chimeric fusion protein that has a molecular mass of 46kDa. As expected, the intensity of the labeling is more intense in crude extracts than in culture supernatants reflecting the intracellular status of the poxviral particles. These results indicate that the majority of the poxviral exhibiting at their surface the TG51/SM3scFv/p14kDa fusion protein are IMV particles. The detection of weak amount of fusion protein in the culture supernatant can be explained either by a breakage of the EEV envelope or by a cellular lysis during clone preparation.

Infection properties of MVATG14552 have then be studied in different cell lines:

- The murine mastocytoma P815 (ATCC CRL6448),
- P815 expressing the MUC-1 antigen (P815-MUC1) obtained by transfection of the parental P815 cells with a vector expressing the membrane anchored form of MUC1 antigen,
- BHK 21 (Baby Hamster Kidney),
- BHK 21 expressing the MUC-1 antigen (BHK 21-MUC1) obtained by transfection of the parental BHK 21 cells with a vector expressing the membrane anchored form of MUC1 antigen.

Cells are infected with MVATG14552 clone 9 or with a control virus (MVAN33) at a MOI of approximately 0.1 for 24 h. Infection efficiency is determined by flow cytometry (FACS) after incubation with a polyclonal murine serum obtained after MVA immunization at a dilution rate of 1/100. Revelation is made by incubation with a monoclonal FITC goat anti-mouse IgG (Pharmingen, 10 μg/ml). As shown in FIG. 3A, MVATG14552 infects preferably MUC-1 expressing cells compared to the parental cells P815 and BHK-21. On the contrary, the control MVA infects both the MUC-1 expressing and non expressing cells with a similar efficiency (FIG. 3B).

All together, these results indicate that the ligand moiety SM3 scFv is expressed at the surface of the poxviral (IMV) particles and that it is capable of recognizing and binding to its target (the MUC-1 antigen) leading to a specific infection of said cells by the modified virus.

The interactions between two SM3 scFv expressing clones (A3 and C9) with a MUC-1 60 mer peptide were examined by Surface Plasmon Resonance (SPR), using a BIAcore XTM biosensor system (BIAcore AB, Uppsala, Sweden). All experiments were performed at 25° C. Steptavidine was covalently bound to the carboxylated dextran matrix of a SA sensor chip by amine coupling using the amine coupling kit (BIAcore AB, Uppsala, Sweden). Then, biotinylated 60 mer peptide representing 3 tandem repeats of MUC-1 (10 μg/ml in HBSS buffer) was immobilized in flow cell 2 on the SA sensor chip coated with steptavidine. Flow cell 1 served as reference. Binding of fluid phase recombinant SM3 was used as positive control. Binding of fluid phase recombinant viruses was determined over a range of $1\times10^6$-$1\times10^8$ pfu/ml in HBSS buffer. For this purpose, primary chicken fibroblasts were infected at a MOI of 1 during 24 h with the viral suspensions. Injection volumes were 15 μl and flow rate 5 μl/min. The surface was regenerated with 10 mM NaOH. Kinetic analysis was performed using a BIAevaluation 3.0 software. A specific and reproductible interaction between recombinant viruses and the 60 mer MUC-1 peptide was observed. The measurements were found to correlate with virus concentrations. Binding of control MVA (MVAN33) to the same peptide was never observed.

These results demonstrate that the SM3 scFv/p14 fusion protein associates with MVA particles and that the recombinant viruses recognize specifically a MUC-1-derived peptide.

Example 6

Purification of the SM3 scFv-expressing Viral Particles

In order to separate the non-recombinant wild type viral particles from the recombinant ones, a selection protocol was performed by the BIAcore technique to purify the recombinant SM3 scFv-expressing viral particles based on their capability of binding a MUC-1 peptide. A viral preparation made from clone A3 was injected in the BIAcore X system as described above. The viruses displaying a high affinity for the 60 mer MUC-1 peptide were recovered at the surface during the regeneration phase using 20 mM NaOH, as described in BIAcore X Instrument Handbook. Permissive cells were then infected with the recovered viruses, in the presence of EDTA (1 mM) to avoid the formation of viral aggregates and the recombinant viruses were selected by a double selection GUS/GPT. The absence of wild type non recombinant viruses was assessed in isolated clones by PCR. This new purification and selection protocol has allowed the obtention of several clones free of contaminating wild type viruses.

Example 7

Targeting of Poxviral Particles to Tumoral Cells

The broad tissue tropism of poxviral vectors may turn disadvantageous when genes encoding potentially harmful proteins (e.g. cytokines, cytotoxic proteins, suicide gene products) are expressed in surrounding normal tissues. Moreover, the overall in vivo efficiency of gene delivery might be reduced by a significant dilution of the virus in the organism due to the transduction of non-target cells. The development of poxvirus vectors with defined targeted entry pathways would therefore greatly improve the safety and efficacy of some current gene therapy strategies. This approach is of particular importance for example in cancers, which treatment usually requires injection of high-doses of cytotoxic drugs that kill both cancer and healthy cells. Thus, targeting may improve gene therapy procedures by restricting the viral tropism to specific tissue(s) of interest (e.g. cancer cells and not healthy tissue).

This example describes poxvirus vectors and poxviral particles engineered to specifically target colorectal cancers (e.g. primary and metastatic adenocarcinomas). The Guanylyl cyclase C (GC-C) receptor was chosen as a model target molecule and the Sta peptide(N T F Y C <u>CELC</u> C N P <u>AC</u> A <u>GC</u> Y as disclosed in SEQ ID NO: 24) as a model ligand moiety.

Figure 4:
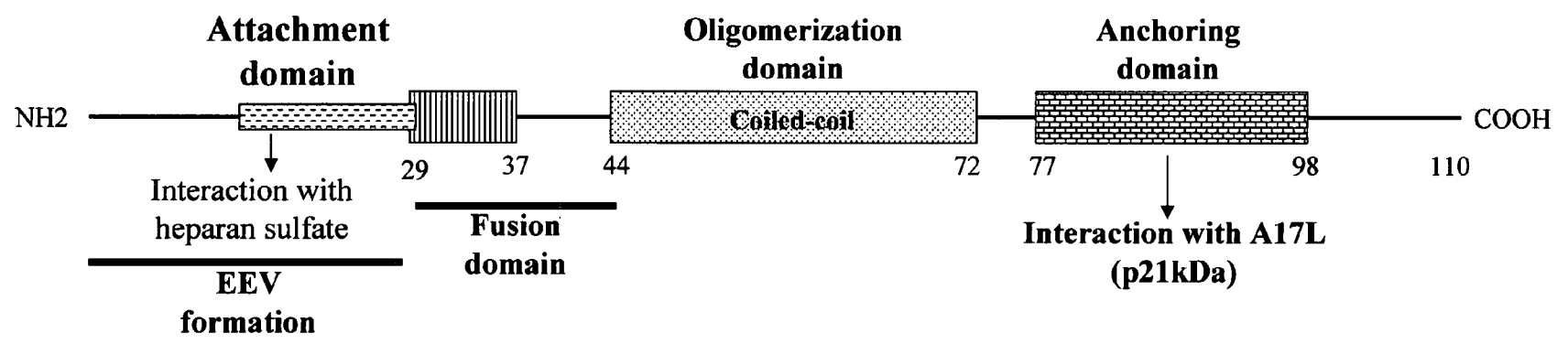

The entry of vaccinia virus into cells begins with the attachment of the virus to the cells, followed by membrane fusion to liberate the viral DNA into the cytoplasm of the infected cell. One of the protein which mediates the attachment and fusion process is the 14kDa protein. It exists in the virus as a trimer and the p14 monomer is a 110 amino acid long protein encoded by the A27L gene (138L gene in MVA). The structure of the P14 protein is illustrated in FIG. 4 (from Vazquez and Esteban, 1999, J. Virol. 73, 9098-9109). The domain responsible for the interaction with lipids or membranes in the Golgi stacks involved in EEV formation was found to be located within the first 29 amino acids at the p14 N-terminus. The fusion domain (responsible for virus cell fusion) and the attachment domain responsible for virus-cell attachment (implicated in the interaction with heparan sulfate) are located adjacent to each other, the fusion domain being located between residues 29 and 43 and the attachment domain comprises amino acids 21 to 33. The oligomerization domain responsible for trimer formation has been attributed to residues 44 to 72 (triple-stranded coiled coil structure). Finally, the anchoring domain allowing the interaction with the p21kDa protein, and thus the anchorage of the p14 protein to the IMV envelope, has been identified at the C-terminus between residues 77 to 98.

In an attempt to redirect the natural tropism of IMV particles to GC-C receptor-expressing cells, the Sta peptide was inserted by fusion at the N-terminus of the full-length p14 protein with or without the signal peptide of human trans-golgi Network glycoprotein TGN51 (Kain et al, 1998, J. Biol. Chem. 273, 981-988). Each of the Sta-p14 fusion genes was inserted in the viral genome in replacement of the native (p14 encoding) 138L gene. The GC-C receptor targeted MVA vectors were further modified by the incorporation of a therapeutic gene, e.g. the FCU-1 gene. The targeting properties of the resulting viruses and expression of the FCU-1 gene were evaluated both in vitro and in vivo using GC-C receptor-expressing cells (e.g. the human colon carcinoma T84 cell line) and GC-C receptor negative cells (e.g. the SW480 cell line) as a negative control.

7.1 Construction of a Recombinant MVA Expressing FCU-1 and Targeting GC-C Positive Tumor Cells Two constructions were engineered:

pTG16326 (FIGS. 5 and 6) expresses a chimeric MVA p14 protein in which the STa peptide is fused to the N-terminus of the MVA138L ORF (p14 protein).

pTG16355 (FIG. 5) is similar to MVA16326 vector with the exception of the presence of a signal peptide of the human trans-golgi network glycoprotein TGN51 fused at the N-terminus of the STa peptide.

The chimeric MVA138L ORF were created by hybridation and ligation of the below cited oligonucleotides. The resulting synthetic fragments were then amplified by PCR and inserted by homologous recombination in plasmid pTG14359, (see example 1), which contains MVA138L gene and flanking 5' and 3' regions.

Hybridation and ligation of primers OTG15144 (SEQ ID NO: 27), OTG15145 (SEQ ID NO: 28), OTG15150 (SEQ ID NO: 29), OTG-STAr (SEQ ID NO: 30), OTG-STA (SEQ ID NO: 31) and OTG15152 (SEQ ID NO: 32) gave rise to fragment A. For information, fragment A contains the 5' flanking region of MVA138L, the STa peptide fused to the N-terminus of the MVA138L ORF deleted of its ATG codon. This fragment was amplified with the tandem primer OTG15200 (SEQ ID NO: 33) and OTG15201 (SEQ ID NO: 34) and inserted by homologous recombination in pTG14359 digested by HindIII. The resulting construct is named pTG16077.

Hybridation and ligation of primers OTG15144 (SEQ ID NO: 27), OTG15145 (SEQ ID NO: 28), OTG15146 (SEQ ID NO: 35), OTG15147 (SEQ ID NO: 36), OTG15148 (SEQ ID NO: 37), OTG-STAr (SEQ ID NO: 30), OTG-STA (SEQ ID NO: 31) and OTG15152 (SEQ ID NO: 32) gave rise to fragment B. For information, fragment B contains the 5' flanking region of MVA138L, the TGN51 signal sequence fused to the STa peptide which in turn is fused to the N-terminus of MVA138L ORF deleted of its ATG codon. After amplification with the tandem primer OTG15200 (SEQ ID NO: 33) and OTG15201 (SEQ ID NO: 34), this fragment was introduced in pTG14359 by homologous recombination, giving rise to pTG16075.

The selection marker expression cassette coding for the *E. coli* gpt placed under the control of the early-late promoter pH5R was isolated by PCR from plasmid pTG14366 (Example 1.A) using the primers OTG15157 (SEQ ID NO: 38) and OTG15124 (SEQ ID NO: 39) to produce fragment E. Upstream the selection cassette, the fragment E also contains 413 pb of MVA137L gene. To improve the selection of recombinant virus, an expression cassette coding for the *Aequorea victoria* green fluorescent protein EGFP was used. The EGFP gene is placed under the control of the pH5R promoter. This promoter was amplified by PCR from DNA extracted from a wild type isolate of a vaccinia virus strain Copenhagen, using primers OTG4449 (SEQ ID NO: 40) and OTG4450 (SEQ ID NO: 41). The amplified fragment was digested by BglII and BamHI, and inserted in M13TG131 (Kieny et al, 1983, Gene 26, 91-99) restricted by the same enzymes, to give M13TG8124. The EGFP gene was amplified by PCR from pEGFP-C1 (Clontech) using primers OTG13628 (SEQ ID NO: 42) and OTG13629 (SEQ ID NO: 43). The amplified fragment was digested by BamHI and BglII, and introduced in M13TG8124 digested by BamHI, resulting in M13TG14126. The fragment E was cloned between SphI and BamHI sites of M13TG14126 to give rise to M13TG14148. The gpt-EGFP selection cassette was isolated from M13TG14148 by digestion with PacI and BglII, following by a treatment with T4 DNA polymerase, to generate fragment F. Fragment F was then cloned either within PacI-digested pTG16075 or pTG16077 (after treatment with T4 DNA polymerase). Final constructs are named pTG16355 (FIG. 5), and pTG16326 (FIGS. 5 and 6), respectively.

7.2 Production of GC-C Targeting MVA Particles

MVA viruses were generated in CEFs infected with either the wild-type virus MVATGN33.1 or a FCU-1 expressing MVA, e.g. MVATG15637 which contains the FCU1 gene inserted in deletion III (described in EP application 03 360087.5) or pTG14322 (Example 2). Homologous recombination in CEFs infected with the wild-type MVATGN33.1 and transfected with each of the above-described final constructs resulted in the obtention of a Sta-expressing MVA. The resulting viruses are designated MVATG16355 (TGN51ss/Sta/p14 fusion), and MVATG16326 (Sta/p14 fusion), respectively.

Homologous recombination in CEFs infected with a FCU-1 expressing virus (for example MVATG15637) and transfected with each of the above-described final plasmid constructs resulted in the obtention of a Sta-containing recombinant MVA expressing the therapeutic suicide gene FCU-1. The resulting viruses are designated MVATG16355x15637 and MVATG16326x15637, respectively.

7.3 Evaluation of the Targeting Properties a) Biochemical Analysis of Targeted Viruses The presence in the viral genome of the chimeric gene encoding the STa/p14kDa fusion was verified by PCR on MVA16326 and MVA16326x15637 viral stocks. After DNA extraction, PCR reactions were done using the following primers surrounding the STa insertion site. OTG15158 (SEQ ID NO: 44) was located in the MVA139L gene and OTG15159 (SEQ ID NO: 45) was located in the MVA138L gene. Amplification with these primers gave rise to a signal of 356 pb for the recombinant virus expressing the STa/p14kDa fusion, and a signal of 309 pb for the wild-type virus. A signal of 356 pb was observed, and no signal of 309 bp corresponding to the wild-type p14kDa encoding gene was obtained, indicating that the two viruses generated are pure recombinants without wild-type contaminants.

In addition, expression of the Sta/p14 fusion protein at the surface of the poxviral particles was analysed by Western-blot in crude extract obtained from CEF cells infected by MVA16326 and MVA16326x15637. Detection was performed with the ECL kit (Amersham), by immunoblotting with a p14-kDa specific mouse polyclonal serum. As a result, a product having a molecular mass of 16.5 kDa was highlighted in the infected cell cultures. The detected molecular mass corresponds to the one expected for the chimeric fusion protein and no signal of 14kDa corresponding to the wild-type p14-kDa protein was observed (confirming the absence of contamination).

b) Analysis of Targeted Viruses by Electronic Microscopy

Electron microscopy analyses were performed after infection of DF1 cells (ATCC CRL-12203) with MVA16326x15637. Infection with wild-type MVATGN33 were done as control. After infection with MVATGN33, a majority of enveloped forms were observed, either enveloped viruses released in the culture medium (EEV) or still associated to the cells (CEV for cell-associated enveloped virus). On the other hand, after infection with MVA16326x15637, a majority of IMV forms were obtained. This result showed that the insertion of the STa ligand at the N-terminus part of the p14 protein prevents the formation of EEV and CEV.

c) In Vitro Evaluation of MVA16326x15637

FCU1 gene expression was evaluated in vitro after transfection of cells expressing, or not, the GC-C receptor. The human colon carcinoma T84 cell line (ATCC CCL-248) was selected as a model of GC-C receptor-positive cells and SW480 cell line (ATCC CCL-228) as a negative control (GC-C receptor-negative cells). Expression of FCU-1 was shown to correlate with the rate of conversion of the prodrug 5-FC to 5FU and measurement of production of 5FU was performed by HPLC.

Cells were infected in suspension by the recombinant MVA at a MOI of 0.05. Twenty-four hours later, the cells were resuspended in 100 μl of lysis buffer (50 mM Tris-HCl pH 7.5, 150 mM NaCl, 5 mM EDTA, 1 mM DTT, 1% Triton X100) and incubated for 30 min at 4° C. Cellular debris were removed by centrifugation. To evaluate conversion of 5-FC to 5-FU, 5 μl of cell lysate were combined with 85 μl of reaction buffer (50 mM NaPi pH7.2) and 10 μl of 5-FC 10 mM diluted in reaction buffer were added. After 15 min at 37° C. the reaction was stopped by adding 1 ml of ethyl acetate:2-propanol:0.5M acetic acid (84:15:1). The samples were vortexed 10 seconds and centrifuged 5 min. The organic supernatant was removed and taken to dryness under $N_2$. The dried extract was reconstituted in 100 µl of milliQ water, vortexed and then analyzed by HPLC. 5-FC and 5-FU were separated isocratically on a Hewlett Packard HP 1090M liquid chromatograph with UV detection at 260 nm and 280 nm. A Supelco supelcosil LC-18-S (5 µm packing; 4.6×250 mm) column and a guard cartridge (10×3 mm Varian) were used with a flow rate of 1 ml/min. The mobile phase was 50 mM Phosphoric Acid adjust to pH 2.1 with Ammonia. The column was maintained at 35° C. The 5-FC and 5-FU reference samples were taken up in water at 1 mM and 20 µl are injected corresponding respectively to 2.58 µg and 2.6 µg. For the enzymatic reaction 20 µl of the samples are injected.

As a preliminary evaluation, Fcu-1 expression levels measured after infection with the MVA15637 (FCU-1-expressing control with the wild type p14) and with MVA16326x15637 (FCU-1-expressing virus carrying a STa-P14 fusion protein in place of native p14) were comparable in both T84 and SW480 cell lines. An hypothesis to explain these results might be that the addition of the STa peptide at the N-terminus of the wild-type p14 protein is not sufficient to alter the natural tropism of the Sta-p14 fusion displaying viruses MVA16326 and MVA16326x15637. In the absence of "detargeting" (i.e. ablation of the natural tropism), these viruses are still capable of efficiently infecting their natural host cells, and therefore the targeting properties provided by the STa peptide might be not apparent.

Example 8

Construction of a Modified p14 Protein Detargeted and Retargeted to GC-C Receptor Positive Tumoral Cells A modified MVA p14 protein was constructed by deletion of the N-terminal 29 amino acids which, in the wild-type context, are involved in EEV formation and interaction with cellular heparan sulfate. Such a modification is expected to reduce the native viral infectivity (p14 native tropism directed to the ubiquitous heparan sulfate-containing receptors). Addition of the Sta peptide in the deleted p14 version is aimed to retarget infection to GC-C receptor-positive cells (such as T84). The Sta peptide was inserted at the N-terminus of the. deleted p14 protein with or without the signal peptide of human trans-golgi Network glycoprotein TGN51 (Kain et al, 1998, J. Biol. Chem. 273, 981-988). Of course, the constructions contain an initiator Met residue.in position +1 of the translated product.

As illustrated in FIG. 5, two constructions were engineered.

MvA16367 is similar to MVA16326 vector (Example 7) with the exception that the 29 first amino-acids of the MVA138L ORF are deleted. Thus, this constructs expresses a chimeric p14 protein in which the STa peptide is fused to the N-terminus of the modified p14 protein deleted of its N-terminal 29 amino acid residues.

MVA16356 is similar to MVA16355 vector (Example 7) with the exception that the 29 first amino-acids of the MVA138L ORF are deleted. Thus, this construct expresses a chimeric p14 protein comprising the signal peptide of the human trans-golgi network glycoprotein TGN51 fused at the N-terminus of the STa peptide, which in turn is fused to the N-terminus of the modified p14 protein deleted of its N-terminal 29 amino acid residues .

Each of the various Sta-138L fusion genes was inserted in the viral genome in replacement of the native (p14 encoding) 138L gene, as described in Example 7 with the exception that the following oligonucleotides were used to generate the synthetic fragments C and D which were then amplified by PCR and inserted by homologous recombination in plasmid pTG14359.

Hybridation and ligation of primers OTG15144 (SEQ ID NO: 27), OTG15145 (SEQ ID NO: 28), OTG15150 (SEQ ID NO: 29), OTG-STAr (SEQ ID NO: 30), OTG-STAdel (SEQ ID NO: 46) and OTG15154 (SEQ ID NO: 47) gave rise to fragment C. For information, fragment C contains the 5' flanking region of MVA138L, the STa peptide fused to the N-terminus of MVA138L ORF deleted from its 29 first amino-acids. After amplification with the tandem primer OTG15200 (SEQ ID NO: 33) and OTG15202 (SEQ ID NO: 48), this fragment was introduced in pTG14359 by homologous recombination, giving rise to pTG16078.

Hybridation and ligation of primers OTG15144 (SEQ ID NO: 27), OTG15145 (SEQ ID NO: 28), OTG15146 (SEQ ID NO: 35), OTG15147 (SEQ ID NO: 36), OTG15148 (SEQ ID NO: 37) and OTG-STAr (SEQ ID NO: 30), OTG-STAdel (SEQ ID NO: 46) and OTG15154 (SEQ ID NO: 47) gave rise to fragment D. For information, fragment D contains the 5' flanking region of MVA138L, the TGN51 signal sequence fused to the STa peptide which in turn is fused to the N-terminus of MVA138L ORF deleted from its 29 first amino-acids. After amplification with the tandem primer OTG15200 (SEQ ID NO: 33) and OTG15202 (SEQ ID NO: 48), this fragment was introduced in pTG14359 by homologous recombination, giving rise to pTG16076.

Insertion of Fragment F (gpt-EGFP selection cassette) in either PacI-digested pTG16076 or pTG16078 gives final plasmid constructs named pTG16356 and pTG16367 (see FIG. 5), respectively.

MVA viruses can be generated as described in example 7, e.g. in CEFs infected with either the wild-type virus MVATGN33.1 or the FCU-1 expressing MVA.M-VATG15637, to generate MVATG16356 (TGN51ss/Sta/del29 p14 fusion), and MVATG16367 (Sta/del29 p14 fusion), respectively. Homologous recombination in CEFs infected with MVATG15637 generates MVATG16356x15637 and MVATG 16367x15637 respectively.

The targeting properties of the resulting viruses and expression of the FCU-1 gene could be evaluated both in vitro and in vivo using GC-C receptor-expressing cells (e.g. the human colon carcinoma T84 cell line) and GC-C receptor negative cells (e.g. the SW480 cell line) by the techniques described in Example 7. For example, expression of the chimeric Sta/p14)aa1-29 fusion protein at the surface of the poxviral particles can be analysed by Western-blot in CEF-infected extracts using the above-described p14-kDa specific mouse polyclonal serum. Infection specificity can also be determined by evaluating FCU-1 expression after transfection of cells expressing, or not, the GC-C receptor or by infectivity analysis.

It is expected that the viruses MVATG16356, MVATG16367, MVATG16356x15637 and MVATG16367x15637 comprising in replacement of the wild-type p14 protein the deleted p14 version are less proned to infect SW480 cell line and more proned to infect T84 cell line due to the presence of the Sta peptide.

Example 9

Generation of p14 (M138L Gene) Knock-out Vaccinia Virus

The ORF encoding the MvA138L gene was deleted and replaced by a selection marker expression cassette coding for the *E. coli* gpt gene placed under the control of the hybrid promoter p4BK1L (hybrid between the early promoter p4B and the late promoter pK1L) and an expression cassette coding for the HSV-TK gene under the control of the early promoter p7.5K.

M13TG4073 containing the selection cassette coding for the *E. coli* gpt gene placed under the control of the hybrid promoter p4BK1L was described in WO99/03885 (see Example 7). The early promoter p7.5K is isolated from MVATGN33 viral DNA by standard PCR using the tandem primers OTG7688 (SEQ ID NO: 49) and OTG7690 (SEQ ID NO: 50) and inserted between the BamHI and BglII sites of M13TG6131 (Example 7 of WO99/03885), giving rise to M13TG9165. The coding sequence of the HSV-TK gene (reference Genbank: AF057310) was generated as a BamHI-BglII fragment and inserted in the BamHI site of M13TG9165, giving rise to M13TG14105.

A BamHI-BglII fragment obtained from M13TG4073, and containing the p4BK1L-gpt cassette, was inserted in BamHI site of M13TG14105, resulting in M13TG14116. A fragment containing the p4BK1L-GPT cassette and the p7.5K-HSV TK cassette was generated by digestion of M13TG14116 with BamHI and BglII, and treatment with T4 DNA polymerase. It was introduced in pTG14359 digested with HindIII and NdeI (to delete MVA138L gene), and treated with T4 DNA polymerase, resulting in pTG14892.

The knock-out virus can be produced by homologous recombination in appropriate cells transgected with the shuttle plasmid pTG14892 and an appropriate pMVA genome (e.g. a wild type virus). If necessary, several rounds of selection can be performed to reduce the contamination by the wild type virus and obtain pure virus stocks. In a single preliminary experiment, homologous recombination was performed in CEFs infected with MVATGN33 and transfected with pTG14892. Eight steps of selection were necessary to obtain a pure recombinant virus without any contamination with MVATGN33. However, the virus MVATG14892 (1.3.1.1.3.9.5.7) vas no more able to be propagated on CEFs.

Example 10

Generation of a Complementation Cell Line Expressing for the p14-kDa Protein The insertion of a ligand (e.g. the Sta ligand) and/or the deletion of the N-terminal portion of the p14-kDa protein may affect virus production. In this context, it is proposed to carry out the isolation and the first steps of the production process of the de- and retargeted MVA viruses (e.g. those of Examples 7 and 8) using a cell line expressing the wild-type p14-kDa protein, in order to complement, at least to some extent, the p14-kDa defect. The final step of the production process will be performed in a non-complementing cell line (i.e. a cell line which does not express a wild-type p14 protein), in order to obtain poxviral particles exhibiting the modified p14 version at their surface.

A p14 complementation cell line was generated by transfection of an expression vector expressing the wild-type p14 protein in the DF1 cell line (U.S. Pat. No. 5,672,485, available at ATCC under accession number CRL-12203).

10.1 Isolation of Cell Lines Expressing p14

The MVA138L ORF containing a BamHI site at the 5' end and an EcoRI site at the 3' end, was amplified by PCR with primers OTG13641 (SEQ ID NO: 51) and OTG12708 (SEQ ID NO: 52) using MVATGN33 viral DNA as template. The PCR product was blunt-ended by T4 DNA polymerase enzyme and subcloned into the SmaI site of eukaryotic expression vector pCI-neo (Promega), to isolate pTG16233. In this plasmid, the MVA 138L gene sequence is placed under the control of the CMV promoter.

Monolayers of $3 \times 10^6$ DF1 cells in 10 cm tissue culture plates were transfected with 10 µg of pTG16233, using Superfect reagent (Qiagen). After 48 h at 39° C., cells were washed and selections were made by adding selection medium constituted by DMEM (Invitrogen) containing 4.5 g/l of glucose, 4 mM of glutamine, 40 mg/l of gentamycine, 10% of fetal calf serum and 1 mg/ml of G418. Neomycin resistant clones were then isolated by limit dilution. 84 clones were obtained. Expression of MVA138L gene was assayed by Western-blot analysis using a p14-kDa specific mouse polyclonal serum. A protein of about 14 kDa which is similar in size to the p14-kDa gene product that is synthesized during infection with wild-type virus was detected in 38 clones by the mouse anti-p14-kDa polyclonal serum. The amount of p14 detected in these clones was significantly lower than the amount present at the late time-points in MVA infection. The complementation properties of the selected 38 clones was evaluated for propagation of p14 knock-out mutant viruses (Example 9).

10.2 Complementation of P14⁻ Virus by DF1/p14 Cells

As described in Example 9, attempts to generate a MVA recombinant virus with a deletion of the 138L gene in CEF cells were poorly efficient and resulted in a virus (MVATG14892 1.3.1.1.3.9.5.7) unable to be efficiently propagated on CEF cells. So this virus was used to infect 4 different clones of DF1/p14 cells (12.2, 19.1, 20.5 and 20.8). Seven virus plaques able to be amplify were obtained. PCR analysis and Western-blot analysis showed no P14. Primary viral stocks were done for these 7 viruses. PCR and Western-blot analysis showed that three of them (12.2(8), 20.5(5) and 20.8(1) ) contained no more P14. These 3 knock-out viruses gave rise to small virus plaques after infection of DF1/p14 cell lines, while no plaque were obtained after infection of DF1 cells, CEF cells or BHK21 cells. So the DF1/p14 cell lines could be considered as a complementation cell line, as they allowed the propagation of p14⁻ knock out mutant virus.

To determine the extent to which DF1/p14 cells complement the p14 deletion, immunoelectron microscopy analyses were performed after infection of DF1 or DF1/p14 cells by the knock out (p14⁻) mutant. Infection with wild-type MVAN33 were done as control. Thin sections of infected cells were incubated with p14-kDa specific mouse polyclonal serum or B5R protein specific rabbit polyclonal serum, followed by anti-mouse or anti-rabbit antibodies conjugated to gold particles. After infection with MVAN33, a majority of enveloped forms were observed, especially a lot of CEV, which were labeled with both anti-sera. As expected, IMV were only labeled by the p14-kDa antiserum. After infection of DF1 cells with the knock out (p14⁻) mutant, only IMV forms were obtained and no specific labeling was observed. On the other hand, after infection of DF1/p14 cells with the knock out (p14⁻) virus, a few CEV and EEV, labeled with both anti-sera, were observed. Moreover IMV showed a weak labeling with the p14-kDa anti-serum. These results indicated that the DF1/p14 cells are capable of complementing at least partially the phenotypic defect of vaccinia virus p14⁻ knock out mutants.

All together, the experimental data described herein provide poxvirus vectors with new infection specificity directed to tumor cells expressing specific tumor-associated antigens such as MUC-1 or tumor-associated receptors such as the GC-C receptor. Moreover, these data describe a complementation cell line expressing a late IMV protein that together with p14 knock out mutants could be useful for efficiently producing these new poxvirus vectors.

The invention claimed is:

1. A poxviral particle,
wherein the genome of said poxviral particle lacks the gene encoding a wild-type p14 protein and comprises a nucleic acid encoding a modified p14 protein,
wherein said modified p14 protein comprises the deletion of at least one amino acid residue normally present in the wild-type p14 protein, within the region involved in the interaction with one or more native cellular receptors and in the formation of enveloped viral particles,
wherein said modified p14 protein exhibits a reduced ability to bind to said one or more native cellular receptors and a reduced ability to produce EEV (Extracellular Enveloped Virus) particles, as compared to the corresponding wild-type p14 protein;

wherein said modified p14 protein retains the ability to trimerize and to associate with a poxviral 21 kDA protein, wherein said modified p14 protein further comprises an heterologous ligand moiety inserted at its N-terminus, and wherein said poxviral particle is an IMV (Intracellular Mature Virus).

2. The poxviral particle of claim 1, wherein said poxviral particle is a Modified Vaccinia Virus Ankara (MVA) particle comprising a MVA vector lacking the 138L gene encoding the wild-type p14 protein and comprising in replacement a nucleic acid encoding said modified p14 protein.

3. The poxviral particle of claim 1, wherein said poxviral particle further comprises a nucleic acid of interest.

4. An isolated eukaryotic host cell comprising the poxviral particle according to claim 1.

5. A process for producing the poxviral particle according to claim 1, comprising the steps of:

a) preparing a culture of a first cell wherein said first cell is capable of providing a wild-type p14 protein;

b) infecting said first cell with a poxviral particle comprising a poxvirus genome which is defective for the wild-type p14 protein and transfecting in said first cell a shuffle plasmid and homologous sequences flanking on both sides the desired insertion site in the poxvirus genome;

c) culturing said transfected or infected first cell for an appropriate period of time and under suitable conditions for producing poxviral particles comprising a poxviral genome;

d) recovering the resulting poxviral particles from the cell culture and/or the culture supematant of said first cell;

e) infecting a second cell with the recovered poxviral particles;

f) culturing said infected second cell for an appropriate period of time and under suitable conditions for producing poxviral particles;

g) recovering the resulting poxviral particles from the cell culture and/or the culture supematant of said second cell, and h) optionally, purifying the recovered poxviral particles.

6. A composition comprising the poxviral particle according to claim 1.

7. The composition of claim 6, further comprising a pharmaceutically acceptable carrier.

8. The poxviral particle of claim 1, wherein at least one of said one or more native cellular receptors is a cellular heparan sulfate receptor.

9. The poxviral particle of claim 1, wherein said modified p14 protein lacks the N-terminal residues 2-33, 2-32, 2-31, 2-30, 2-29 or 2-28 of the wild-type p14 protein.

10. The poxviral particle of claim 9, wherein said modified p14 protein lacks the N-terminal residues 2-29 or 2-28 of the wild-type p14 protein.

11. The poxviral particle of claim 10, wherein said modified p14 protein lacks the N-terminal residues 2-28 of the wild-type p14 protein.

12. The poxviral particle of claim 9, wherein said modified p14 protein comprises the amino acid sequence of SEQ ID NO: 26.

13. The poxviral particle of claim 1, wherein said heterologous ligand moiety is capable of binding a tumor-specific antigen, a cellular protein differentially or overexpressed on tumoral cells or a gene product of a cancer-associated virus.

14. The poxviral particle of claim 13, wherein said heterologous ligand moiety is capable of recognizing and binding to the guanylyl cyclase C (GC-C) receptor.

15. The poxviral particle of claim 14, wherein said heterologous ligand moiety comprises any one of SEQ ID NOs: 22, 23, 24 or 25.

16. The poxviral particle of claim 15, wherein said heterologous ligand moiety is the Sta peptide which comprises the sequences shown in SEQ ID NO: 24.

17. The poxviral particle of claim 1, wherein said poxviral particle is a vaccinia virus, canarypox, fowlpox, cowpox, entomopox, monkey pox, swine pox or penguin pox particle.

18. The poxviral particle of claim 17, wherein said poxviral particle is a vaccinia virus.

19. The poxviral particle of claim 18, wherein said vaccinia virus is selected from the group consisting of Copenhagen, Wyeth and Ankara modified (MVA) strains.

* * * * *